(12) United States Patent
Oxvig et al.

(10) Patent No.: US 8,653,020 B2
(45) Date of Patent: Feb. 18, 2014

(54) SELECTIVE EXOSITE INHIBITION OF PAPP-A ACTIVITY AGAINST IGFBP-4

(75) Inventors: Claus Oxvig, Viby (DK); Jakob Hauge Mikkelsen, Aarhus C (DK); Claus Gyrup Nielsen, Maløv (DK)

(73) Assignee: Aarhus Universitet, Aarhus C (DK)

(*) Notice: Subject to any disclaimer, the term of this patent is extended or adjusted under 35 U.S.C. 154(b) by 232 days.

(21) Appl. No.: 12/864,604

(22) PCT Filed: Jan. 23, 2009

(86) PCT No.: PCT/EP2009/050796
§ 371 (c)(1),
(2), (4) Date: Jul. 26, 2010

(87) PCT Pub. No.: WO2009/092806
PCT Pub. Date: Jul. 30, 2009

(65) Prior Publication Data
US 2010/0310646 A1    Dec. 9, 2010

Related U.S. Application Data

(60) Provisional application No. 61/023,631, filed on Jan. 25, 2008, provisional application No. 61/025,545, filed on Feb. 1, 2008.

(30) Foreign Application Priority Data

Feb. 1, 2008  (DK) ................................ 2008 00148

(51) Int. Cl.
*C07K 14/00* (2006.01)
(52) U.S. Cl.
USPC .............................................. 514/1; 530/350
(58) Field of Classification Search
USPC .............................................. 514/1; 530/350
See application file for complete search history.

(56) References Cited

U.S. PATENT DOCUMENTS

| | | |
|---|---|---|
| 4,399,216 A | 8/1983 | Axel et al. |
| 4,474,893 A | 10/1984 | Reading |
| 4,486,533 A | 12/1984 | Lambowitz |
| 4,599,311 A | 7/1986 | Kawasaki |
| 4,615,974 A | 10/1986 | Kingsman et al. |
| 4,634,665 A | 1/1987 | Axel et al. |
| 4,661,454 A | 4/1987 | Botstein et al. |
| 4,845,075 A | 7/1989 | Murray et al. |
| 4,870,008 A | 9/1989 | Brake |
| 4,881,175 A | 11/1989 | Ladner |
| 4,882,279 A | 11/1989 | Cregg |
| 4,931,373 A | 6/1990 | Kawasaki et al. |
| 4,935,349 A | 6/1990 | McKnight et al. |
| 4,946,778 A | 8/1990 | Ladner et al. |
| 4,954,617 A | 9/1990 | Fanger et al. |
| 4,977,092 A | 12/1990 | Bitter |
| 4,990,446 A | 2/1991 | Oberto et al. |
| 5,013,653 A | 5/1991 | Huston et al. |
| 5,037,743 A | 8/1991 | Welch et al. |
| 5,063,154 A | 11/1991 | Fink et al. |
| 5,091,513 A | 2/1992 | Huston et al. |
| 5,132,405 A | 7/1992 | Huston et al. |
| 5,139,936 A | 8/1992 | Botstein et al. |
| 5,143,830 A | 9/1992 | Holland et al. |
| 5,162,228 A | 11/1992 | Sumino et al. |
| 5,179,017 A | 1/1993 | Axel et al. |
| 5,223,409 A | 6/1993 | Ladner et al. |
| 5,258,498 A | 11/1993 | Huston et al. |
| 5,260,203 A | 11/1993 | Ladner et al. |
| 5,300,435 A | 4/1994 | Granados |
| 5,455,030 A | 10/1995 | Ladner et al. |
| 5,476,786 A | 12/1995 | Huston |
| 5,482,858 A | 1/1996 | Huston et al. |
| 5,545,806 A | 8/1996 | Lonberg et al. |
| 5,545,807 A | 8/1996 | Surani et al. |
| 5,554,372 A | 9/1996 | Hunter |
| 5,569,825 A | 10/1996 | Lonberg et al. |
| 5,625,126 A | 4/1997 | Lonberg et al. |
| 5,633,425 A | 5/1997 | Lonberg et al. |
| 5,641,655 A | 6/1997 | Foster et al. |
| 5,661,016 A | 8/1997 | Lonberg et al. |
| 5,716,808 A | 2/1998 | Raymond |
| 5,723,125 A | 3/1998 | Chang et al. |
| 5,736,383 A | 4/1998 | Raymond |
| 5,770,429 A | 6/1998 | Lonberg et al. |
| 5,789,208 A | 8/1998 | Sharon |
| 5,789,650 A | 8/1998 | Lonberg et al. |

(Continued)

FOREIGN PATENT DOCUMENTS

| | | |
|---|---|---|
| EP | 0 173 494 | 3/1986 |
| EP | 0 338 841 | 10/1989 |

(Continued)

OTHER PUBLICATIONS

Authorized Officer Agnes Wittmann-Regis, International Preliminary Report on Patentability, PCT/EP2009/050796, dated Jul. 27, 2010, 11 pages.
Authorized Officer Guenter Hillenbrand, International Search Report and Written Opinion of the International Searching Authority, PCT/EP2009/050796, mailed Jul. 31, 2009, 19 pages.
Bailey and Possee, "Manipulation of baculovirus vectors," in *Methods in Molecular Biology, vol. 7: Gene Transfer and Expression Protocols*, Murray (ed.), pp. 147 168 (The Humana Press, Inc. 1991.
Bayer and Rapp, "New polymer supports for solid-liquid-phase peptide synthesis," *Chem. Pept. Prot.*, 1986, 3:1-6.
Becker et al., "Use of recombinant adenovirus for metabolic engineering of mammalian cells," *Meth. Cell Biol.*, 1994, 43:161-189.

(Continued)

*Primary Examiner* — Karen Cochrane Carlson
(74) *Attorney, Agent, or Firm* — Fish & Richardson P.C.

(57) ABSTRACT

The present invention relates in one embodiment to PAPP-A exosite(s) interactors such as antibodies which bind to a region comprising LNR3 of PAPP-A and efficiently inhibit proteolysis of IGFBP-4, but not -5. The region comprising LNR3 represents a substrate binding exosite, which can be targeted for selective proteolytic inhibition. Accordingly, the present invention relates in one embodiment to differential inhibition of natural protease substrates by exosite targeting.

15 Claims, 8 Drawing Sheets

(56) References Cited

U.S. PATENT DOCUMENTS

| | | | |
|---|---|---|---|
| 5,814,318 | A | 9/1998 | Lonberg et al. |
| 5,874,299 | A | 2/1999 | Lonberg et al. |
| 5,876,735 | A | 3/1999 | Reed |
| 5,877,397 | A | 3/1999 | Lonberg et al. |
| 6,071,517 | A | 6/2000 | Fanger et al. |
| 6,335,163 | B1 | 1/2002 | Sharon |
| 2003/0118592 | A1 | 6/2003 | Ledbetter et al. |
| 2003/0124529 | A1 | 7/2003 | Oxvig et al. |
| 2003/0133939 | A1 | 7/2003 | Ledbetter et al. |
| 2005/0009136 | A1 | 1/2005 | Nixon et al. |
| 2005/0112675 | A1 | 5/2005 | Kocahn et al. |

FOREIGN PATENT DOCUMENTS

| | | |
|---|---|---|
| EP | 0 171 496 | 6/1993 |
| EP | 0 120 694 | 7/1993 |
| EP | 0 194 276 | 8/1993 |
| EP | 0 742 830 | 7/2001 |
| EP | 0 125 023 | 6/2005 |
| GB | 2188638 | 10/1987 |
| JP | 2005-151994 | 6/2005 |
| JP | 2005-525789 | 9/2005 |
| WO | WO 87/04462 | 7/1987 |
| WO | WO 88/00052 | 1/1988 |
| WO | WO 89/01036 | 2/1989 |
| WO | WO 91/00906 | 1/1991 |
| WO | WO 91/10741 | 7/1991 |
| WO | WO 92/03917 | 3/1992 |
| WO | WO 92/03918 | 3/1992 |
| WO | WO 92/06204 | 4/1992 |
| WO | WO 92/22645 | 12/1992 |
| WO | WO 93/01227 | 1/1993 |
| WO | WO 94/09131 | 4/1994 |
| WO | WO 94/10332 | 5/1994 |
| WO | WO 94/13804 | 6/1994 |
| WO | WO 94/13806 | 6/1994 |
| WO | WO 94/25585 | 11/1994 |
| WO | WO 95/21258 | 8/1995 |
| WO | WO 97/17450 | 5/1997 |
| WO | WO 97/17451 | 5/1997 |
| WO | WO 97/20078 | 6/1997 |
| WO | WO 98/02536 | 1/1998 |
| WO | WO 98/02565 | 1/1998 |
| WO | WO 98/24884 | 6/1998 |
| WO | WO 99/45962 | 9/1999 |
| WO | WO 00/73430 | 12/2000 |
| WO | WO 01/09187 | 2/2001 |
| WO | WO 02/43478 | 6/2002 |
| WO | WO 03/042661 | 5/2003 |
| WO | WO 2004/058052 | 7/2004 |
| WO | WO 2005/035732 | 4/2005 |
| WO | WO 2005/049648 | 6/2005 |
| WO | WO 2008/045962 | 4/2008 |

OTHER PUBLICATIONS

Benoist et al., "In vivo sequence requirements of the SV40 early promoter region," *Nature*, 1981, 290:304-310.

Bird et al., "Single-chain antigen-binding proteins," *Science*, 1988, 242:423-426.

Bonning, et al., "Superior expression of juvenile hormone esterase and Beta-galactosidase from the basic protein promoter of *Autographa californica* nuclear polyhedrosis virus compared to the p10 protein and polyhedron promoters," *J. Gen. Virol.*, 1994, 75:1551-1556.

Bowie and Sauer, "Identifying determinants of folding and activity for a protein of unknown structure," *Proc. Natl Acad. Sci. USA*, 1989, 86:2152-2156.

Brennan et al., "Preparation of bispecific antibodies by chemical recombination of monoclonal immunoglobulin G1 fragments," *Science*, 1985, 229:81-83.

Brüggeman et al., "Designer mice: the production of human antibody repertoires in transgenic animals," *Year Immunol.*, 1993, 7:33-40.

Brüggeman et al., "Human antibody production in transgenic mice: expression from 100 kb of the human IgH locus," *Eur J Immunol*, 1991, 21:1323-1326.

Chazenbalk and Rapoport, "Expression of the extracellular domain of the thyrotropin receptor in the baculovirus system using a promoter active earlier than the polyhedrin promoter. Implications for the expression of functional highly glycosylated proteins," *J. Biol. Chem.*, 1995, 270:1543-1549.

Chen et al., "Immunoglobulin gene rearrangement in B-cell deficient mice generated by targeted deletion of the J.sub.H locus," *International Immunology*, 1993, 5:647-656.

Chung et al., "Probing the role of loop 2 in Ras function with unnatural amino acids," *Proc. Natl Acad. Sci. USA*, 1993, 90:10145-10149.

Chung et al., "Probing the structure and mechanism of Ras protein with an expanded genetic code," *Science*, 1993, 259:806-809.

Content et al., "Expression and preliminary deletion analysis of the 42 kDa 2 5A synthetase induced by human interferon," in *Biological Interferon Systems*, Proceedings of ISIR-TNO Meeting on Interferon Systems, 1987, Cantell (ed.), pp. 65-72.

Cortese et al., "Selection of biologically active peptides by phage display of random peptide libraries," *Curr. Opin. Biotechnol.*, 1996, 7:616-621.

Coumailleau et al., "Definition of a minimal domain of the dioxin receptor that is associated with Hsp90 and maintains wild type ligand binding affinity and specificity," *J. Biol. Chem.*, 1995, 270:25291-25300.

Dawson et al., "Synthesis of proteins by native chemical ligation," *Science*, 1994, 266:776-779.

Dawson, "Synthesis of chemokines by 45 native chemical ligation," *Methods Enzymol.*, 1997, 287:34-45.

Derbyshire et al., "A simple and efficient procedure for saturation mutagenesis using mixed oligodeoxynucleotides," *Gene*, 46:145-152, 1986.

Deutscher, (ed.), "Guide to protein purification," *Meth. Enzymol.*, 1990, 182:529-539.

Douglas and Curiel, "Adenoviruses as 53 vectors for gene therapy," *Science & Medicine*, 1997, 4:44-53.

Duchosal et al., "Immunization of hu-PBLSCID mice and the rescue of human monoclonal Fab fragments through combinatorial libraries," *Nature*, 1992, 355:258-262.

Ellman et al., "Biosynthetic method for introducing unnatural amino acids site-specifically into proteins," *Methods Enzymol.*, 1991, 202:301-336.

Etcheverry, "Expression of engineered proteins in mammalian cell culture," in *Protein Engineering: Principles and Practice*, Cleland et al. (eds.), pp. 163-181 (John Wiley & Sons, Inc. 1996.

Fischer, et al., "Molecular farming of recombinant antibodies in plants," *Biol.Chem.*, 1999, 380:825-839.

Fishwild et al., "High-avidity human IgGκ monoclonal antibodies from a novel strain of minilocus transgenic mice," *Nature Biotechnology*, 1996, 14:845-851.

Foecking et al., "Powerful and versatile enhancer-promoter unit for mammalian expression vectors," *Gene*, 1980, 45:101-105.

Ford et al., "Fusion tails for the recovery and purification of recombinant proteins," *Protein Expression and Purification*, 1991, 2:95-107.

Fukunaga et al., "Identification of functional domains of the aryl hydrocarbon receptor ," *J. Biol. Chem*, 1995, 270:29270-29278.

Garnier et al., "Scale-up of the adenovirus expression system for the production of recombinant protein in human 293S cells," *Cytotechnol.*, 1994, 15:145-155.

GenBank Accession No. NP_000590, dated Sep. 24, 2011, 3 pages.

Georgiou, "Expression of proteins in bacteria," in *Protein Engineering: Principles and Practice*, Cleland et al. (eds.), 1996, (John Wiley & Sons, Inc.), pp. 101-127.

Geysen et al., "Use of peptide synthesis to probe viral antigens for epitopes to a resolution of a single amino acid," *Proc. Natl. Acad. Sci. USA*, 1983, 81:3998-4002.

Gleeson et al., "Transformation of the methylotrophic yeast *Hansenula pobmorpha*," *J. Gen. Microbiol.*, 1986, 132:3459-3465.

Glennie et al., "Preparation and performance of bispecific F(ab' gamma)2 antibody containing thioether-linked Fab' gamma fragments," *J. Immunol.*, 1987, 139:2367-2375.

(56) References Cited

OTHER PUBLICATIONS

Glick and Whitney, "Factors affecting the expression of foreign proteins in *Escherichia coli*," *J. Ind. Microbiol.*, 1987, 1:277-282.

Gorman et al., "The Rous sarcoma virus long terminal repeat is a strong promoter when introduced into a variety of eukaryotic cells by DNA-mediated transfection," *Proc. Natl. Acad. Sci. USA*, 1982, 79:6777-6781.

Graziano et al., "Construction and characterization of a humanized anti-gamma-Ig receptor type I (Fc gamma RI) monoclonal antibody," *J. Immunol.*, 1995, 155(10):4996-5002.

Green et al., Antigen-specific human monoclonal antibodies from mice engineered with human Ig heavy and light chain YACs, *Nature Genet.*, 1994, 7:13-21.

Greenberg et al., "A new antigen receptor gene family that undergoes rearrangement and extensive somatic diversification in sharks," *Nature*, 1995, 374:168-173.

Grisshammer et al., "Purification of over-produced proteins from *E. coli* cells," in *DNA Cloning 2: Expression Systems*, 1995, 2nd Edition, Glover et al. (eds.), pp. 59-92.

Grussenmeyer et al., "Complexes of polyoma virus medium T antigen and cellular proteins," *Proc. Natl. Acad. Sci. USA*, 1985, 82:7952-7954.

Hackeng et al., "Total chemical synthesis of enzymatically active human type II secretory phospholipase $A_2$," *Proc. Natl. Acad. Sci. USA*, 1997, 94:7845-7850.

Hamer et al., "Regulation in vivo of a cloned mammalian gene: cadmium induces the transcription of a mouse metallothionein gene in SV40 vectors," *J. Molec. Appl. Genet.*, 1982, 1:273-288.

Hamers-Casterman et al., "Naturally occurring antibodies devoid of light chains," *Nature*, 1993, 363:446-449.

Hansson et al., "An in vitro selected binding protein (affibody) shows conformation-dependent recognition of the respiratory syncytial virus (RSV) G protein," *Immunotechnology*, 1999, 4:237-252.

Harding and Lonberg, "Class switching in human immunoglobulin transgenic mice," *Ann. N.Y. Acad. Sci.*, 1995, 764:536-546.

Herschman, "The EGF receptor," in *Control of Animal Cell Proliferation*, 1985, vol. 1, Boynton et al., (eds.) pp. 169-199.

Hill-Perkins and Possee, "A baculovirus expression vector derived from the basic protein promoter of *Autographa californica* nuclear polyhedrosis virus," *J. Gen. Virol.*, 1990, 71:971-976.

Holliger et al., ""Diabodies": Small bivalent and bispecific antibody fragments," *Proc. Natl. Acad. Sci. USA*, 1993, 90: 6444-6448.

Hoogenboom and Winter, "By-passing immunisation—human antibodies from synthetic repertoires of germline $V_H$ gene segments rearranged in vitro," *J. Mol. Biol.*, 1991, 227:381-388.

Hopp et al., "A short polypeptide marker sequence useful for recombinant protein identification and purification," *Biotechnology*, 1988, 6:1204-1210.

Horisberger and Di Marco, "Interferon-alpha hybrids," *Pharmac. Ther.*, 1995, 66:507-534.

Horsch et al., "A simple and general method for transferring genes into plants," *Science*, 1985, 227:1229-1231.

Huston et al., "Protein engineering of antibody binding sites: recovery of specific activity in an anti-digoxin single-chain Fv analogue produced in *Escherichia coli*," *Proc. Natl. Acad. Sci. USA*, 1988, 85:5879-5883.

"IUPAC-IUB commission on biochemical nomenclature a one-leter notation for amino acid sequences[1-3] tentative rules," *J. Biol. Chem.*, 1969, 243:3557-3559.

Jakobovits et al., "Analysis of homozygous mutant chimeric mice: deletion of the immunoglobulin heavy-chain joining region blocks B-cell development and antibody production," *Proc. Natl. Acad. Sci. USA*, 1993, 90:2551-2555.

Jakobovits et al., "Germ-line transmission and expression of a human-derived yeast artificial chromosome," *Nature*, 1993, 362:255-258.

Jones et al., "Replacing the complementarity-determining regions in a human antibody with those from a mouse ," *Nature*, 1986, 321:522-525.

Karpovsky et al., "Production of target-specific effector cells using hetero-cross-linked aggregates containing anti-target cell and anti-Fc gamma receptor antibodies," *J. Exp. Med.*, 1984, 160:1686-1701.

Kaufman and Sharp, "Amplification and expression of sequences cotransfected with a modular dihydrofolate reductase complementary DNA gene," *Mol. Biol.*, 1982, 159:601-621.

Kaufman et al., "Improved vectors for stable expression of foreign genes in mammalian cells by use of the untranslated leader sequence from EMC virus," *Nucl. Acids Res.*, 1991, 19:4485-4490.

Klein et al., "Transformation of microbes, plants and animals by particle bombardment," *Biotechnology*, 1992, 10:268-291.

Kohler and Milstein, "Continuous cultures of fused cells secreting antibody of predefined specificity," *Nature*, 1975, 256:495-497.

Kozak, "Structural features in eukaryotic mRNAs that modulate the initiation of translation," *J. Biol. Chem.*, 1991, 266:19867-19870.

Kranz and Voss, "Restricted reassociation of heavy and light chains from hapten-specific monoclonal antibodies," *Proc. Natl. Acad. Sci. USA*, 1981, 78:5807-5811.

Kristensen and Winter, "Proteolytic selection for protein folding using filamentous bacteriophages," *Fold Des.*, 1998, 3(5):321-328.

Kristensen et al., "Amino acid sequence of human pregnancy-associated plasma protein-A derived from cloned cDNA," *Biochemistry*, 1994, 33:1592-1598.

Lane and Stephen, "Epitope mapping using bacteriophage peptide libraries," *Curr. Opin. Immunol.*, 1993, 5:268-271.

Lemaigre and Rousseau, "Transcriptional control of genes that regulate glycolysis and gluconeogenesis in adult liver," *Biochem. J.*, 1994, 303:1-14.

Liu et al., "Heteroantibody duplexes target cells for lysis by cytotoxic T lymphocytes ," *Proc. Natl. Acad. Sci. USA*, 1985, 82:8648-8652.

Livingstone & Barton, "Protein sequence alignments: a strategy for the hierarchical analysis of residue conservation," *CABIOS*, 1993, 9(6):745-756.

Loeken, "Effects of mutation of the CREB binding site of the somatostatin promoter on cyclic AMP responsiveness in CV-1 cells," *Gene Expr.*, 1993, 3:253-264.

Lonberg and Huszar, "Human antibodies from transgenic mice," *Intern. Rev. Immunol.*, 1995, 13:65-93.

Lonberg et al., "Antigen-specific human antibodies from mice comprising four distinct genetic modifications," *Nature*, 1994, 368:856-859.

Lonberg, "Transgenic approaches to human monoclonal antibodies," *Handbook of Experimental Pharmacology*, 2003, 113:49-101.

Lowman et al., "Selecting high-affinity binding proteins by monovalent phage display," *Biochem.*, 1991, 30(45):10832-10844.

Luckow et al., "Efficient generation of infectious recombinant baculoviruses by site-specific transposon-mediated insertion of foreign genes into a baculovirus genome propagated in *Escherichia coli*," *J. Virol.*, 1993, 67:4566-4579.

Luckow, "Insect cell expression technology," in *Protein Engineering: Principles and Practice*, 1996, Cleland et al. (eds.), pp. 183-218, John Wiley & Sons, Inc.

Luo et al., "A universal tag for recombinant proteins," *Arch. Biochem. Biophys.* 1996, 329:215-220.

Marks et al., "By-passing immunization: Human antibodies from V-gene libraries displayed on phage," *J. Mol. Biol.*, 1991, 222:581-597.

McGehee et al., "Differentiation-specific element: a cis-acting developmental switch required for the sustained transcriptional expression of the angiotensinogen gene during hormonal-induced differentiation of 3T3-L1 fibroblasts to adipocytes," *Mol. Endocrinol.*, 1993, 7:551-560.

McKnight, "Functional relationships between transcriptional control signals of the thymidine kinase gene of herpes simplex virus," *Cell*, 1982, 31:355-365.

Meisel and Lam, "The conserved ELK-homeodomain of KNOTTED-1 contains two regions that signal nuclear localization," *Plant Molec. Biol.*, 1996, 30:1-14.

Merrifield, "Solid phase peptide synthesis. I. The synthesis of a tetrapeptide," *Am. Chem. Soc.*, 1963, 85:2149-2154.

Miki et al., "Procedures for introducing foreign DNA into plants," in *Methods in Plant Molecular Biology and Biotechnology*, 1993, Glick et al. (eds.), pp. 67-88.

(56) References Cited

OTHER PUBLICATIONS

Mole, "Epitope mapping," in *Methods in Molecular Biology*, 1992, vol. 10, Manson (ed.), pp. 105-116.

Monteiro et al., "Molecular heterogeneity of Fc alpha receptors detected by receptor-specific monoclonal antibodies," *J. Immunol.*, 1992, 148:1764-1770.

Morganti et al., "Production and characterization of biologically active Ala-Ser-(His)$_6$-Ile-Glu-Gly-Arg-human prolactin (tag-hPRL) secreted in the periplasmic space of *Escherichia coli*," *Biotechnol. Appl. Biochem.*, 1996, 23:67-75.

Morrison et al., "Chimeric human antibody molecules: mouse antigen-binding domains with human constant region domains," *Proc. Natl. Acad. Sci. USA*, 1994, 81:6851-6855.

Morrison, "Transfectomas provide novel chimeric antibodies," *Science*, 1985, 229:1202-1207.

Morton et al., "Structure and function of human IgA Fc receptors (Fc alpha R)," *Critical Reviews in Immunology*, 1996, 16:423-440.

Muir et al, "Expressed protein ligation: A general method for protein engineering," *Proc. Natl. Acad. Sci. USA*, 1998, 95:6705-6710.

Needleman and Wunsch, "A general method applicable to the search for similarities in the amino acid sequence of two proteins," *J. Mol. Biol.*, 1970, 48:443-453.

Ner et al., "A simple and efficient procedure for generating random point mutations and for codon replacements using mixed oligodeoxynucleotides," *DNA*, 1988, 7:127-134.

Ng and Henikoff, "Predicting deleterious amino acid substitutions," *Genome Research*, 2001, 11(5):863-874.

Nilsson et al., "Expression and purification of recombinant insulin-like growth factors from *Escherichia coli*," *Methods Enzymol.*, 1991, 198:3-16.

Nilsson et al., "Immobilization and purification of enzymes with staphylococcal protein A gene fusion vectors," *EMBO J.*, 1985, 4:1075-1080.

O'Reilly et al., "Identification of an activating transcription factor (ATF) binding site in the human transforming growth factor-beta 2 promoter," *J. Biol. Chem.*, 1992, 267:19938-19943.

Pall and Brunelli, "A series of six compact fungal transformation vectors containing polylinkers with unique restrictions sites," *Fungal Genetics Newsletter*, 1993, 8 pages.

Patel and Jones, "The baculovirus expression system," in *DNA Cloning 2: Expression Systems*, 1995, 2nd Edition, Glover et al. (eds.), pp. 205-244.

Patel et al., "*Saccharomyces cerevisiae* expression vectors with thrombin-cleavable N- and C-terminal 6x(His) tags," *Biotechnology Letters*, 2003, 25(4):331-334.

Paulus, "Preparation and biomedical applications of bispecific antibodies," *Behring Inst. Mitt.*, 1985, 78:118-132.

Pearson and Lipman, "Improved tools for biological sequence comparison," *Proc. Natl. Acad. Sci. USA*, 1988, 85:2444-2448.

Pearson, "Rapid and sensitive sequence comparison with FASTP and FASTA," *Meth. Enzymol.*, 1990, 183:63-98.

Pollock et al., "Transgenic milk as a method for the production of recombinant antibodies," *J. Immunol.Meth.*, 1999, 231:147-157.

Price, "Production and characterization of synthetic peptide-derived antibodies," in *Monoclonal Antibodies: Production, Engineering, and Clinical Application*, 1995, Ritter and Ladyman (eds.), pp. 60-84.

Queen et al., "A humanized antibody that binds to the interleukin 2 receptor," *Proc. Natl. Acad. Sci. USA*, 1989, 86:10029-10033.

Raymond et al., "Development of the methylotrophic yeast *Pichia methanolica* for the expression of the 65 kilodalton isoform of human glutamate decarboxylase," *Yeast*, 1998, 14:11-23.

Reidhaar-Olson and Sauer, "Combinatorial cassette mutagenesis as a probe of the informational content of protein sequences," *Science*, 1988, 241:53-57.

Riechmann et al., "Reshaping human antibodies for therapy," *Nature*, 1998, 332:323-327.

Robertson et al., "A general and efficient route for chemical aminoacylation of transfer RNAs," *J. Am. Chem. Soc.*, 1991, 113:2722-2729.

Romanos et al., "Expression of Cloned Genes in Yeast," in *DNA Cloning 2: A Practical Approach*, 1995, 2.sup.nd Edition, Glover and Hames (eds.), pp. 123-167.

Ronnmark et al., "Construction and characterization of affibody-Fc chimeras produced in *Escherichia coli*," *J. Immunol. Methods.*, 2002, 261:199-211.

Sarnbrook et al., "Hybridization to nitrocellulose filters containing replicas of bacterial colonies," *Molecular Cloning, A Laboratory Manual*, 1989, Cold Spring Harbor, Laboratory Press, 1.101-1.104.

Sellers, "On the theory and computation of evolutionary distance," *SIAM J. Appl. Math.*, 1974, 26:787-793.

Severinov and Muir, "Expressed protein ligation, a novel method for studying protein-protein interactions in transcription," *J. Biol. Chem.*, 1998, 273(26):16205-16209.

Smith and Johnson, "Single-step purification of polypeptides expressed in *Escherichia coli* as fusions with glutathione S-transferase," *Gene*, 1988, 67:31-40.

Soe et al., "Expression of recombinant murine pregnancy-associated plasma protein-A (PAPP-A) and a novel variant (Papp-Ai) with differential proteolytic activity," *Eur. J. Biochem.*, 2002, 269(8):2247-2256.

Stemmer, "DNA shuffling by random fragmentation and reassembly: In vitro recombination for molecular evolution," *Proc. Natl. Acad. Sci. USA*, 1994, 91:10747-10751.

Stemmer, "Rapid evolution of a protein in vitro by DNA shuffling," *Nature*, 1994, 370:389-391.

Sulkowski, "Purification of proteins by IMAC," *Trends in Biochem.*, 1985, 3:1-7.

Sutcliffe et al., "Antibodies that react with predetermined sites on proteins," *Science*, 1983, 219:660-666.

Taylor et al., "A transgenic mouse that expresses a diversity of human sequence heavy and light chain immunoglobulins," *Nucleic Acids Research*, 1992, 20(23):6287-6295.

Taylor et al., "Human immunoglobulin transgenes undergo rearrangement, somatic mutation and class switching in mice that lack endogenous IgM," *International Immunology*, 1994, 6:579-591.

Treisman, "The SRE: a growth factor responsive transcriptional regulator," *Seminars in Cancer Biol.* 1990, 1:47-58.

Treuter et al., "Promoter specificity and deletion analysis of heat stress transcription factors of tomato," *Molec. Gen. Genet.*, 1993, 240:113-125.

Tuaillon et al., "Biased utilization of DHQ52 and JH4 gene segments in a human Ig transgenic minilocus is independent of antigenic selection," *J. Immunol.*, 1994, 152:2912-2920.

Tuaillon et al., "Human immunoglobulin heavy-chain minilocus recombination in transgenic mice: gene-segment use in mu and gamma transcripts," *Proc. Natl. Acad. Sci. USA*, 1993, 90:3720-3724.

Urlaub and Chasin, "Isolation of Chinese hamster cell mutants deficient in dihydrofolate reductase activity," *Proc. Natl. Acad. Sci. USA*, 1980, 77:4216-4220.

Urlaub et al., "Effect of gamma rays at the dihydrofolate reductase locus: deletions and inversions," *Som. Cell Mol. Genet.*, 1986, 12:555-566.

Vaughan, et al., "Human antibodies with sub-nanomolar affinities isolated from a large non-immunized phage display library," *Nature Biotech.*, 1996, 14:309-314.

Verma et al., "Antibody engineering: Comparison of bacterial, yeast, insect and mammalian expression systems," *J. Immunol Meth.*, 1998, 216:165-181.

Ward and Bebbington, "Genetic manipulation and expression of antibodies," in *Monoclonal Antibodies: Principles and Applications*, 1995, pp. 137-185.

Williams et al., "Expression of foreign proteins in *E. coli* using plasmid vectors and purification of specific polyclonal antibodies," in *DNA Cloning 2: A Practical Approach*, 1995, 2nd Edition, Glover and Hames (Eds.), pp. 15-58.

(56) References Cited

OTHER PUBLICATIONS

Wu et al. (eds.), "Information superhighway and computer databases of nucleic acids and proteins," in *Methods in Gene Biotechnology*, 1997, pp. 123-151, CRC Press, Inc.

Yamaguchi and Kuo, "Functional analysis of aryl hydrocarbon receptor nuclear translocator interactions with aryl hydrocarbon receptor in the yeast two-hybrid system," *Biochem. Pharmacol.*, 1996, 50:1295-1302.

Ye et al., "Characterization of a silencer regulatory element in the human interferon-gamma promoter," *J. Biol. Chem.*, 1994, 269(41):25728-25734.

Zheng et al., "A new expression vector for high level protein production, one step purification and direct isotopic labeling of calmodulin-binding peptide fusion proteins," *Gene*, 1997, 186:55-60.

Zhou et al., "Synthesis of functional mRNA in mammalian cells by bacteriophage T3 RNA polymerase," *Mol. Cell. Biol.*, 1990, 10:4529-4537.

SELECTIVE EXOSITE INHIBITION OF PAPP-A ACTIVITY AGAINST IGFBP-4

This application is a National Stage application under 35 U.S.C. 371 and claims benefit under 35 U.S.C. 119(a) of International Application No. PCT/EP2009/050796, having an International Filing Date of Jan. 23, 2009, which claims the benefit of U.S. provisional application Ser. No. 61/023,631, filed Jan. 25, 2008, U.S. provisional application Ser. No. 61/025,545 filed Feb. 1, 2008, and Danish Application Serial No. PA 2008 00148, filed Feb. 1, 2008, which are hereby incorporated by reference in their entirety.

FIELD OF INVENTION

The present invention relates to one or more protease inhibitors which cause general inhibition or differential inhibition of two or more physiological substrates of a protease by targeting one or more substrate binding exosite(s). In one embodiment, the present invention specifically relates to targeting of the exosite(s) in PAPP-A.

BACKGROUND OF INVENTION

The insulin-like growth factors (IGF-I and -II) are polypeptides of approximately 70-residues with auto- and paracrine effects on cell proliferation, migration and differentiation. The IGFs binds to the IGF-1 receptor (IGFR), but a series of six binding proteins, IGFBP-1 to –6, are able to sequester IGF from IGFR because of higher affinities for IGF-I and -II. However, bioactive IGF can be released from such complexes by means of proteolytic cleavage of the binding protein, causing the generation of IGFBP fragments with diminished affinity for IGF. Specific, limited proteolysis represents the principal mechanism of IGF activation.

Several lines of evidence have demonstrated that the metalloproteinase pregnancy-associated plasma protein-A (PAPP-A, pappalysin-1, EC 3.4.24.79) functions in the IGF system. PAPP-A specifically cleaves IGFBP-4 and IGFBP-5, thereby releasing sequestered IGF or causing binding protein inactivation. PAPP-A knockout mice are proportional dwarfs, reduced to a body mass of 60% compared to wild type littermates. This phenotype is similar to the phenotype of IGF-II knockout mice, supporting the hypothesis that IGF-II activity requires PAPP-An activity in early fetal development with cleavage of IGFBP-4 being responsible for the final delivery of IGF to the receptor. Postnatally, PAPP-A and IGFBP-4 appears to be implicated in many different processes of cell proliferation, such as wound healing, follicle selection, implantation, myoblast proliferation and differentiation, and bone formation in vivo. PAPP-A is produced by vascular smooth muscle cells following angioplasty, suggesting that it promotes neointimal cell proliferation, and it has been shown to be a serum marker of acute coronary syndromes, most likely because it is abundantly synthesized in unstable atherosclerotic plaques.

The 400 kDa PAPP-A has two subunits of 1547 residues, and it belongs to the metzincin superfamily of metalloproteinases. A laminin G-like module of unknown function is present N-terminal to the proteolytic domain, and five complement control protein (CCP) modules, enabling PAPP-A to bind to the cell surface, are located in the C-terminal end of the subunit (FIG. 1). Additionally, PAPP-A contains three Lin12-Notch repeat (LNR) modules, which are unique to PAPP-A, its homologue PAPP-A2, and the family of Notch receptors. In PAPP-A and PAPP-A2, two LNR modules (LNR1 and 2) are inserted into the proteolytic domain, whereas the third (LNR3) is located C-terminal to the CCP modules, (FIG. 1). Within the PAPP-A dimer, the LNR modules probably form trimeric units composed of LNR1 and 2 from one subunit and LNR3 from the other subunit. Compromised LNR functionality renders PAPP-A unable to cleave IGFBP-4, while cleavage of IGFBP-5 is unaffected.

The IGFs are involved in both normal physiology and human disease, e.g. cancer and cardiovascular disease, and therefore, strategies for the direct inhibition of IGF signalling are being developed. However, specific inhibition of growth promoting proteolytic activity may represent a valuable alternative, in particular because such inhibition of IGF receptor stimulation is unlikely to interfere with insulin signalling and other aspects of normal physiology.

The principle of exosite inhibition is highly relevant for many proteolytic enzymes involved in human disease, in particular multidomain enzymes such as the large group of matrix metalloproteinases (MMPs) and related enzymes. Inhibition by targeting a substrate binding exosite has at least two advantages compared to direct active site inhibition: specificity and selectivity. First, an inhibitor directed towards an exosite is less likely to influence the activity of other related proteinases with similar active site architecture. Second, cleavage of different substrates of a given proteinase may not use the same exosite and therefore can be differentially inhibited.

The literature contains many examples of proteolytic inhibition by exosite targeting. For example, MMP-2 cleavage of type I gelatin and type IV collagen has been inhibited by targeting the collagen binding domain using a synthetic peptide, and a substrate binding pocket distinct from the catalytic site of beta-APP cleaving enzyme has been targeted by synthetic peptides. Also, many exosite inhibitors have been developed towards the coagulation enzyme Factor VIIa, and although specific for this proteinase, all of its several biological substrates are targeted by such inhibitors. Therefore, to the best of our knowledge, the inhibition of IGFBP-4 proteolysis by PAPP-A represents the first example of selective inhibition of one natural proteinase substrate by exosite targeting.

SUMMARY OF INVENTION

The present invention relates in one embodiment to generation of antibodies such as monoclonal scFv antibodies which bind to a region comprising LNR3 of PAPP-A and efficiently inhibit proteolysis of IGFBP-4, and to a lesser extent IGFBP-5. The region comprising LNR3 represents a substrate binding exosite, which can be targeted for selective proteolytic inhibition. Accordingly, the present invention relates in one embodiment to differential inhibition of natural protease substrates by exosite targeting.

In another embodiment the present invention relates to a polypeptide comprising or consisting of any one of SEQ ID NO:1, SEQ ID NO:2 and SEQ ID NO:3, or a polypeptide fragment of any one of SEQ ID NO:1, SEQ ID NO:2 and SEQ ID NO:3, said polypeptide or fragment thereof being capable of binding a molecule thereby inhibiting the activity of the polypeptide or fragment thereof.

The present invention also relates to a polypeptide variant of SEQ ID NO:1, SEQ ID NO:2 and SEQ ID NO:3 having at least 70% sequence identity with SEQ ID NO:1, SEQ ID NO:2 and SEQ ID NO:3, or a polypeptide variant of a fragment of SEQ ID NO:1, SEQ ID NO:2 and SEQ ID NO:3.

The invention also relates to a molecule capable of interacting with the PAPP-A-derived polypeptides described above.

Another aspect of the invention relates to an antibody, or a binding fragment thereof, that specifically binds an amino acid sequence selected from the group consisting of SEQ ID NO:1, SEQ ID NO:2 or SEQ ID NO:3, or a naturally occurring variant thereof.

The invention also relates to an antibody comprising or consisting of SEQ ID NO:5 or SEQ ID NO:6, or a binding fragment of SEQ ID NO:5 or SEQ ID NO:6, said antibody or fragment thereof being capable of interacting with a PAPP-A exosite(s). The invention also relates to variants of SEQ ID NO:5 or SEQ ID NO:6.

Further, the invention also relates to an antibody comprising or consisting of SEQ ID NO:7, or a binding fragment of SEQ ID NO:7, said antibody or fragment thereof being capable of interacting with PAPP-A outside the exosite(s). The invention also relates to variants of SEQ ID NO:7.

Another preferred embodiment of the invention relates to a method for producing the polypeptide described above, said method comprising the steps of providing a polynucleotide encoding said polypeptide and expressing said polynucleotide either in vitro, or in vivo in a suitable host organism, thereby producing said polypeptide.

The present invention further relates to a polynucleotide encoding any of the polypeptide or variants thereof described above. In addition, the invention relates to a nucleotide sequence capable of hybridizing to the polynucleotide encoding the polypeptides described above or a fragment hereof, under stringent conditions. Furthermore, the invention relates to a nucleotide sequence according as described above, wherein the portion of said polynucleotide which encodes the polypeptide hybridizes under stringent conditions to a nucleotide probe corresponding to at least 10 consecutive nucleotides of a nucleotide sequence of SEQ ID NO:1, SEQ ID NO:2, SEQ ID NO:3, SEQ ID NO:4, SEQ ID NO:5, SEQ ID NO:6 and SEQ ID NO:7.

In another embodiment the invention relates to a fragment of PAPP-A comprising the exosite(s) SEQ ID NO:2.

In a further embodiment the present invention relates to a complex comprising a polypeptide sequence comprising a PAPP-A exosite(s) such as SEQ ID NO:1, SEQ ID NO:2 and/or SEQ ID NO:3 and a binding partner having an affinity for said exosite(s), wherein the binding of the binding partner to the exosite(s) alters the activity of PAPP-A.

In addition, the present invention relates to an expression vector comprising one or more of the polynucleotides described above, said polynucleotide being optionally linked to regulatory sequence controlling the expression of said polynucleotide in a suitable host cell.

Another aspect of the invention relates to an isolated recombinant or transgenic host cell comprising one or more of the polypeptides described above and/or the expression vector described above.

The present invention also relates to a method for generating a transgenic, mammalian host cell, said method comprising the steps of providing a polynucleotide encoding one or the polypeptides described above, introducing said polynucleotide into said recombinant or transgenic host cell and optionally also expressing said polynucleotide in said transgenic, mammalian host cell, thereby generating a transgenic, mammalian host cell producing said polypeptide.

Furthermore, the present invention relates to a recombinant bacterial host cell comprising one or more of the polypeptides described above and/or one or more of the polynucleotides described above and/or the vector described above.

The present invention also relates to a method for generating a recombinant bacterial cell, said method comprising the steps of providing one or more polynucleotides encoding one or more polypeptides described above, introducing said polynucleotide into said bacterial cell and optionally also expressing said polynucleotide in said bacterial cell, thereby generating a recombinant bacterial cell producing said polypeptide.

In yet another embodiment the invention relates to a recombinant yeast cell comprising one or more of the polypeptides described above and/or one or more of the polynucleotides described above and/or the vector described above.

The present invention also relates to a method for generating a recombinant or transgenic host cell, said method comprising the steps of providing one or more of the polynucleotides encoding one or more of the polypeptide described above, introducing said polynucleotide into said recombinant or transgenic host cell and optionally also expressing said polynucleotide in said recombinant or transgenic host cell, thereby generating a recombinant or transgenic host cell producing said polypeptide.

In another preferred embodiment the invention relates to a transgenic, mammalian organism comprising the host cell described above.

The invention further relates to a method for generating a recombinant yeast cell, said method comprising the steps of providing one or more polynucleotides encoding one or more of the polypeptides described above, introducing said polynucleotide into said yeast cell and optionally also expressing said polynucleotide in said yeast cell, thereby generating a recombinant yeast cell producing said polypeptide.

The present invention also relates to a recombinant fungal host cell comprising one or more of the polypeptides described above and/or one or more of the polynucleotides described above and/or the vector described above.

The invention also relates to a method for generating a recombinant fungal cell, said method comprising the steps of providing one or more of the polynucleotides encoding one or more of the polypeptides described above, introducing said polynucleotide into said fungal cell and optionally also expressing said polynucleotide in said fungal cell, thereby generating a recombinant bacterial cell producing said polypeptide.

In addition, the invention relates to a method for generating monoclonal phage-derived scFv antibodies specific for the exosite(s) in PAPP-A, said method comprising the steps of infecting *E. coli* with selected phages, inducing cultures to produce and purify expressed protein.

In another preferred embodiment the present invention relates to a method for generating a polyclonal antibody, or a binding fragment thereof specific for one or more of the polypeptides described above, said method comprising the steps of immunizing a mammalian subject with said polypeptide under conditions eliciting an antibody response, identifying an antibody which bind specifically to the polypeptide, and optionally isolating said antibody or binding fragment thereof from said mammalian subject.

The present invention also relates to a method for generating a monoclonal antibody specific for one or more of the polypeptide described above, said method comprising the steps of immunizing a mammalian subject with said under conditions eliciting an antibody response, preparing a hybridoma producing a monoclonal antibody specific for said polypeptide, and identifying an antibody which bind specifically to the polypeptide.

The invention further relates to a polypeptide capable of being recognized by the antibody described above.

In another preferred embodiment the present invention relates to a composition comprising one or more of the polypeptide described above in combination with a physiologically acceptable carrier.

In addition, the invention relates to a pharmaceutical composition comprising one or more of the polypeptide described above in combination with a pharmaceutically acceptable carrier and optionally one or more additional bioactive agent(s).

In addition, the invention relates to a pharmaceutical composition comprising one or more of the polypeptide described above in combination with one or more additional bioactive agent(s) selected from the group of anti-platelet agents, anti-coagulation agents, fibrinolytic agents, drugs for treatment of cardiovascular diseases, drugs for treatment of osteoporoses, and anti-cancer drugs for medical use.

The present invention also relates to a kit-of-parts comprising one or more of the polypeptides described above or the pharmaceutical composition described above, and at least an additional component such as for example drugs for treatment of one or more types of cancer, one or more type of cardiovascular diseases and osteoporosis.

The invention also relates to a method for identifying binding partners for one or more of the polypeptides described above, said method comprising the steps of extracting the polypeptide and isolating said binding partners.

In another embodiment the invention relates to one or more of the polypeptides described above or the pharmaceutical composition for use as a medicament.

The invention also relates to a method for treatment of an individual in need thereof with an exosite interactor such as PAPP-A exosite(s) interactor such as PAC1 and/or PAC2 to inhibit proteolysis of one or more of PAPP-A's substrates.

The present invention further relates to exosite interactors that cause general inhibition of one or more physiological substrates of the proteinase comprising the exosite by targeting a substrate binding exosite.

The present invention also relates to exosite interactors that cause differential inhibition of two or more physiological substrates of the proteinase comprising the exosite by targeting a substrate binding exosite.

DEFINITIONS/ABBREVIATIONS

PAPP-A: pregnancy-associated plasma protein-A. All disclosures of PAPP-A in the present document also relate to any of the PAPP-A variant described in this document.

PAC1: PAPP-A exosite antibody. All disclosures of PAC1 in the present document also relate to any of the PAC1 variants described in this document.

PAC2: PAPP-A exosite antibody. All disclosures of PAC2 in the present document also relate to any of the PAC2 variants described in this document.

PAC5: PAPP-A non-exosite antibody. All disclosures of PAC5 in the present document also relate to any of the PAC5 variants described in this document.

The terms "treating", "treatment" and "therapy" as used herein refer equally to curative therapy, prophylactic or preventative therapy and ameliorating therapy. The term includes an approach for obtaining beneficial or desired physiological results, which may be established clinically. For purposes of this invention, beneficial or desired clinical results include, but are not limited to, alleviation of symptoms, diminishment of extent of disease, stabilized (i.e., not worsening) condition, delay or slowing of progression or worsening of condition/symptoms, amelioration or palliation of the condition or symptoms, and remission (whether partial or total), whether detectable or undetectable. The term "palliation", and variations thereof, as used herein, means that the extent and/or undesirable manifestations of a physiological condition or symptom are lessened and/or time course of the progression is slowed or lengthened, as compared to not administering compositions of the present invention.

The term "secondary prophylaxis" refer to prophylactic therapy after the first occurrence of a pathological condition, such as myocardial infarction, ischemic stroke, angina pectoris and peripheral arterial disease.

A "treatment effect" or "therapeutic effect" is manifested if there is a change in the condition being treated, as measured by the criteria constituting the definition of the terms "treating" and "treatment." There is a "change" in the condition being treated if there is at least 5% improvement, preferably 10% improvement, more preferably at least 25%, even more preferably at least 50%, such as at least 75%, and most preferably at least 100% improvement. The change can be based on improvements in the severity of the treated condition in an individual, or on a difference in the frequency of improved conditions in populations of individuals with and without treatment with the bioactive agent, or with the bioactive agent in combination with a pharmaceutical composition of the present invention.

"Pharmacologically effective amount", "pharmaceutically effective amount" or "physiologically effective amount of a "bioactive agent" is the amount of an active agent present in a pharmaceutical composition as described herein that is needed to provide a desired level of active agent in the bloodstream or at the site of action in an individual (e.g., the lungs, the gastric system, the colorectal system, prostate, etc.) to be treated to give an anticipated physiological response when such composition is administered. The precise amount will depend upon numerous factors, e.g., the active agent, the activity of the composition, the delivery device employed, the physical characteristics of the composition, intended patient use (i.e., the number of doses administered per day), patient considerations, and the like, and can readily be determined by one skilled in the art, based upon the information provided herein. An "effective amount" of a bioactive agent can be administered in one administration, or through multiple administrations of an amount that total an effective amount, preferably within a 24-hour period. It can be determined using standard clinical procedures for determining appropriate amounts and timing of administration. It is understood that the "effective amount" can be the result of empirical and/or individualized (case-by-case) determination on the part of the treating health care professional and/or individual.

The terms "enhancing" and "improving" a beneficial effect, and variations thereof, as used herein, refers to the therapeutic effect of the bioactive agent against placebo, or an increase in the therapeutic effect of a state-of-the-art medical treatment above that normally obtained when a pharmaceutical composition is administered without the bioactive agent of this invention. "An increase in the therapeutic effects" is manifested when there is an acceleration and/or increase in intensity and/or extent of the therapeutic effects obtained as a result of administering the bioactive agent(s). It also includes extension of the longevity of therapeutic benefits. It can also manifest where a lower amount of the pharmaceutical composition is required to obtain the same benefits and/or effects when it is co-administered with bioactive agent(s) provided by the present invention as compared to the administration in a higher amount of the pharmaceutical composition in the absence of bioactive agent. The enhancing effect preferably, but not necessarily, results in treatment of acute symptoms for which the pharmaceutical composition alone is not effective or is less effective therapeutically. Enhancement is achieved when there is at least a 5% increase in the therapeutic effects, such as at least 10% increase in the therapeutic effects when a bioactive agent of the present invention is co-administered with a pharmaceutical composition compared with administration of the pharmaceutical composition alone. Preferably the increase is at least 25%, more preferably at least 50%, even more preferably at least 75%, most preferably at least 100%.

"Co-administering" or "co-administration" of bioactive agent(s), or bioactive agents and state-of-the-art medicaments, as used herein, refers to the administration of one or more bioactive agents of the present invention, or administration of one or more bioactive agents of the present invention and a state-of-the-art pharmaceutical composition within a certain time period. The time period is preferably less than 72 hours, such as 48 hours, for example less than 24 hours, such as less than 12 hours, for example less than 6 hours, such as less than 3 hours. However, these terms also mean that the bioactive agent and a therapeutic composition can be administered together.

The term "Individual" refers to vertebrates, particular members of the mammalian species, and includes, but is not limited to domestic animals, such as cattle, horses, pigs, sheep, mink, dogs, cats, mice, guinea pigs, rabbits, rats; sports animals, such as horses, poly ponies, dogs, camels, and primates, including humans.

A "polypeptide" is a polymer of amino acid residues preferably joined exclusively by peptide bonds, whether produced naturally or synthetically. A polypeptide produced by expression of a non-host DNA molecule is a "heterologous" peptide or polypeptide. The term "polypeptide" as used herein covers proteins, peptides and polypeptides, wherein said proteins, peptides or polypeptides may or may not have been post-translationally modified. Post-translational modification may for example be phosphorylation, methylation and glucosylation.

The term osteoporosis as used herein refers to a condition that features loss of the normal bone density and elasticity leading to fragile bones.

The term "homolog to e.g. SEQ ID NO:1" refers to a polypeptide with a sequence similar to but unlike e.g. SEQ ID NO:1, in that it is a polypeptide comprising or consisting of e.g. SEQ ID NO:1 or a fragment hereof.

The term "variant of e.g. SEQ ID NO:1" refers to a polypeptide with a sequence similar to but unlike e.g. SEQ ID NO:1, in that it is a polypeptide variant of e.g. SEQ ID NO:1 or a fragment hereof. The variant polypeptide has an amino acid sequence that is a modification of the polypeptide according to the present invention. The modification includes one or more conservative substitution(s) or one or more equivalent substitution(s) of one or more amino acids that alters the sequence, but not the biological activity, of the polypeptide of e.g. SEQ ID NO:1.

The present invention also relates to variants of the polypeptides SEQ ID NO:1, SEQ ID NO:2, SEQ ID NO:3, SEQ ID NO:4, SEQ ID NO:5, SEQ ID NO:6 and SEQ ID NO:7, or fragments thereof, wherein the substitutions have been designed by computational analysis that uses sequence homology to predict whether a substitution affects protein function (e.g. Pauline C. Ng and Steven Henikoff, Genome Research, Vol. 11, Issue 5, 863-874, May 2001).

An "isolated polypeptide" is a polypeptide that is essentially free from contaminating cellular components, such as carbohydrate, lipid, or other proteinaceous impurities associated with the polypeptide in nature. Typically, a preparation of isolated polypeptide contains the polypeptide in a highly purified form, i.e., at least about 80% pure, at least about 90% pure, at least about 95% pure, greater than 95% pure, or greater than 99% pure. One way to show that a particular protein preparation contains an isolated polypeptide is by the appearance of a single band following sodium dodecyl sulfate (SDS)-polyacrylamide gel electrophoresis of the protein preparation and Coomassie Brilliant Blue staining of the gel. However, the term "isolated" does not exclude the presence of the same polypeptide in alternative physical forms, such as dimers or alternatively glycosylated or derivatized forms.

The term "ortholog" denotes a polypeptide or protein obtained from one species that is the functional counterpart of a polypeptide or protein from a different species. Sequence differences among orthologs are the result of speciation.

"Paralogs" are distinct but structurally related proteins made by an organism. Paralogs are believed to arise through gene duplication. For example, alpha-globin, beta-globin, and myoglobin are paralogs of each other.

As used herein, "nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., (alpha-enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide nucleic acids," which comprise naturally-occurring or modified nucleic acid bases attached to a polyamide backbone. Nucleic acids can be either single stranded or double stranded.

The term "natural nucleotide" refers to any of the four deoxyribonucleotides, dA, dG, dT, and dC (constituents of DNA), and the four ribonucleotides, A, G, U, and C (constituents of RNA) are the natural nucleotides. Each natural nucleotide comprises or essentially consists of a sugar moiety (ribose or deoxyribose), a phosphate moiety, and a natural/standard base moiety. Natural nucleotides bind to complementary nucleotides according to well-known rules of base pairing (Watson and Crick), where adenine (A) pairs with thymine (T) or uracil (U); and where guanine (G) pairs with cytosine (C), wherein corresponding base-pairs are part of complementary, anti-parallel nucleotide strands. The base pairing results in a specific hybridization between predetermined and complementary nucleotides. The base pairing is the basis by which enzymes are able to catalyze the synthesis of an oligonucleotide complementary to the template oligonucleotide. In this synthesis, building blocks (normally the triphosphates of ribo or deoxyribo derivatives of A, T, U, C, or G) are directed by a template oligonucleotide to form a complementary oligonucleotide with the correct, complementary sequence. The recognition of an oligonucleotide sequence by its complementary sequence is mediated by corresponding and interacting bases forming base pairs. In nature, the specific interactions leading to base pairing are governed by the size of the bases and the pattern of hydrogen bond donors and acceptors of the bases. A large purine base (A or G) pairs with a small pyrimidine base (T, U or C). Additionally, base pair recognition between bases is influenced by hydrogen bonds formed between the bases. In the geometry of the Watson-Crick base pair, a six membered ring (a pyrimidine in natural oligonucleotides) is juxtaposed to a ring system composed of a fused, six membered ring and a five membered ring (a purine in natural oligonucleotides), with a middle hydrogen bond linking two ring atoms, and hydrogen bonds on either side joining functional groups appended to each of the rings, with donor groups paired with acceptor groups.

A "polynucleotide according to the present invention" or a "nucleic acid according to the present invention" is any polynucleotide encoding a "polypeptide according to the present invention", including any polypeptide cited in the claims of the present patent application or the patent granted on the basis of claims of this patent application.

The term "complement of a nucleic acid molecule" refers to a nucleic acid molecule having a complementary nucleotide sequence and reverse orientation as compared to a reference nucleotide sequence. For example, the sequence 5' ATGCACGGG 3' is complementary to 5' CCCGTGCAT 3'.

The term "degenerate nucleotide sequence" denotes a sequence of nucleotides that includes one or more degenerate codons as compared to a reference nucleic acid molecule that encodes a polypeptide. Degenerate codons contain different triplets of nucleotides, but encode the same amino acid residue (i.e., GAU and GAC triplets each encode Asp).

The term "structural gene" refers to a nucleic acid molecule that is transcribed into messenger RNA (mRNA), which is then translated into a sequence of amino acids characteristic of a specific polypeptide.

An "isolated nucleic acid molecule" is a nucleic acid molecule that is not integrated in the genomic DNA of an organism. For example, a DNA molecule that encodes a growth factor that has been separated from the genomic DNA of a cell is an isolated DNA molecule. Another example of an isolated nucleic acid molecule is a chemically-synthesized nucleic acid molecule that is not integrated in the genome of an organism. A nucleic acid molecule that has been isolated from a particular species is smaller than the complete DNA molecule of a chromosome from that species.

A "nucleic acid molecule construct" is a nucleic acid molecule, either single- or double-stranded, that has been modified through human intervention to contain segments of nucleic acid combined and juxtaposed in an arrangement not existing in nature.

"Linear DNA" denotes non-circular DNA molecules having free 5' and 3' ends. Linear DNA can be prepared from closed circular DNA molecules, such as plasmids, by enzymatic digestion or physical disruption.

"Complementary DNA (cDNA)" is a single-stranded DNA molecule that is formed from an mRNA template by the enzyme reverse transcriptase. Typically, a primer complementary to portions of mRNA is employed for the initiation of reverse transcription. Those skilled in the art also use the term "cDNA" to refer to a double-stranded DNA molecule consisting of such a single-stranded DNA molecule and its complementary DNA strand. The term "cDNA" also refers to a clone of a cDNA molecule synthesized from an RNA template.

A "promoter" is a nucleotide sequence that directs the transcription of a structural gene. Typically, a promoter is located in the 5' non-coding region of a gene, proximal to the transcriptional start site of a structural gene. Sequence elements within promoters that function in the initiation of transcription are often characterized by consensus nucleotide sequences. These promoter elements include RNA polymerase binding sites, TATA sequences, CAAT sequences, differentiation-specific elements (DSEs; McGehee et al., Mol. Endocrinol. 7:551 (1993)), cyclic AMP response elements (CREs), serum response elements (SREs; Treisman, Seminars in Cancer Biol. 1:47 (1990)), glucocorticoid response elements (GREs), and binding sites for other transcription factors, such as CRE/ATF (O'Reilly et al., J. Biol. Chem. 267:19938 (1992)), AP2 (Ye et al., J. Biol. Chem. 269:25728 (1994)), SP1, cAMP response element binding protein (CREB; Loeken, Gene Expr. 3:253 (1993)) and octamer factors (see, in general, Watson et al., eds., Molecular Biology of the Gene, 4th ed. (The Benjamin/Cummings Publishing Company, Inc. 1987), and Lemaigre and Rousseau, Biochem. J. 303:1 (1994)). If a promoter is an inducible promoter, then the rate of transcription increases in response to an inducing agent. In contrast, the rate of transcription is not regulated by an inducing agent if the promoter is a constitutive promoter. Repressible promoters are also known.

A "core promoter" contains essential nucleotide sequences for promoter function, including the TATA box and start of transcription. By this definition, a core promoter may or may not have detectable activity in the absence of specific sequences that may enhance the activity or confer tissue specific activity.

A "regulatory element" is a nucleotide sequence that modulates the activity of a core promoter. For example, a regulatory element may contain a nucleotide sequence that binds with cellular factors enabling transcription exclusively or preferentially in particular cells, tissues, or organelles. These types of regulatory elements are normally associated with genes that are expressed in a "cell-specific," "tissue-specific," or "organelle-specific" manner.

An "enhancer" is a type of regulatory element that can increase the efficiency of transcription, regardless of the distance or orientation of the enhancer relative to the start site of transcription.

"Heterologous DNA" refers to a DNA molecule, or a population of DNA molecules, that does not exist naturally within a given host cell. DNA molecules heterologous to a particular host cell may contain DNA derived from the host cell species (i.e., endogenous DNA) so long as that host DNA is combined with non-host DNA (i.e., exogenous DNA). For example, a DNA molecule containing a non-host DNA segment encoding a polypeptide linked to a host DNA segment comprising a transcription promoter is considered to be a heterologous DNA molecule. Conversely, a heterologous DNA molecule can comprise an endogenous gene linked with an exogenous promoter. As another illustration, a DNA molecule comprising a gene derived from a wild-type cell is considered to be heterologous DNA if that DNA molecule is introduced into a mutant cell that lacks the wild-type gene.

An "integrated genetic element" is a segment of DNA that has been incorporated into a chromosome of a host cell after that element is introduced into the cell through human manipulation. Within the present invention, integrated genetic elements are most commonly derived from linearized plasmids that are introduced into the cells by electroporation or other techniques. Integrated genetic elements are passed from the original host cell to its progeny.

A "cloning vector" is a nucleic acid molecule, such as a plasmid, cosmid, or bacteriophage that has the capability of replicating autonomously in a host cell. Cloning vectors typically contain one or a small number of restriction endonuclease recognition sites that allow insertion of a nucleic acid molecule in a determinable fashion without loss of an essential biological function of the vector, as well as nucleotide sequences encoding a marker gene that is suitable for use in the identification and selection of cells transformed with the cloning vector. Marker genes typically include genes that provide tetracycline resistance or ampicillin resistance.

An "expression vector" is a nucleic acid molecule encoding a gene that is expressed in a host cell. Typically, an expression vector comprises a transcription promoter, a gene, and a transcription terminator. Gene expression is usually placed under the control of a promoter, and such a gene is said to be "operably linked to" the promoter. Similarly, a regulatory element and a core promoter are operably linked if the regulatory element modulates the activity of the core promoter.

A "recombinant host" is a cell that contains a heterologous nucleic acid molecule, such as a cloning vector or expression vector.

"Integrative transformants" are recombinant host cells, in which heterologous DNA has become integrated into the genomic DNA of the cells.

The term "secretory signal sequence" denotes a DNA sequence that encodes a peptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a polypeptide encoded by a splice variant of an mRNA transcribed from a gene.

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of less than $10^9$ $M^{-1}$.

The term "hybridization under stringent conditions" is defined according to Sambrook et al., Molecular Cloning, A Laboratory Manual, Cold Spring Harbor, Laboratory Press (1989), 1.101-1.104. Preferably, hybridization under stringent conditions means that after washing for 1 h with 1 times SSC and 0.1% SDS at 50 degree C., preferably at 55 degree C., more preferably at 62 degree C. and most preferably at 68 degree C., particularly for 1 h in 0.2 times SSC and 0.1% SDS at 50 degree C., preferably at 55 degree C., more preferably at 62 degree C. and most preferably at 68 degree C., a positive hybridization signal is observed. A nucleotide sequence which hybridizes under the above washing conditions with the nucleotide sequence of e.g. SEQ ID NO:1 or a nucleotide sequence corresponding thereto in the scope of the degeneracy of the genetic code is encompassed by the present invention.

The term "antibody" as referred to herein includes whole antibodies and any antigen binding fragment (i.e., "antigen-binding portion") or single chain thereof. An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region (abbreviated herein as $C_H$). Each light chain is comprised of a light chain variable region (abbreviated herein as $V_L$) and a light chain constant region (abbreviated herein as $C_L$). The $V_H$ and $V_L$ regions can be further subdivided into regions of hypervariability, termed "complementarity determining regions" (CDRs), interspersed with regions that are more conserved, termed "framework regions" (FRs). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antigen-binding portion" of an antibody, as used herein, refers to one or more fragments of an antibody that retain the ability to specifically bind to an antigen. It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment, which consists of a $V_H$ domain; (vi) an isolated complementarity determining region (CDR), and (vii) a combination of two or more isolated CDRs which may optionally be joined by a synthetic linker. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. A further example is binding-domain immunoglobulin fusion proteins comprising (i) a binding domain polypeptide that is fused to an immunoglobulin hinge region polypeptide, (ii) an immunoglobulin heavy chain CH2 constant region fused to the hinge region, and (iii) an immunoglobulin heavy chain CH3 constant region fused to the CH2 constant region. The binding domain polypeptide can be a heavy chain variable region or a light chain variable region. These antibody fragments are obtained using conventional techniques known to those with skill in the art, and the fragments are screened for utility in the same manner as are intact antibodies.

An "antibody fragment" is a portion of an antibody such as F(ab')$_2$, F(ab)$_2$, Fab', Fab, and the like. Regardless of structure, an antibody fragment binds with the same antigen that is recognized by the intact antibody. For example, an anti-(polypeptide according to the present invention) monoclonal antibody fragment binds an epitope of a polypeptide according to the present invention. The term "antibody fragment" also includes a synthetic or a genetically engineered polypeptide that binds to a specific antigen, such as polypeptides consisting of the light chain variable region, "Fv" fragments consisting of the variable regions of the heavy and light chains, recombinant single chain polypeptide molecules in which light and heavy variable regions are connected by a peptide linker ("scFv proteins"), and minimal recognition units consisting of the amino acid residues that mimic the hypervariable region.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents.

The term "discontinuous epitope", as used herein, means a conformational epitope on a protein antigen which is formed from at least two separate regions in the primary sequence of the protein.

A "detectable label" is a molecule or atom which can be conjugated to an antibody moiety to produce a molecule useful for diagnosis. Examples of detectable labels include chelators, photoactive agents, radioisotopes, fluorescent agents, paramagnetic ions, or other marker moieties.

A "naked antibody" is an entire antibody, as opposed to an antibody fragment, which is not conjugated with a therapeutic agent. Naked antibodies include both polyclonal and monoclonal antibodies, as well as certain recombinant antibodies, such as chimeric and humanized antibodies.

As used herein, the term "antibody component" includes both an entire antibody and an antibody fragment.

CDR (complementarity determining region): A complementarity determining region is a short amino acid sequence found in the variable domains of antigen receptor (e.g. immunoglobulin/antibody and T cell receptor) proteins that complements an antigen and therefore provides the receptor with its specificity for that particular antigen. Since most sequence variation associated with immunoglobulins and T cell receptors are found in the CDRs, these regions are sometimes referred to as hypervariable domains.

The term "inhibition" as used herein can be either full inhibition or partial inhibition. "Full inhibition" as used herein refers to complete or almost complete inhibition such as more than 90% inhibition. "Partial inhibition" refers less an inhibition than is not complete such as less than 90%.

A "target polypeptide" or a "target peptide" is an amino acid sequence that comprises at least one epitope, and that is expressed on a target cell, such as a tumor cell, or a cell that carries an infectious agent antigen. T cells recognize peptide epitopes presented by a major histocompatibility complex molecule to a target polypeptide or target peptide and typically lyse the target cell or recruit other immune cells to the site of the target cell, thereby killing the target cell.

An "antigenic peptide" is a peptide, which will bind a major histocompatibility complex molecule to form an MHC-peptide complex which is recognized by a T cell, thereby inducing a cytotoxic lymphocyte response upon presentation to the T cell. Thus, antigenic peptides are capable of binding to an appropriate major histocompatibility complex molecule and inducing a cytotoxic T cells response, such as cell lysis or specific cytokine release against the target cell which binds or expresses the antigen. The antigenic peptide can be bound in the context of a class I or class II major histocompatibility complex molecule, on an antigen presenting cell or on a target cell.

An "anti-idiotype antibody" is an antibody that binds with the variable region domain of an immunoglobulin. In the present context, an anti-idiotype antibody binds with the variable region of an anti-antibody, and thus, an anti-idiotype antibody mimics an epitope of a polypeptide according to the present invention.

The term "bispecific molecule" is intended to include any agent, e.g., a protein, peptide, or protein or peptide complex, which has two different binding specificities. For example, the molecule may bind to, or interact with, (a) a cell surface antigen and (b) an Fc receptor on the surface of an effector cell. The term "multispecific molecule" or "heterospecific molecule" is intended to include any agent, e.g., a protein, peptide, or protein or peptide complex, which has more than two different binding specificities. For example, the molecule may bind to, or interact with, (a) a cell surface antigen, (b) an Fc receptor on the surface of an effector cell, and (c) at least one other component. Accordingly, the invention includes, but is not limited to, bispecific, trispecific, tetraspecific, and other multispecific molecules which are directed to PAPP-A, and to other cell surface antigens or targets, such as Fc receptors on effector cells.

As used herein, a human antibody is "derived from" a particular germline sequence if the antibody is obtained from a system using human immunoglobulin sequences, e.g., by immunizing a transgenic mouse carrying human immunoglobulin genes or by screening a human immunoglobulin gene library, and wherein the selected human antibody is at least 90%, more preferably at least 95%, even more preferably at least 96%, 97%, 98%, or 99% identical in amino acid sequence to the amino acid sequence encoded by the germline immunoglobulin gene. Typically, a human antibody derived from a particular human germline sequence will display no more than 10 amino acid differences, more preferably, no more than 5, or even more preferably, no more than 4, 3, 2, or 1 amino acid difference from the amino acid sequence encoded by the germline immunoglobulin gene.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

"Humanized antibodies" are recombinant proteins in which murine complementarity determining regions of a monoclonal antibody have been transferred from heavy and light variable chains of the murine immunoglobulin into a human variable domain.

The term "recombinant human antibody", as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further in Section I, below), (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable and constant regions derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

As used herein, a "heterologous antibody" is defined in relation to the transgenic non-human organism producing such an antibody. This term refers to an antibody having an amino acid sequence or an encoding nucleic acid sequence corresponding to that found in an organism not consisting of the transgenic non-human animal, and generally from a species other than that of the transgenic non-human animal.

An "isolated antibody", as used herein, is intended to refer to an antibody which is substantially free of other antibodies having different antigenic specificities (e.g., an isolated antibody that specifically binds to PAPP-A is substantially free of antibodies that specifically bind antigens other than PAPP-A). An isolated antibody that specifically binds to an epitope, isoform or variant of human PAPP-A may, however, have cross-reactivity to other related antigens, e.g., from other species (e.g., PAPP-A species homologs). Moreover, an isolated antibody may be substantially free of other cellular material and/or chemicals. In one embodiment of the invention, a combination of "isolated" monoclonal antibodies having different specificities are combined in a well defined composition.

As used herein, "specific binding" refers to antibody binding to a predetermined antigen. Typically, the antibody binds with an affinity corresponding to a $K_D$ of about $10^{-7}$ M or less, such as about $10^{-8}$ M or less, such as about $10^{-9}$ M or less, about $10^{-10}$ M or less, or about $10^{-11}$ M or even less, when measured as apparent affinities based on $IC_{50}$ values in FACS, and binds to the predetermined antigen with an affinity corresponding to a $K_D$ that is at least ten-fold lower, such as at least 100-fold lower than its affinity for binding to a non-specific antigen (e.g., BSA, casein) other than the predetermined antigen or a closely-related antigen.

Affinity: the strength of binding between receptors and their ligands, for example between an antibody and its antigen.

Avidity: The functional combining strength of an antibody with its antigen which is related to both the affinity of the reaction between the epitopes and paratopes, and the valencies of the antibody and antigen Antibody Classes: Depending on the amino acid sequences of the constant domain of their heavy chains, immunoglobulins can be assigned to different classes. There are at least five (5) major classes of immunoglobulins: IgA, IgD, IgE, IgG and IgM, and several of these may be further divided into subclasses (isotypes), e.g. IgG-1, IgG-2, IgG-3 and IgG-4; IgA-1 and IgA-2. The heavy chains constant domains that correspond to the different classes of immunoglobulins are called alpha (α), delta (δ), epsilon (ε), gamma (γ) and mu (μ), respectively. The light chains of antibodies can be assigned to one of two clearly distinct types, called kappa (κ) and lambda (λ), based on the amino sequences of their constant domain. The subunit structures and three-dimensional configurations of different classes of immunoglobulins are well known.

Antibody Combining Site: An antibody combining site is that structural portion of an antibody molecule comprised of a heavy and light chain variable and hypervariable regions that specifically binds (immunoreacts with) an antigen. The term immunoreact in its various forms means specific binding between an antigenic determinant-containing molecule and a molecule containing an antibody combining site such as a whole antibody molecule or a portion thereof. Alternatively, an antibody combining site is known as an antigen binding site.

Chimeric antibody: An antibody in which the variable regions are from one species of animal and the constant regions are from another species of animal. For example, a chimeric antibody can be an antibody having variable regions which derive from a mouse monoclonal antibody and constant regions which are human.

Complementarity determining region or CDR: Regions in the V-domains of an antibody that together form the antibody recognizing and binding domain.

Constant Region or constant domain or C-domain: Constant regions are those structural portions of an antibody molecule comprising amino acid residue sequences within a given isotype which may contain conservative substitutions therein. Exemplary heavy chain immunoglobulin constant regions are those portions of an immunoglobulin molecule known in the art as CH1, CH2, CH3, CH4 and CH5. An exemplary light chain immunoglobulin constant region is that portion of an immunoglobulin molecule known in the art as $C_L$.

Diabodies: This term refers to a small antibody fragments with two antigen-binding sites, which fragments comprise a heavy chain variable domain (VH) connected to a light chain variable domain (VL) in the same polypeptide chain (VH-VL). By using a linker that is too short to allow pairing between the two domains on the same chain, the domains are forced to pair with the complementary domains of another chain and create two antigen-binding sites.

Fv: dual chain antibody fragment containing both a $V_H$ and a $V_L$.

Human antibody framework: A molecule having an antigen binding site and essentially all remaining immunoglobulin-derived parts of the molecule derived from a human immunoglobulin.

Humanised antibody framework: A molecule having an antigen binding site derived from an immunoglobulin from a non-human species, whereas some or all of the remaining immunoglobulin-derived parts of the molecule is derived from a human immunoglobulin. The antigen binding site may comprise: either a complete variable domain from the non-human immunoglobulin fused onto one or more human constant domains; or one or more of the complementarity determining regions (CDRs) grafted onto appropriate human framework regions in the variable domain. In a humanized antibody, the CDRs can be from a mouse monoclonal antibody and the other regions of the antibody are human.

Affibody: A recombinant immunologically active molecule, selected from a library constructed by combinatorial variegation of the Fc binding surface of a protein that is not an antibody, preferably the 58 residue staphylococcal protein A (SPA).

Immunoglobulin: The serum antibodies, including IgG, IgM, IgA, IgE and IgD.

Immunoglobulin isotypes: The names given to the Ig which have different H chains, the names are IgG (IgG$_{1,2,3,4}$), IgM, IgA (IgA$_{1,2}$), sIgA, IgE, IgD.

The phrase "immunologically distinct" refers to the ability to distinguish between two polypeptides on the ability of an antibody to specifically bind one of the polypeptides and not specifically bind the other polypeptide.

The phrase "monoclonal antibody" in its various grammatical forms refers to a population of antibody molecules that contains only one species of antibody combining site capable of immunoreacting with a particular antigen. A monoclonal antibody thus typically displays a single binding affinity for any antigen with which it immunoreacts. A monoclonal antibody may contain an antibody molecule having a plurality of antibody combining sites, each immunospecific for a different antigen, e.g., a bispecific monoclonal antibody.

"Polyclonal antibodies" are a mixture of antibody molecules recognising a specific given antigen, hence polyclonal antibodies may recognise different epitopes within said antigen.

Single Chain Antibody, or scFv, refers to a single polypeptide comprising one or more antigen binding sites. Furthermore, although the H and L chains of an Fv fragment are encoded by separate genes, they may be linked either directly or via a peptide, for example a synthetic linker can be made that enables them to be made as a single protein chain (known as single chain antibody, sAb; Bird et al. 1988 Science 242: 423-426; and Huston et al. 1988 PNAS 85:5879-5883) by recombinant methods. Such single chain antibodies are also encompassed within the term "antibody", and may be utilized as binding determinants in the design and engineering of a multispecific binding molecule.

Valency: The term valency refers to the number of potential antigen binding sites, i.e. binding domains, in a polypeptide. A polypeptide may be monovalent and contain one antigen binding site or a polypeptide may be bivalent and contain two antigen binding sites. Additionally, a polypeptide may be tetravalent and contain four antigen binding sites. Each antigen binding site specifically binds one antigen. When a polypeptide comprises more than one antigen binding site, each antigen binding site may specifically bind the same or different antigens. Thus, a polypeptide may contain a plurality of antigen binding sites and therefore be multivalent and a polypeptide may specifically bind the same or different antigens.

V-domain: Variable domains are those structural portions of an antibody molecule comprising amino acid residue sequences forming the antigen binding sites. An exemplary light chain immunoglobulin variable region is that portion of an immunoglobulin molecule known in the art as V$_L$.

V$_L$: Variable domain of the light chain.

V$_H$: Variable domain of the heavy chain.

The term "variant gene" refers to nucleic acid molecules that encode a polypeptide having an amino acid sequence that is a modification of a polypeptide according to the present invention. Such variants include naturally-occurring polymorphisms of genes according to the present invention, as well as synthetic genes that contain conservative amino acid substitutions of the amino acid sequence of a polypeptide according to the present invention. Additional variant forms of genes are nucleic acid molecules that contain insertions or deletions of the nucleotide sequences described herein. A variant gene according to the present invention can be identified by determining whether the gene hybridizes with a nucleic acid molecule having the nucleotide sequence of a polypeptide according to the present invention, or its complement, under stringent conditions.

Alternatively, variant genes can be identified by sequence comparison. Two amino acid sequences have "100% amino acid sequence identity" if the amino acid residues of the two amino acid sequences are the same when aligned for maximal correspondence. Similarly, two nucleotide sequences have "100% nucleotide sequence identity" if the nucleotide residues of the two nucleotide sequences are the same when aligned for maximal correspondence. Sequence comparisons can be performed using standard software programs such as those included in the LASERGENE bioinformatics computing suite, which is produced by DNASTAR (Madison, Wis.). Other methods for comparing two nucleotide or amino acid sequences by determining optimal alignment are well-known to those of skill in the art (see, for example, Peruski and Peruski, The Internet and the New Biology: Tools for Genomic and Molecular Research (ASM Press, Inc. 1997), Wu et al. (eds.), "Information Superhighway and Computer Databases of Nucleic Acids and Proteins," in Methods in Gene Biotechnology, pages 123 151 (CRC Press, Inc. 1997), and Bishop (ed.), Guide to Human Genome Computing, 2nd Edition (Academic Press, Inc. 1998)). Particular methods for determining sequence identity are described below.

Regardless of the particular method used to identify a variant gene, a variant gene encodes a polypeptide which can be characterized by its ability to bind specifically to an anti-(polypeptide according to the invention) antibody.

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

An "amino acid residue" can be a natural or non-natural amino acid residue linked peptide bonds or bonds different from peptide bonds. The amino acid residues can be in D-configuration or L-configuration. An amino acid residue comprises an amino terminal part (NH$_2$) and a carboxy terminal part (COOH) separated by a central part comprising a carbon atom, or a chain of carbon atoms, at least one of which comprises at least one side chain or functional group. NH$_2$ refers to the amino group present at the amino terminal end of an amino acid or peptide, and COOH refers to the carboxy group present at the carboxy terminal end of an amino acid or peptide. The generic term amino acid comprises both natural and non-natural amino acids. Natural amino acids of standard nomenclature as listed in J. Biol. Chem., 243:3552-59 (1969) and adopted in 37 C.F.R., section 1.822(b)(2) belong to the group of amino acids listed in Table 1 herein below. Non-natural amino acids are those not listed in Table 1. Examples of non-natural amino acids are those listed e.g. in 37 C.F.R. section 1.822(b)(4), all of which are incorporated herein by reference. Also, non-natural amino acid residues include, but are not limited to, modified amino acid residues, L-amino acid residues, and stereoisomers of D-amino acid residues.

TABLE 1

Natural amino acids and their respective codes.

| Symbols | | |
|---|---|---|
| 1-Letter | 3-Letter | Amino acid |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

An "equivalent amino acid residue" refers to an amino acid residue capable of replacing another amino acid residue in a polypeptide without substantially altering the structure and/or functionality of the polypeptide. Equivalent amino acids thus have similar properties such as bulkiness of the side-chain, side chain polarity (polar or non-polar), hydrophobicity (hydrophobic or hydrophilic), pH (acidic, neutral or basic) and side chain organization of carbon molecules (aromatic/aliphatic). As such, "equivalent amino acid residues" can be regarded as "conservative amino acid substitutions".

The classification of equivalent amino acids refers in one embodiment to the following classes: 1) HRK, 2) DENQ, 3) C, 4) STPAG, 5) MILV and 6) FYW Within the meaning of the term "equivalent amino acid substitution" as applied herein, one amino acid may be substituted for another, in one embodiment, within the groups of amino acids indicated herein below:
i) Amino acids having polar side chains (Asp, Glu, Lys, Arg, His, Asn, Gln, Ser, Thr, Tyr, and Cys,)
ii) Amino acids having non-polar side chains (Gly, Ala, Val, Leu, Ile, Phe, Trp, Pro, and Met)
iii) Amino acids having aliphatic side chains (Gly, Ala Val, Leu, Ile)
iv) Amino acids having cyclic side chains (Phe, Tyr, Trp, His, Pro)
v) Amino acids having aromatic side chains (Phe, Tyr, Trp)
vi) Amino acids having acidic side chains (Asp, Glu)
vii) Amino acids having basic side chains (Lys, Arg, His)
viii) Amino acids having amide side chains (Asn, Gln)
ix) Amino acids having hydroxy side chains (Ser, Thr)
x) Amino acids having sulphur-containing side chains (Cys, Met),
xi) Neutral, weakly hydrophobic amino acids (Pro, Ala, Gly, Ser, Thr)
xii) Hydrophilic, acidic amino acids (Gln, Asn, Glu, Asp), and
xiii) Hydrophobic amino acids (Leu, Ile, Val)

A Venn diagram is another method for grouping of amino acids according to their properties (Livingstone & Barton, CABIOS, 9, 745-756, 1993). In another preferred embodiment one or more amino acids may be substituted with another within the same Venn diagram group.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

A "fusion protein" is a hybrid protein expressed by a nucleic acid molecule comprising nucleotide sequences of at least two genes. For example, a fusion protein can comprise at least part of a polypeptide according to the present invention fused with a polypeptide that binds an affinity matrix. Such a fusion protein provides a means to isolate large quantities of a polypeptide according to the present invention using affinity chromatography.

The term "expression" refers to the biosynthesis of a gene product. For example, in the case of a structural gene, expression involves transcription of the structural gene into mRNA and the translation of mRNA into one or more polypeptides.

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., EMBO J. 4:1075 (1985); Nilsson et al., Methods Enzymol. 198:3 (1991)), glutathione S transferase (Smith and Johnson, Gene 67:31 (1988)), Glu-Glu affinity tag (Grussenmeyer et al., Proc. Natl. Acad. Sci. USA 82:7952 (1985)), substance P, FLAG peptide (Hopp et al., Biotechnology 6:1204 (1988)), streptavidin binding peptide, or other antigenic epitope or binding domain. See, in general, Ford et al., Protein Expression and Purification 2:95 (1991). DNAs encoding affinity tags are available from commercial suppliers (e.g., Pharmacia Biotech, Piscataway, N.J.).

The "insulin-like growth factors", or IGFs are polypeptides with high sequence similarity to insulin. IGFs are part of a complex system that cells use to communicate with their physiologic environment. This complex system (often referred to as the IGF "axis") consists of two cell-surface receptors (IGF1R and IGF2R), two ligands (IGF-1 and IGF-2), a family of six high-affinity IGF binding proteins (IGFBP 1-6), as well as associated IGFBP degrading enzymes, referred to collectively as proteases. Insulin-like growth factor 1 (IGF-1) is mainly secreted by the liver as a result of stimulation by growth hormone (GH). IGF-1 is important for both the regulation of normal physiology, as well as a number of pathological states, including cancer. The IGF axis has been shown to play roles in the promotion of cell proliferation and the inhibition of cell death (apoptosis). Insulin-like growth factor 2 (IGF-2) is thought to be a primary growth factor required for early development while IGF-1 expression is required for achieving maximal growth. While IGF-2 may be primarily fetal in action, it is also essential for development and function of organs such as the brain, liver and kidney.

The "IGF binding proteins", or IGFBP, help to modulate IGF action in complex ways. These involve both inhibiting IGF action by preventing binding to the IGF-1 receptor as well as promoting IGF action possibly through aiding in delivery to the receptor and increasing IGF half-life. Currently, there are 6 characterized IGF Binding Proteins (IGFBP1-6). There is currently significant data suggesting that IGFBPs have other functions in addition to their ability to regulate IGFs.

LNR: Lin12-Notch repeat. PAPP-A contains three LNR modules, which are unique to PAPP-A, its homologue PAPP-A2, and the family of Notch receptors. In PAPP-A and PAPP-A2, two LNR modules (LNR1 and 2) are inserted into the proteolytic domain, whereas the third (LNR3) is located C-terminal to the CCP modules. Within the PAPP-A dimer, the LNR modules probably form trimeric units composed of LNR1 and 2 from one subunit and LNR3 from the other subunit. Compromised LNR functionality renders PAPP-A unable to cleave IGFBP-4, while cleavage of IGFBP-5 is unaffected.

The "complement system" is a biochemical cascade which helps clear pathogens from an organism. It is part of the larger immune system that is not adaptable and does not change over the course of an individual's lifetime; as such it belongs to the innate immune system. However, it can be recruited and brought into action by the adaptive immune system. The complement system consists of a number of small proteins found in the blood, normally circulating as inactive zymogens. When stimulated by one of several triggers, proteases in the system cleave specific proteins to release cytokines and initiate an amplifying cascade of further cleavages. The end result of this activation cascade is massive amplification of the response and activation of the cell-killing membrane attack complex. Over 20 proteins and protein fragments make up the complement system, including serum proteins, serosal proteins, and cell membrane receptors.

"Complement control proteins", or CCP, are present on cell-surfaces and involved in regulation of the complement system. Such regulators act to disrupt the formation of convertases, which are bimolecular complexes formed early on in the activation cascade. Their presence on self-surfaces, and their absence from the surfaces of foreign particles, means that these regulators perform the important task of targeting complement to where it is needed (bacteria, virus, cell debris and antibody-antigen complexes) while preventing activation on host tissues. "Regulators of complement activation (RAC)" is a synonym for the term CCP.

"Enzyme-Linked Immuno Sorbent Assay", or ELISA, is a biochemical technique used mainly in immunology to detect the presence of an antibody or an antigen in a sample. Performing an ELISA involves at least one antibody with specificity for a particular antigen. The sample with an unknown amount of antigen is immobilized on a solid support (usually a polystyrene microtiter plate) either non-specifically (via adsorption to the surface) or specifically (via capture by another antibody specific to the same antigen, in a "sandwich" ELISA). After the antigen is immobilized, the detection antibody is added thus forming a complex with the antigen. The detection antibody can be covalently linked to an enzyme, or can itself be detected by a secondary antibody which is linked to an enzyme through bioconjugation. Between each step the plate is typically washed with a mild detergent solution to remove any proteins or antibodies that are not specifically bound. After the final wash step the plate is developed by adding an enzymatic substrate to produce a visible signal, which indicates the quantity of antigen in the sample. Older ELISAs utilize chromogenic substrates, though newer assays employ fluorogenic substrates with much higher sensitivity. "Enzyme ImmunoAssay", or EIA, is a synonym for the ELISA.

MMP=Matrix MetalloProteinases are zinc-dependent endopeptidases; other family members are adamalysins, serralysins, and astacins. The MMPs belong to a larger family of proteases known as the metzincin superfamily. Collectively they are capable of degrading all kinds of extracellular matrix proteins, but also can process a number of bioactive molecules. They are known to be involved in the cleavage of cell surface receptors, the release of apoptotic ligands (such as the FAS ligand), and chemokine in/activation. MMPs are also thought to play a major role on cell behaviors such as cell proliferation, migration (adhesion/dispersion), differentiation, angiogenesis, apoptosis and host defense.

An exosite is defined as 'an additional substrate-binding site on a protease distinct from the catalytic core'. A strategy to facilitate substrate binding and subsequent cleavage by MMPs is through specialized secondary substrate binding sites on discrete substrate binding domains, or smaller functional modules, located outside the active site. Adding protein-binding domains and modules increases the affinity of the proteinase for particular substrates and can modify the specificity of the main function of the MMP catalytic domain, which is to cleave scissile bonds. These secondary specificity sites are termed "ectodomains" or "exosites". One domain or module can display multiple binding sites for the same or different substrates. Substrate interactions with exosites can influence the behaviour of a proteinase in a number of ways. Exosites modulate and broaden the substrate specificity profile of MMPs by providing an additional contact area not influenced by the primary specificity subsites. Variation in the substrate binding properties of these modules or domains can alter the substrate preference of the MMP, and as part of the MMP degradative system, may add competitive advantage to the proteinase to degrade particular substrates. In this way, the function of the proteinase is refined and can be made, in general, more specific or efficient. Substrate binding is often the main function of specialized modules. Thus, simplicity through modular design is an attractive concept where the addition of modules and domains to the proteinase catalytic domain generates new diversity in substrate preference. In addition to tethering substrates to the enzyme to potentiate cleavage, exosites may be involved in essential "substrate preparation" prior to cleavage. For example, the localized "unwinding" of native collagen substrates by MMPs has been termed triple helicase activity. Exosites can also target the enzyme to substrate in tissues or to cell-associated substrates. Thus, the identification of substrate exosites and the development of specific drugs designed to bind and block these sites potentially offers new pathways to highly selective anti-MMP therapeutics that are selective for the degradation of specific substrates by that MMP. This promises a novel therapeutic approach with reduced side effects. Exosites can influence the behaviour of MMPs in a number of important ways. First, by increasing the affinity of MMPs for substrate, exosites are a highly efficient adaptation that enables protein-ase targeting to macromolecular assemblies of substrate such as fibers in the tissue or on cells. In addition to spatially targeting MMPs to substrate, exosite binding also impacts on the kinetic properties of the proteinase in other ways.

Due to the imprecision of standard analytical methods, molecular weights and lengths of polymers are understood to be approximate values. When such a value is expressed as "about" X or "approximately" X, the stated value of X will be understood to be accurate to +/−20%, such as +/−10%, for example +/−5%.

DETAILED DESCRIPTION OF THE DRAWINGS

Figure 1:
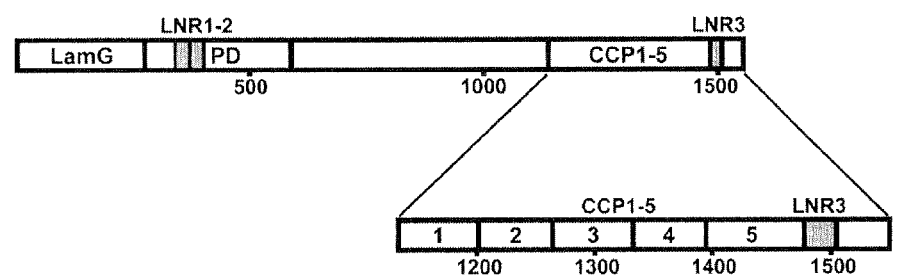
FIG. 1. Schematic representation of the PAPP-A subunit.

FIG. 1. Schematic Representation of the PAPP-A Subunit.

The identified protein modules of the 1547-residue PAPP-A subunit include an N-terminal laminin G-like module (LamG), a proteolytic domain (PD), three Lin12-Notch repeat modules (LNR1-3), and five complement control protein modules (CCP1-5). The position of the C-terminal recombinant fragment, used for immunization (residues 1129-1545 of murine PAPP-A) and for selection of phages (residues 1133-1547 of human PAPP-A), is emphasized.

Figure 2:
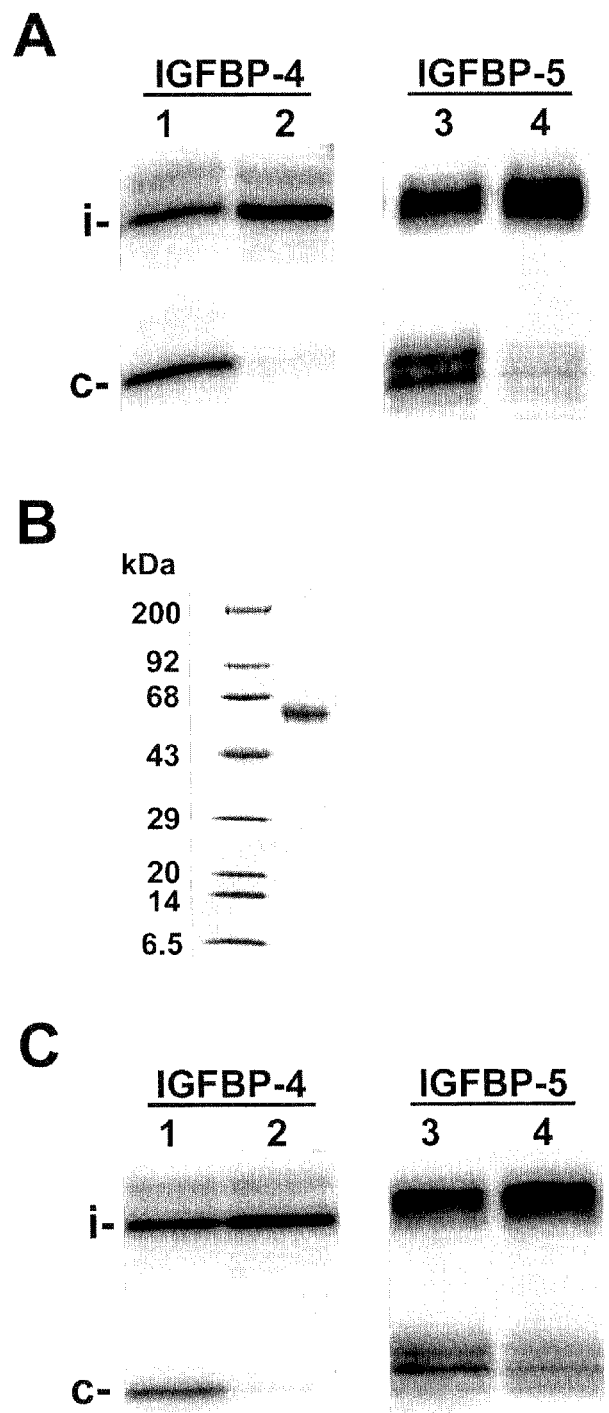
FIG. 2. Differential inhibition of PAPP-A proteolytic activity by polyclonal antibodies.

FIG. 2. Differential Inhibition of PAPP-A Proteolytic Activity by Polyclonal Antibodies.

A) Radiolabeled IGFBP-4 or -5 (10 nM) was incubated (1 h at 37° C.) with human PAPP-A (0.1 nM) in the absence (lane 1 and 3) or presence (lane 2 and 4) of polyclonal anti-PAPP-A (20 μg/mL). The proteolytic cleavage was visualized by SDS-PAGE followed by autoradiography using a phosphorimager. The positions of intact substrates (i) and co-migrating cleavage products (c) are indicated. B) Coomassie-stained SDS-PAGE of purified C-terminal fragment of murine PAPP-A, representing residues 1129-1545. The protein was expressed in 293T cells and purified by successive steps of nickel affinity chromatography and heparin affinity chromatography. C) Radiolabeled IGFBP-4 or -5 (10 nM) was digested (1 h at 37° C.) with murine PAPP-A (0.1 nM) in the absence (lane 1 and 3) or presence (lane 2 and 4) of polyclonal chicken antibodies (80 μg/mL IgY) raised against the C-terminal fragment of PAPP-A, shown in B.

Figure 3:
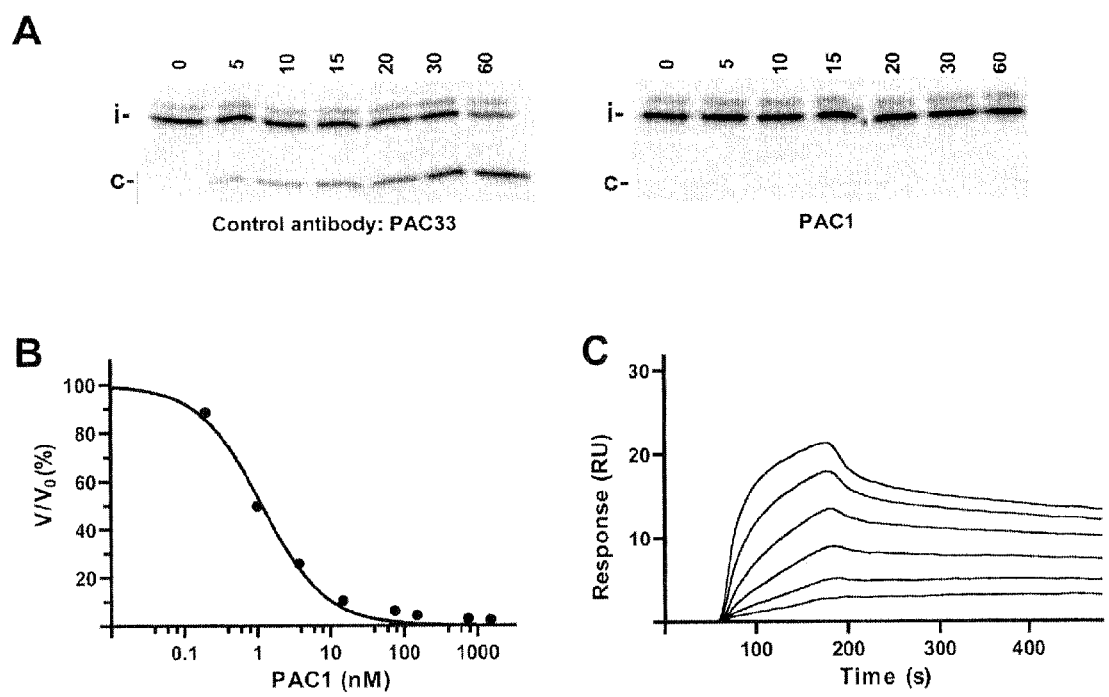
FIG. 3. Inhibition of IGFBP-4 cleavage by scFv antibodies specific for the C-terminus of PAPP-A.

FIG. 3. Inhibition of IGFBP-4 Cleavage by scFv Antibodies Specific for the C-Terminus of PAPP-A.

A) Cleavage of IGFBP-4 (10 nM) by human PAPP-A (0.1 nM) in the presence of PAC1 (1.5 μM). The cleavage reaction was incubated (37° C.), and samples were taken out at intervals from 0 to 60 min, as indicated above each lane. The cleavage was visualized by SDS-PAGE followed by autoradiography. At 60 min, a faint band is visible at the position of the cleavage products (c). B) Cleavage of IGFBP-4 (10 nM) by murine PAPP-A (0.1 nM) for 1 h at 37° C. in the presence of 0-750 nM PAC1, as indicated above each lane. C) Cleavage of IGFBP-4 (10 nM) by PAPP-A (0.1 nM) was analyzed at different concentrations of PAC1. Relative initial velocities, determined independently, are plotted as a function of PAC1 concentration. All concentrations were determined by amino acid analysis (IGFBP-4 and PAC1) or ELISA (PAPP-A). Assuming competitive inhibition, an inhibitory constant was calculated ($K_i$=1.2 nM±0.1). D) Sensorgrams showing binding of PAC1 to immobilized human PAPP-A. Purified PAC1 (0.35, 0.7, 1.4, 2.8, 5.5, and 11 nM) was injected onto the chip at 37° C. for 120 s followed by dissociation for 300 s. Using a 1:1 binding model, kinetic parameters were calculated based on global fitting: $k_a$=4.36×10$^6$ M$^{-1}$s$^{-1}$; $k_d$=1.09×10$^{-3}$ s$^{-1}$; $K_D$=0.25 nM ($\chi^2$=0.23).

Figure 4:
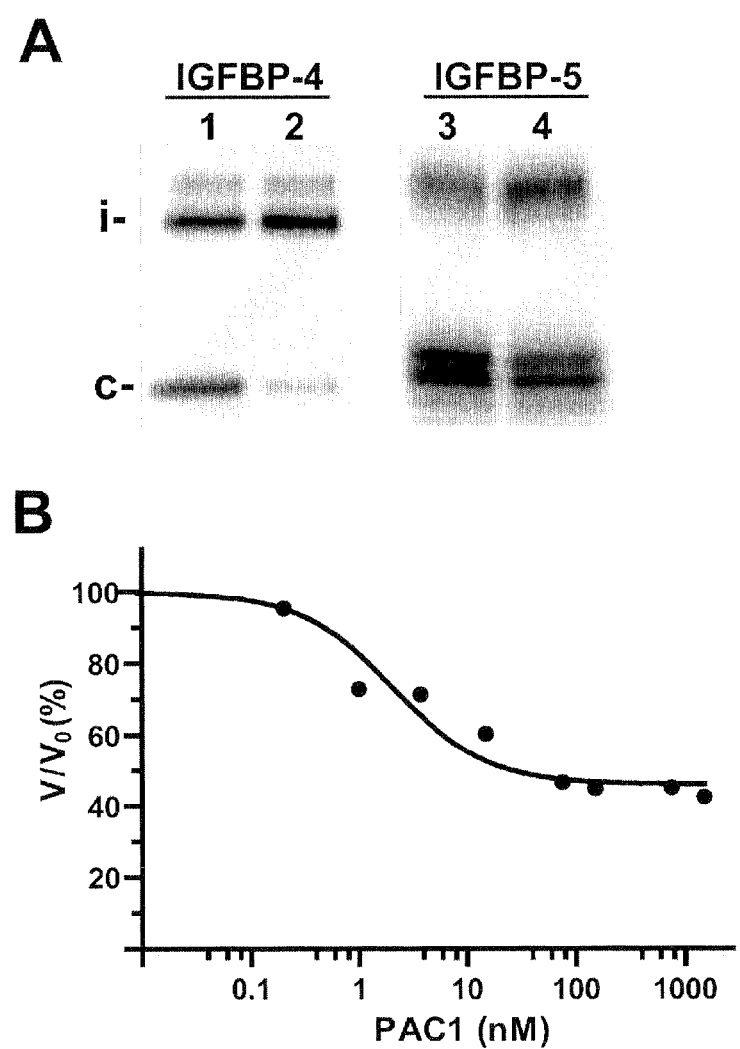
FIG. 4. Proteolysis of IGFBP-5 is partially inhibited by inhibitors of IGFBP-4 proteolysis.

FIG. 4. Proteolysis of IGFBP-5 is Partially Inhibited by Inhibitors of IGFBP-4 Proteolysis.

A) Comparison of the effect of PAC1 on PAPP-A cleavage of IGFBP-4 and -5. Radiolabeled IGFBP-4 or -5 (10 nM) was incubated (1 h at 37° C.) with human PAPP-A (0.1 nM) in the absence (lane 1 and 3) or presence (lane 2 and 4) of PAC1 20 nM. The proteolytic cleavage was visualized by SDS-PAGE followed by autoradiography. B) Cleavage of IGFBP-5 (10 nM) by PAPP-A (0.1 nM) was analyzed at different concentrations of PAC1. Relative initial velocities are plotted as a function of PAC1 concentration. The activity of PAPP-A against IGFBP-5 at saturating concentrations of PAC1 is approximately 45%. A sigmoidal dose-response curve was fitted to the data. All concentrations were determined by amino acid analysis (IGFBP-5 and PAC1) or ELISA (PAPP-A).

Figure 5:
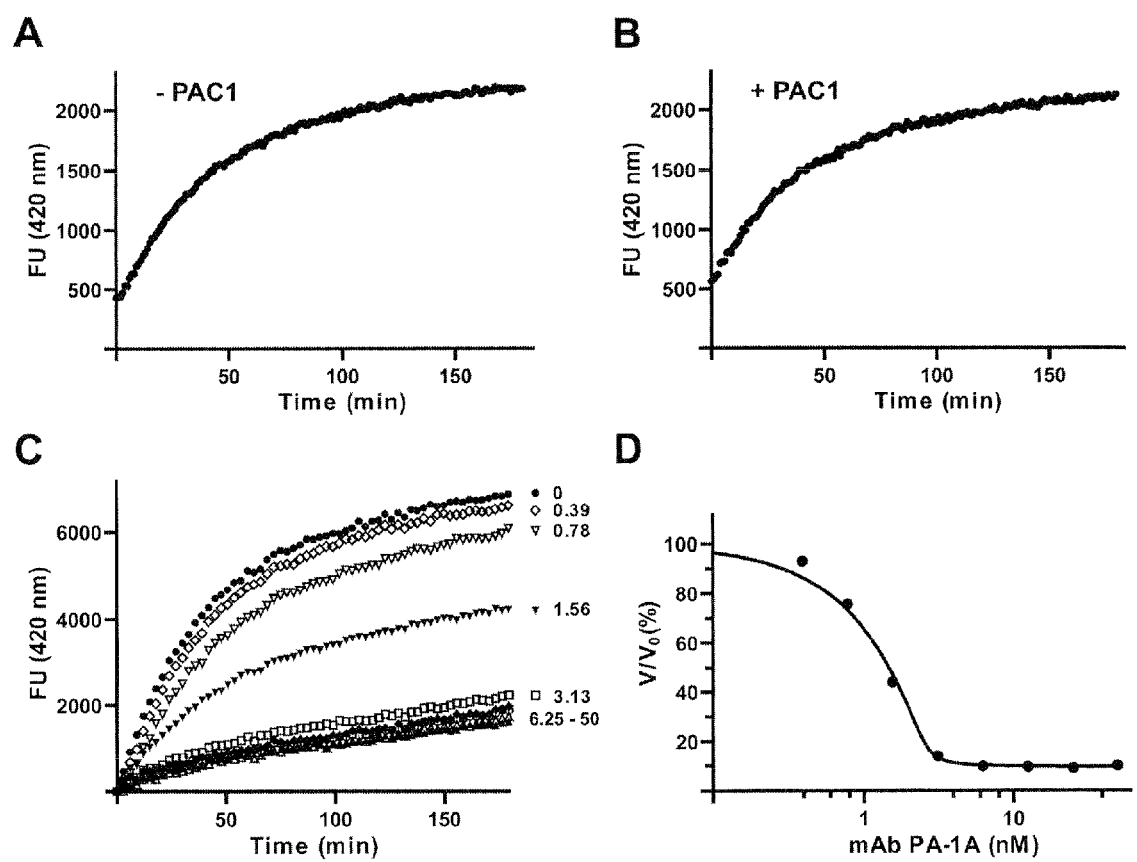
FIG. 5. PAC1 shows no inhibitory activity towards a synthetic peptide substrate.

FIG. 5. PAC1 Shows No Inhibitory Activity Towards a Synthetic Peptide Substrate.

A) Cleavage by human PAPP-A (5 nM) of a synthetic peptide (5 μM) derived from IGFBP-4. The peptide was derived with a fluorescent donor/quencher pair, which allows the detection of PAPP-A activity by the increase in emitted light at 420 nm, which follows proteolytic cleavage of the peptide. B) A similar experiment carried out in the presence of PAC1 (1 μM). C) Progress curves for the PAPP-A (5 nM) mediated cleavage of the peptide substrate (10 μM) in the presence of mAb PA-1A (0.39-50 nM), as indicated. D) Relative initial velocities (V/V$_0$%) determined from the progress curves are plotted as a function of mAb PA-1A concentration. The plot demonstrates effective inhibition of peptide cleavage by tight binding of mAb PA-1A to PAPP-A, but complete inhibition is not observed at saturating concentrations of mAb PA-1A.

Figure 6:
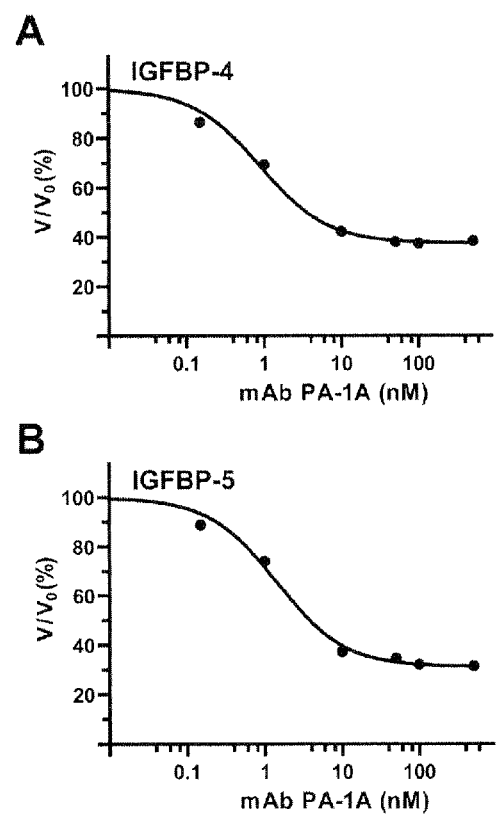
FIG. 6. Proteolysis of IGFBP-4 and -5 is incompletely inhibited by PA-1A.

FIG. 6. Proteolysis of IGFBP-4 and -5 is Incompletely Inhibited by PA-1A.

A) Cleavage of IGFBP-4 (10 nM) by human PAPP-A (0.1 nM) was analyzed at different concentrations of mAb PA-1A, and relative initial velocities are plotted as a function of PA-1A concentration. A sigmoidal dose-response curve was fitted to the data. B) similar analysis with IGFBP-5.

Figure 7:
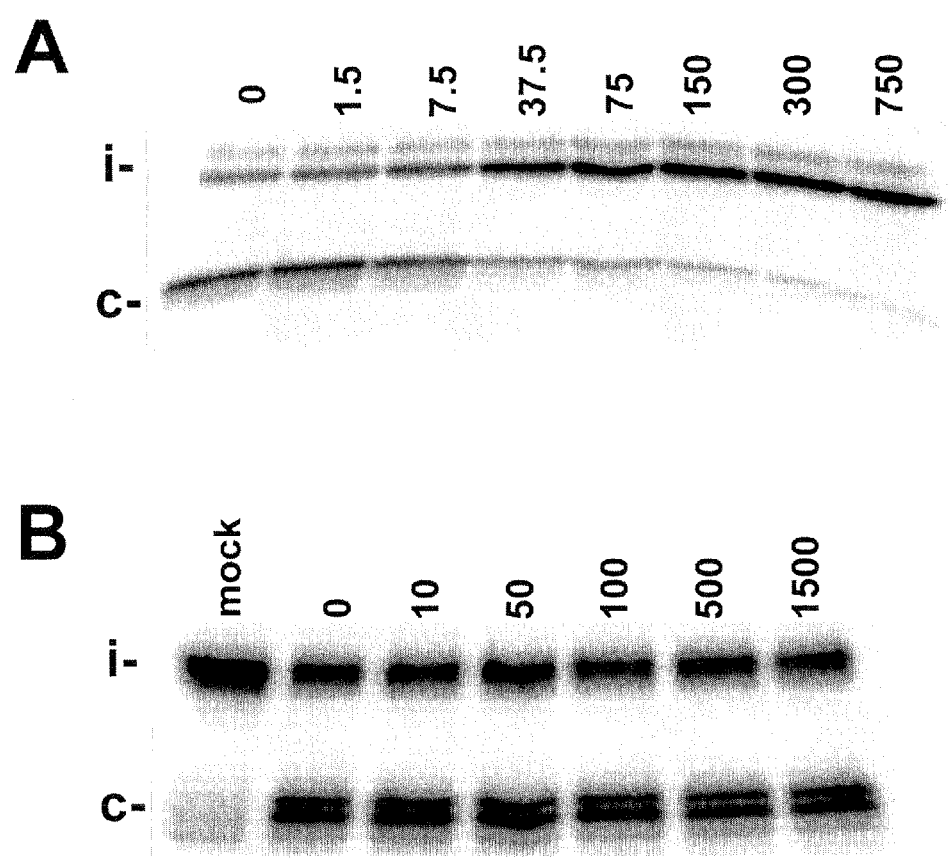
FIG. 7. PAC1 does not inhibit the proteolytic activity of PAPP-A2.

FIG. 7. PAC1 does not Inhibit the Proteolytic Activity of PAPP-A2.

A, cleavage of IGFBP-4 (10 nM) by murine PAPP-A (0.1 nM) for 1 h at 37° C. in the presence of 0-750 nM PAC1, as indicated above each lane. B, cleavage of IGFBP-5 (10 nM) by human PAPP-A2 (approximately 0.1 nM) for 1 h at 37° C. in the presence of 0-1500 nM PAC1, as indicated above each lane. The proteolytic cleavage was visualized by SDS-PAGE followed by autoradiography.

Figure 8:
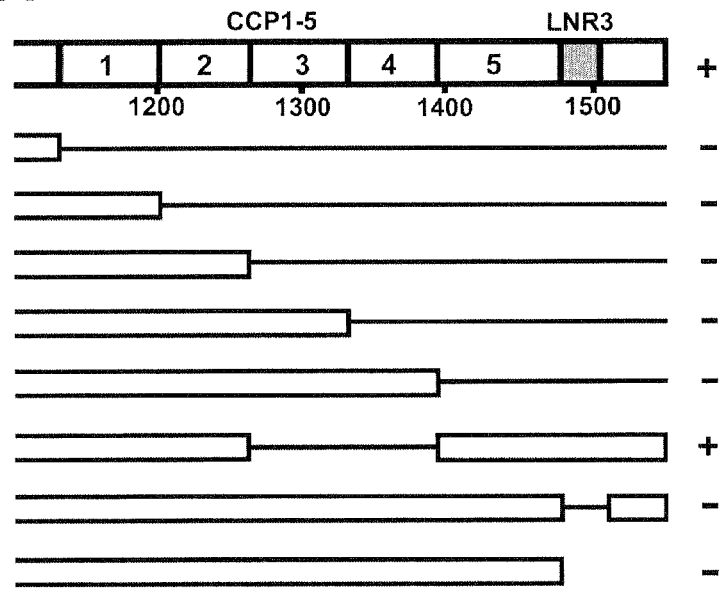
FIG. 8. Mapping of PAC1 and PAC2 to a calcium ion dependent epitope of PAPP-A.
Figure 8:
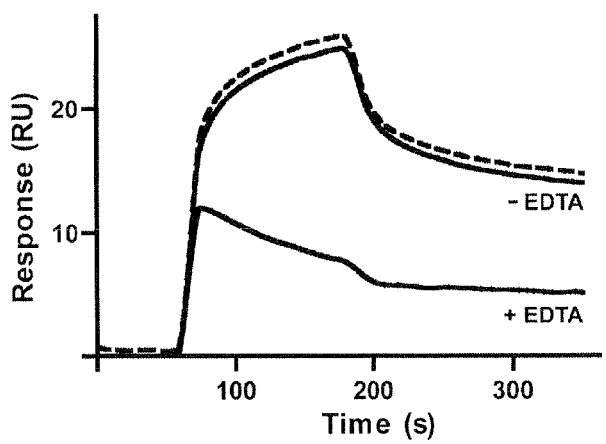

FIG. 8. Mapping of PAC1 and PAC2 to a Calcium Ion Dependent Epitope of PAPP-A.

A, PAC1 binding to human PAPP-A/PAPP-A2 chimeras or truncated human PAPP-A variants analyzed by ELISA. Sequence derived from PAPP-A is shown by open bars, and absence of binding (−) or binding (+) is indicated. B, calcium ion dependent binding of PAC1 (175 nM) to immobilized PAPP-A demonstrated by surface plasmon resonance. Samples with or without EDTA (10 mM) were injected (120 s) followed by dissociation (180 s) (solid lines). The dashed line shows binding of PAC1 after reequilibration of the flow cell with the calcium ion containing running buffer, demonstrating that PAPP-A LNR3 binds calcium reversibly. C, binding of PAC1, PAC2, and PAC5 to mutants of PAPP-A LNR3, in which residues Asp-1484, Asp-1499, and Asp-1502, predicted to coordinate a calcium ion are substituted individually with alanine, analyzed by ELISA. The absence of binding (−) or binding (+) is indicated. PAC5, which was used as a positive control, binds to an epitope of PAPP-A located N-terminal to CCP1.

DETAILED DESCRIPTION OF THE INVENTION

Exosite Interactors

In one embodiment the present invention relates to one or more exosite interactors. An exosite interaction can be any substance capable of interacting with an exosite in any protein. This interaction can be dependent on calcium ions. In one embodiment said protein is an enzyme.

The one or more exosite interactors can be one or more exosite antagonists and/or one or more exosite agonists. Accordingly, the one or more exosite interactors can be one or more exosite inhibitors and/or one or more exosite stimulators.

In one preferred embodiment the exosite inhibitor results in the general inhibition of substrate proteolysis of known or unknown substrates. In another preferred embodiment the exosite inhibitor results in inhibition of IGFBP-4 proteolysis. In yet another preferred embodiment the exosite inhibitor results in stimulation of IGF release.

The present invention relates to one or more protease inhibitor(s) that cause general inhibition of one or more physiological substrates of a protease by targeting a substrate binding exosite. The present invention also relates to one or more protease inhibitor(s) that cause differential inhibition of two or more physiological substrates of a protease by targeting a substrate binding exosite.

In one embodiment the one or more exosite interactors comprises one or more antibodies.

In one embodiment the one or more exosite interactors comprises one or more small molecule drug(s).

In yet another embodiment the exosite interactors comprises one or more protein(s). The one or more proteins can be either synthetic and/or natural protein(s). In another embodiment the exosite interactors comprises one or more polypeptide(s). The one or more peptides can be either synthetic and/or natural polypeptides.

The present invention further relates to the use of any of the exosite interactors described above for use as a medicament.

The present invention also relates to methods for generation of any of the exosite interactors described above. The method for generation of an exosite interactor can comprise one or more steps of: 1) PCR, 2) cloning, 3) generation of plasmid construct e.g. comprising a tag, 4) expression of protein in e.g. mammalian, bacterial or yeast cells, 5) expression and purification of protein.

The present invention also relates to methods for identification of an exosite and/or exosite interactor. The exosite interactor can be an exosite agonist or antagonist. In one embodiment the identification of exosite interactors comprises screening of semi-synthetic phage libraries. Selection libraries may be phage antibody/peptide libraries, as well as aptamer-based or libraries or libraries based on organochemical compounds.

The present invention also relates to modulation of IGF release (stimulation or inhibition) using one or more exosite interactors. In addition, the present invention relates to modulation of IGFBP-4 proteolysis (stimulation or inhibition) using one or more exosite interactors.

In a preferred embodiment, the exosite interactors according to the present invention has a molecular weight in the range from 100 Da to 1,000,000 Da, such as from 100 Da to 500 Da, for example 500 Da to 1,000 Da, such as from 1,000 Da to 1,500 Da, for example 1,500 Da to 2,000 Da, such as from 2,000 Da to 2,500 Da, for example 2,500 Da to 3,000 Da, such as from 3,000 Da to 3,500 Da, for example 3,500 Da to 4,000 Da, such as from 4,000 Da to 4,500 Da, for example 4,500 Da to 5,000 Da, such as from 5,000 Da to 5,500 Da, for example 5,500 Da to 6,000 Da, such as from 6,000 Da to 6,500 Da, for example 6,500 Da to 7,000 Da, such as from 7,000 Da to 7,500 Da, for example 7,500 Da to 8,000 Da, such as from 8,000 Da to 8,500 Da, for example 8,500 Da to 9,000 Da, such as from 9,000 Da to 9,500 Da, for example 9,500 Da to 10,000 Da, such as from 10,000 Da to 20,000 Da, for example 20,000 Da to 30,000 Da, such as from 30,000 Da to 40,000 Da, for example 40,000 Da to 50,000 Da, such as from 50,000 Da to 60,000 Da, for example 60,000 Da to 70,000 Da, such as from 70,000 Da to 80,000 Da, for example 80,000 Da to 90,000 Da, such as from 90,000 Da to 100,000 Da, for example 100,000 Da to 150,000 Da, such as from 150,000 Da to 200,000 Da, for example 200,000 Da to 250,000 Da, such as from 250,000 Da to 300,000 Da, for example 300,000 Da to 350,000 Da, such as from 350,000 Da to 400,000 Da, for example 400,000 Da to 450,000 Da, such as from 450,000 Da to 500,000 Da, for example 500,000 Da to 550,000 Da, such as from 550,000 Da to 600,000 Da, for example 600,000 Da to 650,000 Da, such as from 650,000 Da to 700,000 Da, for example 700,000 Da to 750,000 Da, such as from 750,000 Da to 800,000 Da, for example 800,000 Da to 850,000 Da, such as from 850,000 Da to 900,000 Da, for example 900,000 Da to 950,000 Da, such as from 950,000 Da to 1,000,000 Da.

PAPP-A

The present invention also relates to the PAPP-A protein or DNA sequence comprising the natural exosite(s) of PAPP-A or any variant of the PAPP-A exosite(s) described elsewhere in this document.

The human sequence of PAPP-A is termed SEQ ID NO:1.
The human sequence of PAPP-A (SEQ ID NO:1) is:

```
EARGATEEPS  PPSRALYFSG  RGEQLRVLRA  DLELPRDAFT

LQVWLRAEGG  QRSPAVITGL  YDKCSYISRD  RGWVVGIHTI

SDQDNKDPRY  FFSLKTDRAR  QVTTINAHRS  YLPGQWVYLA

ATYDGQFMKL  YVNGAQVATS  GEQVGGIFSP  LTQKCKVLML

GGSALNHNYR  GYIEHFSLWK  VARTQREILS  DMETHGAHTA

LPQLLLQENW  DNVKHAWSPM  KDGSSPKVEF  SNAHGFLLDT

SLEPPLCGQT  LCDNTEVIAS  YNQLSSFRQP  KVVRYRVVNL

YEDDHKNPTV  TREQVDFQHH  QLAEAFKQYN  ISWELDVLEV

SNSSLRRRLI  LANCDISKIG  DENCDPECNH  TLTGHDGGDC

RHLRHPAFVK  KQHNGVCDMD  CNYERFNFDG  GECCDPEITN

VTQTCFDPDS  PHRAYLDVNE  LKNILKLDGS  THLNIFFAKS

SEEELAGVAT  WPWDKEALMH  LGGIVLNPSF  YGMPGHTHTM

IHEIGHSLGL  YHVFRGISEI  QSCSDPCMET  EPSFETGDLC

NDTNPAPKHK  SCGDPGPGND  TCGFHSFFNT  PYNNFMSYAD

DDCTDSFTPN  QVARMHCYLD  LVYQGWQPSR  KPAPVALAPQ

VLGHTTDSVT  LEWFPPIDGH  FFERELGSAC  HLCLEGRILV

QYASNASSPM  PCSPSGHWSP  REAEGHPDVE  QPCKSSVRTW

SPNSAVNPHT  VPPACPEPQG  CYLELEFLYP  LVPESLTIWV

TFVSTDWDSS  GAVNDIKLLA  VSGKNISLGP  QNVFCDVPLT

IRLWDVGEEV  YGIQIYTLDE  HLEIDAAMLT  STADTPLCLQ

CKPLKYKVVR  DPPLQMDVAS  ILHLNRKFVD  MDLNLGSVYQ
```

-continued

```
YWVITISGTE ESEPSPAVTY IHGRGYCGDG IIQKDQGEQC

DDMNKINGDG CSLFCRQEVS FNCIDEPSRC YFHDGDGVCE

EFEQKTSIKD CGVYTPQGFL DQWASNASVS HQDQQCPGWV

IIGQPAASQV CRTKVIDLSE GISQHAWYPC TISYPYSQLA

QTTFWLRAYF SQPMVAAAVI VHLVTDGTYY GDQKQETISV

QLLDTKDQSH DLGLHVLSCR NNPLIIPVVH DLSQPFYHSQ

AVRVSFSSPL VAISGVALRS FDNFDPVTLS SCQRGETYSP

AEQSCVHFAC EKTDCPELAV ENASLNCSSS DRYHGAQCTV

SCRTGYVLQI RRDDELIKSQ TGPSVTVTCT EGKWNKQVAC

EPVDCSIPDH HQVYAASFSC PEGTTFGSQC SFQCRHPAQL

KGNNSLLTCM EDGLWSFPEA LCELMCLAPP PVPNADLQTA

RCRENKHKVG SFCKYKCKPG YHVPGSSRKS KKRAFKTQCT

QDGSWQEGAC VPVTCDPPPP KFHGLYQCTN GFQFNSECRI

KCEDSDASQG LGSNVIHCRK DGTWNGSFHV CQEMQGQCSV

PNELNSNLKL QCPDGYAIGS ECATSCLDHN SESIILPMNV

TVRDIPHWLN PTRVERVVCT AGLKWYPHPA LIHCVKGCEP

FMGDNYCDAI NNRAFCNYDG GDCCTSTVKT KKVTPFPMSC

DLQGDCACRD PQAQEHSRKD LRGYSHG
```

Variants of SEQ ID NO:1 are described elsewhere in this document.

In another embodiment the invention relates to PAPP-A with compromised LNR functionality. The compromised LNR functionality comprises compromised LNR3 functionality.

The present invention also relates to the use of the PAPP-A sequence with or without any of the above mentioned PAPP-A exosite(s) sequence variants for generation of one or more antibodies.

The present invention also relates to the use of the PAPP-A sequence with or without any of the above mentioned PAPP-A exosite(s) sequence variants for generation of one or more PAPP-A exosite(s) interaction molecules.

The present invention also relates to the use of the PAPP-A sequence and any of the above mentioned PAPP-A exosite(s) sequence variants for generation of one or more synthetic peptides capable of interacting with the PAPP-A exosite(s).

The Exosite(s) of PAPP-A

The present invention relates to the DNA sequence encoding the PAPP-A exosite(s).

The present invention also relates to the protein sequence of the PAPP-A exosite(s).

The human PAPP-A exosite(s) is termed SEQ ID NO:2. SEQ ID NO:2 is a part of SEQ ID NO:1. The human sequence of PAPP-A exosite(s) (SEQ ID NO:2) is:

```
1133       TDCPELAV ENASLNCSSS DRYHGAQCTV

SCRTGYVLQI RRDDELIKSQ TGPSVTVTCT EGKWNKQVAC

EPVDCSIPDH HQVYAASFSC PEGTTFGSQC SFQCRHPAQL

KGNNSLLTCM EDGLWSFPEA LCELMCLAPP PVPNADLQTA

RCRENKHKVG SFCKYKCKPG YHVPGSSRKS KKRAFKTQCT
```

-continued

```
QDGSWQEGAC VPVTCDPPPPK FHGLYQCTN GFQFNSECRI

KCEDSDASQG LGSNVIHCRK DGTWNGSFHV CQEMQGQCSV

PNELNSNLKL QCPDGYAIGS ECATSCLDHN SESIILPMNV

TVRDIPHWLN PTRVERVVCTA GLKWYPHPA LIHCVKGCEP

FMGDNYCDAI NNRAFCNYDG GDCCTSTVKT KKVTPFPMSC

DLQGDCACRD PQAQEHSRKD LRGYSHG    1547

Numbering is according to Kristensen et al.
(1994), Biochemistry 33: 1592-8.
(PMID: 7508748).
```

Variants of SEQ ID NO:2 are described elsewhere in this document.

The present invention also relates to the use of the PAPP-A exosite(s) sequence and any of the above mentioned PAPP-A exosite(s) sequence variants for generation of one or more antibodies.

The present invention also relates to the use of the PAPP-A exosite(s) sequence and any of the above mentioned PAPP-A exosite(s) sequence variants for generation of one or more PAPP-A exosite(s) interaction molecules.

The present invention also relates to the use of the PAPP-A exosite(s) sequence and any of the above mentioned PAPP-A exosite(s) sequence variants for generation of one or more synthetic peptides capable of interacting with the PAPP-A exosite(s).

The invention further relates to a fragment of SEQ ID NO:1 comprising SEQ ID NO:2. This fragment comprises from less than 1547 consecutive amino acid residues of SEQ ID NO:1, such as less than 1530 consecutive amino acid residues, e.g. less than 1510 consecutive amino acid residues, such as less than 1490 consecutive amino acid residues, e.g. less than 1470 consecutive amino acid residues, such as less than 1450 consecutive amino acid residues, e.g. less than 1430 consecutive amino acid residues, such as less than 1410 consecutive amino acid residues, e.g. less than 1390 consecutive amino acid residues, such as less than 1370 consecutive amino acid residues, e.g. less than 1350 consecutive amino acid residues, such as less than 1330 consecutive amino acid residues, e.g. less than 1310 consecutive amino acid residues, such as less than 1290 consecutive amino acid residues, e.g. less than 1270 consecutive amino acid residues, such as less than 1250 consecutive amino acid residues, e.g. less than 1230 consecutive amino acid residues, such as less than 1210 consecutive amino acid residues, e.g. less than 1190 consecutive amino acid residues, such as less than 1170 consecutive amino acid residues, e.g. less than 1150 consecutive amino acid residues, such as less than 1130 consecutive amino acid residues, e.g. less than 1110 consecutive amino acid residues, such as less than 1090 consecutive amino acid residues, e.g. less than 1070 consecutive amino acid residues, such as less than 1050 consecutive amino acid residues, e.g. less than 1030 consecutive amino acid residues, such as less than 1010 consecutive amino acid residues, e.g. less than 990 consecutive amino acid residues, such as less than 970, e.g. less than 950 consecutive amino acid residues, such as less than 930 consecutive amino acid residues e.g. less than 910 consecutive amino acid residues, such as less than 890 consecutive amino acid residues, e.g. less than 870 consecutive amino acid residues, such as less than 850 consecutive amino acid residues, e.g. less than 830 consecutive amino acid residues, such as less than 810 consecutive amino acid residues, e.g. less than 790 consecutive amino acid residues, such as less than 770 consecutive amino acid residues, e.g. less than 750 consecutive amino acid residues, such as less than 730 consecutive amino acid residues, e.g. less than 710 consecutive amino acid residues, such as less than 690 consecutive amino acid residues, e.g. less than 670 consecutive amino acid residues, such as less than 650 consecutive amino acid residues, e.g. less than 630 consecutive amino acid residues, such as less than 610 consecutive amino acid residues, e.g. less than 590 consecutive amino acid residues, such as less than 570 consecutive amino acid residues, e.g. less than 550 consecutive amino acid residues, such as less than 530 consecutive amino acid residues, e.g. less than 510 consecutive amino acid residues, such as less than 490 consecutive amino acid residues, e.g. less than 470 consecutive amino acid residues, such as less than 450 consecutive amino acid residues, e.g. less than 430 consecutive amino acid residues, such as less than 410 consecutive amino acid residues, e.g. less than 390 consecutive amino acid residues, such as less than 370 consecutive amino acid residues, e.g. less than 350 consecutive amino acid residues, such as less than 330, e.g. less than 310 consecutive amino acid residues, such as less than 290 consecutive amino acid residues e.g. less than 270 consecutive amino acid residues, such as less than 250 consecutive amino acid residues, e.g. less than 230 consecutive amino acid residues, such as less than 210 consecutive amino acid residues, e.g. less than 190 consecutive amino acid residues, such as less than 170 consecutive amino acid residues, e.g. less than 150 consecutive amino acid residues, such as less than 130 consecutive amino acid residues, e.g. less than 110 consecutive amino acid residues, such as less than 90 consecutive amino acid residues, e.g. less than 70 consecutive amino acid residues, such as less than 50 consecutive amino acid residues, e.g. less than 30 consecutive amino acid residues of SEQ ID NO:1.

PAPP-A Exosite(s) Interactors

In one embodiment the present invention relates to one or more PAPP-A exosite(s) interactors. A PAPP-A exosite(s) interactor can be any substance capable of interacting with a PAPP-A exosite(s). This interaction can be dependent on calcium ions.

The one or more PAPP-A exosite(s) interactors can be one or more PAPP-A exosite(s) antagonists and/or one or more PAPP-A exosite(s) agonists. Accordingly, the one or more PAPP-A exosite(s) interactors can be one or more PAPP-A exosite(s) inhibitors and/or one or more PAPP-A exosite(s) stimulators.

In one preferred embodiment the PAPP-A exosite(s) inhibitor results in general inhibition of substrate proteolysis of known or unknown substrates. In another preferred embodiment the PAPP-A exosite(s) inhibitor results in inhibition of IGFBP-4 proteolysis. In yet another preferred embodiment the exosite inhibitor results in stimulation of IGF release.

The present invention also relates to one or more PAPP-A exosite(s) inhibitor(s) that cause general inhibition of one or more physiological substrate(s) of PAPP-A by targeting a substrate binding PAPP-A exosite(s). The present invention also relates to one or more PAPP-A exosite(s) inhibitor(s) that cause differential inhibition of two or more physiological substrates of PAPP-A by targeting a substrate binding PAPP-A exosite(s).

In one embodiment the one or more PAPP-A exosite(s) interactors comprises one or more antibodies. The one or more antibodies can have an inhibitory or stimulatory effect on PAPP-A.

In one embodiment the one or more PAPP-A exosite(s) interactors comprises one or more small molecule drug(s).

In one embodiment the one or more PAPP-A exosite(s) interactors comprises one or more antibodies or fragments thereof.

In yet another embodiment the PAPP-A exosite(s) interactors comprises one or more protein(s). The one or more proteins can be either synthetic and/or natural protein(s). In another embodiment the PAPP-A exosite(s) interactors comprises one or more peptide(s). The one or more peptides can be either synthetic and/or natural peptides.

In one preferred embodiment the PAPP-A exosite(s) interactors results in partial or full inhibition of the activity of PAPP-A towards known or unknown substrates. In another preferred embodiment the PAPP-A exosite(s) interactors results in inhibition of the activity of PAPP-A towards its substrate IGFBP-4. In yet another preferred embodiment the PAPP-A exosite(s) interactors results in inhibition the activity of PAPP-A towards IGFBP-4 (full inhibition), and to a lesser extent towards IGFBP-5 (partial inhibition).

The present invention further relates to the use of any of the PAPP-A exosite(s) interactors described above for use as a medicament.

The present invention also relates to methods for generation of a PAPP-A exosite(s) interactor described above. The method for generation of a PAPP-A exosite(s) interactor can comprise one or more steps of: 1) PCR, 2) cloning, 3) generation of plasmid construct e.g. comprising a tag, 4) expression of protein in e.g. mammalian, bacterial or yeast cells, 5) expression and purification of protein.

The present invention also relates to methods for identification of a PAPP-A exosite(s) and/or PAPP-A exosite(s) interactor. The PAPP-A exosite(s) interactor can be an exosite(s) agonist or antagonist. In one embodiment the identification of exosite interactors comprises screening of semi-synthetic phage libraries.

In another embodiment the invention relates to a method for modulating the PAPP-A activity such as inhibition or stimulation of PAPP-A. The present invention also relates to modulation of the PAPP-A production e.g. by use of miRNA (microRNA) or siRNA (small interfering RNA).

In a preferred embodiment, the PAPP-A exosite(s) interactors according to the present invention has a molecular weight in the range from 100 Da to 1,000,000 Da, such as from 100 Da to 500 Da, for example 500 Da to 1,000 Da, such as from 1,000 Da to 1,500 Da, for example 1,500 Da to 2,000 Da, such as from 2,000 Da to 2,500 Da, for example 2,500 Da to 3,000 Da, such as from 3,000 Da to 3,500 Da, for example 3,500 Da to 4,000 Da, such as from 4,000 Da to 4,500 Da, for example 4,500 Da to 5,000 Da, such as from 5,000 Da to 5,500 Da, for example 5,500 Da to 6,000 Da, such as from 6,000 Da to 6,500 Da, for example 6,500 Da to 7,000 Da, such as from 7,000 Da to 7,500 Da, for example 7,500 Da to 8,000 Da, such as from 8,000 Da to 8,500 Da, for example 8,500 Da to 9,000 Da, such as from 9,000 Da to 9,500 Da, for example 9,500 Da to 10,000 Da, such as from 10,000 Da to 20,000 Da, for example 20,000 Da to 30,000 Da, such as from 30,000 Da to 40,000 Da, for example 40,000 Da to 50,000 Da, such as from 50,000 Da to 60,000 Da, for example 60,000 Da to 70,000 Da, such as from 70,000 Da to 80,000 Da, for example 80,000 Da to 90,000 Da, such as from 90,000 Da to 100,000 Da, for example 100,000 Da to 150,000 Da, such as from 150,000 Da to 200,000 Da, for example 200,000 Da to 250,000 Da, such as from 250,000 Da to 300,000 Da, for example 300,000 Da to 350,000 Da, such as from 350,000 Da to 400,000 Da, for example 400,000 Da to 450,000 Da, such as from 450,000 Da to 500,000 Da, for example 500,000 Da to 550,000 Da, such as from 550,000 Da to 600,000 Da, for example 600,000 Da to 650,000 Da, such as from 650,000 Da to 700,000 Da, for example 700,000 Da to 750,000 Da, such as from 750,000 Da to 800,000 Da, for example 800,000 Da to 850,000 Da, such as from 850,000 Da to 900,000 Da, for example 900,000 Da to 950,000 Da, such as from 950,000 Da to 1,000,000 Da.

In a further embodiment the present invention relates to a complex comprising a polypeptide sequence comprising a PAPP-A exosite(s) such as SEQ ID NO:1, SEQ ID NO:2 and/or SEQ ID NO:3 and a binding partner having an affinity for said exosite(s), wherein the binding of the binding partner to the exosite(s) alters the activity of PAPP-A. This binding partner has in one preferred embodiment a molecular weight in the range from 100 Da to 1,000,000 Da, such as from 100 Da to 500 Da, for example 500 Da to 1,000 Da, such as from 1,000 Da to 1,500 Da, for example 1,500 Da to 2,000 Da, such as from 2,000 Da to 2,500 Da, for example 2,500 Da to 3,000 Da, such as from 3,000 Da to 3,500 Da, for example 3,500 Da to 4,000 Da, such as from 4,000 Da to 4,500 Da, for example 4,500 Da to 5,000 Da, such as from 5,000 Da to 5,500 Da, for example 5,500 Da to 6,000 Da, such as from 6,000 Da to 6,500 Da, for example 6,500 Da to 7,000 Da, such as from 7,000 Da to 7,500 Da, for example 7,500 Da to 8,000 Da, such as from 8,000 Da to 8,500 Da, for example 8,500 Da to 9,000 Da, such as from 9,000 Da to 9,500 Da, for example 9,500 Da to 10,000 Da, such as from 10,000 Da to 20,000 Da, for example 20,000 Da to 30,000 Da, such as from 30,000 Da to 40,000 Da, for example 40,000 Da to 50,000 Da, such as from 50,000 Da to 60,000 Da, for example 60,000 Da to 70,000 Da, such as from 70,000 Da to 80,000 Da, for example 80,000 Da to 90,000 Da, such as from 90,000 Da to 100,000 Da, for example 100,000 Da to 150,000 Da, such as from 150,000 Da to 200,000 Da, for example 200,000 Da to 250,000 Da, such as from 250,000 Da to 300,000 Da, for example 300,000 Da to 350,000 Da, such as from 350,000 Da to 400,000 Da, for example 400,000 Da to 450,000 Da, such as from 450,000 Da to 500,000 Da, for example 500,000 Da to 550,000 Da, such as from 550,000 Da to 600,000 Da, for example 600,000 Da to 650,000 Da, such as from 650,000 Da to 700,000 Da, for example 700,000 Da to 750,000 Da, such as from 750,000 Da to 800,000 Da, for example 800,000 Da to 850,000 Da, such as from 850,000 Da to 900,000 Da, for example 900,000 Da to 950,000 Da, such as from 950,000 Da to 1,000,000 Da.

Small Molecule Drugs Interaction with the PAPP-A Exosite(s)

The present invention relates to one or more small molecule drug(s) capable of interacting with the PAPP-A exosite(s). In one embodiment the small molecule drug is directed to the C-terminal part of PAPP-A comprising LNR3. The C-terminal part is shown in FIG. 1 and comprises CCP1-5 and LNR3. These are included in SEQ ID NO:2.

In one embodiment the small molecule drug is directed to LNR3 of PAPP-A. In another embodiment the small molecule drug is interacting with the exosite(s) of PAPP-A (SEQ ID NO:2) or any variant thereof described any where in this document. These interactions can be dependent on calcium ions.

The present invention further relates to a method for development of one or more small molecule drug(s) that interact with the exosite(s) of PAPP-A (SEQ ID NO:2) or any variant thereof described any where in this document or with LNR3 of PAPP-A or with another fragment of PAPP-A. This method can comprise a selection of interaction partners which require the presence of calcium ions.

The present invention also relates to use of one or more small molecule drug(s) that interact with the exosite(s) of PAPP-A (SEQ ID NO:2) or any variant thereof described any where in this document or with LNR3 of PAPP-A or with another fragment of PAPP-A as a medicament.

The present invention further relates to selection of binders to PAPP-A, the PAPP-A exosite(s) and/or the PAC1 and PAC2 epitope in PAPP-A. The selection strategies for obtaining a PAPP-A interactors such as an inhibitor are in one embodiment based on specific elution by disruption of calcium binding. The C-terminal fragment of PAPP-A will in one preferred embodiment be immobilized either directly, or by means of PAPP-A specific antibodies. A combinatorial library of compounds will then be passed over the immobilized PAPP-A and subsequently thoroughly washed. Binding compounds will be eluted by addition of EDTA or other calcium binding compounds to disrupt the structure e.g. of the LNR3 module or to disrupt calcium ion binding of this module. Specific elution will allow selection of binders to a specific region of PAPP-A. Selection libraries may be phage antibody/peptide libraries, as well as aptamer-based or libraries or libraries based on organochemical compounds. This selection strategy may be used for identification of small molecule drugs or any other PAPP-A exosite(s) interactor.

"Small molecule": As used herein, the term "small molecule" refers to molecules, whether naturally-occurring or artificially created (e.g., via chemical synthesis), that have a relatively low molecular weight. Typically, small molecules are monomeric and they preferably have a molecular weight of less than about 1500 g/mol. Preferred small molecules are biologically active in that they produce a local or systemic effect in animals, preferably mammals, more preferably humans. In certain preferred embodiments, the small molecule is a drug. Preferably, though not necessarily, the drug is one that has already been deemed safe and effective for use by the appropriate governmental agency or body. For example, drugs for human use listed by the FDA under 21 C.F.R. sections 330.5, 331 through 361, and 440 through 460; drugs for veterinary use listed by the FDA under 21 C.F.R. sections 500 through 589, incorporated herein by reference, are all considered acceptable for use in accordance with the present invention.

In a preferred embodiment, the small molecule drug(s) that interact with the exosite(s) of PAPP-A (SEQ ID NO:2) or any variant thereof described any where in this document or with LNR3 of PAPP-A or with another fragment of PAPP-A according to the present invention has a molecular weight in the range from 10 Da to 10,000 Da, such as from 10 Da to 50 Da, for example 50 Da to 100 Da, such as from 100 Da to 150 Da, for example 150 Da to 200 Da, such as from 200 Da to 250 Da, for example 2500 Da to 300 Da, such as from 300 Da to 350 Da, for example 350 Da to 400 Da, such as from 400 Da to 450 Da, for example 450 Da to 500 Da, such as from 500 Da to 550 Da, for example 550 Da to 600 Da, such as from 600 Da to 650 Da, for example 650 Da to 700 Da, such as from 700 Da to 750 Da, for example 750 Da to 800 Da, such as from 800 Da to 850 Da, for example 850 Da to 900 Da, such as from 900 Da to 950 Da, for example 950 Da to 1,000 Da, such as from 1,000 Da to 2,000 Da, for example 2,000 Da to 3,000 Da, such as from 3,000 Da to 4,000 Da, for example 4,000 Da to 5,000 Da, such as from 5,000 Da to 6,000 Da, for example 6,000 Da to 7,000 Da, such as from 7,000 Da to 8,000 Da, for example 8,000 Da to 9,000 Da, such as from 9,000 Da to 10,000 Da.

Specific PAPP-A Exosite(s) Antibodies

In one embodiment the one or more PAPP-A exosite(s) inhibitor(s) comprises PAPP-A specific antibodies. Preferably, these antibodies do not bind and inhibit the related proteinase PAPP-A2.

In preferred embodiment the PAPP-A specific antibody is PAC1. In another preferred embodiment the PAPP-A specific antibody is PAC2. These interactions can be dependent on calcium ions.

The epitope recognized by PAC1 and PAC2 in human PAPP-A is termed SEQ ID NO:3.

The sequence of SEQ ID NO:3 is:

1478 CEPFMGDNYC DAINNRAFCN YDGGDCCTST VKTKKVTPFP

MSCDLQGDCA CRDPQAQEHS RKDLRGYSHG 1547

The epitope recognized by PAC1 and PAC2 in mouse PAPP-A is termed SEQ ID NO:4.

The sequence of SEQ ID NO:4 is:

1476

CEPFMGDNYCDAINNRAFCNYDGGDCCTSTVKTKKVTPFPMSCDLQNDCA

CRDPEAQEHNRKDLRGYSHG 1545

Variants of SEQ ID NO:3 and SEQ ID NO:4 are described elsewhere in this document.

PAC1 and PAC2 are termed SEQ ID NO:5 and SEQ ID NO:6, respectively. Amino acid sequences of inhibitors PAC1 and PAC2 are given below. Sequences are full-length sequences of scFv PAC1 and PAC2 and are derived from cDNA. The sequences include His- and c-myc tags (both underlined). This His- and/or c-myc tag can be substituted with any other tag suitable for purification. Alternatively, His- and/or c-myc tag can be omitted from the sequence. The sequences further include the CDR (complementarity determining region) (marked in bold).

PAC1 Sequence (SEQ ID NO:5):

EVQLLESGGGLVQPGGSLRLSCAASGFTFSSYAMSWVRQAPGKGLEWVSV

ITDMGRTTRYADSVKGRFTISRDNSKNTLYLQMNSLRAEDTAVYYCAKGL

RQFDYWGQGTLVTVSSGGGGSGGGGSGGGGSTDIQMTQSPSSLSASVGDR

VTITCRASQSISSYLNWYQQKPGKAPKLLIYHASQLQSGVPSRFSGSGSG

TDFTLTISSLOPEDFATYYCQQYGGNPTTFGQGTKVEIKRAAAHHHHHHG

AAEQKLISEEDLNGAA

PAC2 Sequence (SEQ ID NO:6):

EVQLLESGGGLVQPGGSLRLSCAASGFTFSSYAMSWVRQAPGKGLEWVSS

IQADGTRTGYADSVKGRFTISRDNSKNTLYLQMNSLRAEDTAVYYCAKQR

GIFDYWGQGTLVTVSSGGGGSGGGGSGGGGSTDIQMTQSPSSLSASVGDR

VTITCRASQSISSYLNWYQQKPGKAPKLLIYRASGLQSGVPSRFSGSGSG

TDFTLTISSLQPEDFATYYCQQSHHYPSTFGQGTKVEIKRAAAHHHHHHG

AAEQKLISEEDLNGAA

Variants of SEQ ID NO:5 and SEQ ID NO:6 are described elsewhere in this document.

The CDR regions of antibodies are highly variable. In the present invention, diversified residues of the CDR regions are shown in bold. A total of 18 residues are diversified: H50, H52, H52a, H53, H55, H56, H58, H95, H96, H97, H98, L50, L53, L91, L92, L93, L94 and L96 (H=heavy chain, L=light chain). Numbers indicate amino acid positions according to the manufacturer of the Tomlinson I and J libraries, from which the PAC antibodies have been selected.

In one embodiment, the CDR regions of antibodies such as PAC1, PAC2 and PAC5 (as described later) or any other PAPP-A antibody or any other exosite antibody are conserved in at least the 18 amino acid residues of the CDR, or at least 17 amino acid residues, e.g. at least 16 amino acid residues, or at least 15 amino acid residues, e.g. at least 14 amino acid residues, or at least 13 amino acid residues, e.g. at least 12 amino acid residues, or at least 11 amino acid residues, e.g. at least 10 amino acid residues of the hypervariable CDR region of said antibody.

In one embodiment, when the at least 18 amino acid residues of the CDR region are conserved, then the remaining amino acid sequence of antibodies such as PAC1, PAC2 and PAC5 (as described later) or any other PAPP-A antibody or any other exosite antibody may have at least 99.9% amino acid sequence identity to said antibody, or at least 99%, for example at least 98%, or at least 97%, for example at least 96%, or at least 95%, for example at least 94%, or at least 93%, for example at least 92%, or at least 91%, for example at least 90%, or at least 89%, for example at least 88%, or at least 87%, for example at least 86%, or at least 85%, for example at least 84%, or at least 83%, for example at least 82%, or at least 81%, for example at least 80%, or at least 79%, for example at least 78%, or at least 77%, for example at least 76%, or at least 75%, for example at least 74%, or at least 73%, for example at least 72%, or at least 71%, for example at least 70%, or at least 69%, for example at least 68%, or at least 67%, for example at least 66%, or at least 65%, for example at least 64%, or at least 63%, for example at least 62%, or at least 61%, for example at least 60%, or at least 58%, for example at least 56%, or at least 54%, for example at least 52%, or at least 50%, for example at least 48%, or at least 46%, for example at least 44%, or at least 42%, for example at least 40%, or at least 38%, for example at least 36%, or at least 34%, for example at least 32%, or at least 30%, for example at least 28%, or at least 26%, for example at least 24%, or at least 22%, for example at least 20%, or at least 18%, for example at least 16%, or at least 14%, for example at least 12%, or at least 10%, for example at least 8%, or at least 6%, for example at least 4%, or at least 2%, or at least 0.5% sequence identity to said antibody or an ortholog thereof.

In one aspect the present invention provides isolated polypeptides that have a substantially similar sequence identity to the antibodies according to the present invention, such as PAC1 or PAC2, or an ortholog thereof.

The term "substantially similar sequence identity" is used herein to denote polypeptides having at least 70%, such as at least 72%, for example at least 74%, such as at least 76%, for example at least 78%, such as at least 80%, for example at least 82%, such as at least 84%, for example at least 86%, such as at least 88%, for example at least 90%, such as at least 91%, for example at least 92%, such as at least 93%, for example at least 94%, such as at least 95%, for example at least 96%, such as at least 97%, for example at least 98%, such as at least 99%, or greater than 99% sequence identity to SEQ ID NO:5OR SEQ ID NO:6 or an ortholog thereof.

The present invention further relates to the use of PAPP-A specific antibodies for use as a medicament.

The present invention also relates to the use of PAC1 for use as a medicament. The present invention further relates to the use of PAC2 for use as a medicament. The present invention also relates to methods for generation of PAC1 and/or PAC2. The method for generation of PAC1 and/or PAC2 can comprise one or more steps of: 1) PCR, 2) cloning, 3) generation of plasmid construct e.g. comprising a tag, 4) expression of protein in e.g. mammalian, bacterial or yeast cells, 5) expression and purification of protein.

In yet another preferred embodiment, PAC1 and PAC2 binding to PAPP-A is absolutely dependent on the C-terminal PAPP-A exosite sequence LNR3, or the C-terminal side of the LNR3 module, and the presence of calcium ions. Thus, the epitopes recognized by PAC1 and PAC2 are comprised of amino acids within the 26-residue LNR3 module, at least in part.

The present invention also relates to PAC1 and PAC2 binding to PAPP-A exosite(s) that results in general inhibition of substrate proteolysis of known or unknown substrates. In one preferred embodiment, said inhibition is full or partial.

In another preferred embodiment PAC1 or PAC2 results in inhibition of IGFBP-4 proteolysis. In yet another preferred embodiment the exosite inhibitor results in stimulation of IGF release.

In another preferred embodiment the present invention also relates to PAC1 or PAC2 binding to PAPP-A exosite(s) that cause the general inhibition of one or more physiological substrate(s) of PAPP-A by targeting a substrate binding PAPP-A exosite(s).

The present invention also relates to PAC1 and PAC2 binding to PAPP-A exosite(s) that cause differential inhibition of two or more physiological substrates of PAPP-A by targeting a substrate binding PAPP-A exosite(s).

In yet another preferred embodiment, PAC1 and PAC2 binding to PAPP-A cause the full inhibition of PAPP-A-mediated cleavage of IGFBP-4 and the partial inhibition of IGFBP-5, thus causing partial differential inhibitory effects on PAPP-A substrates. In one embodiment, the PAC1 and PAC2 antibodies will not cause inhibition of other as yet known unknown PAPP-A substrates, whose cleavage may not be dependent on binding to the same exosite(s).

Specific PAPP-A Non-Exosite(s) Antibodies

In one embodiment the one or more PAPP-A non-exosite(s) inhibitor(s) comprises PAPP-A specific antibodies. Preferably, these antibodies do not bind and inhibit the related proteinase PAPP-A2.

In a preferred embodiment the PAPP-A specific antibody is PAC5.

Mapping of the epitope recognized by PAC5 in human PAPP-A show, that the binding site of PAC5 is localized in the stretch of PAPP-A comprising residues 600-937. The boundaries cannot be given exactly, but the binding site is 1) not within proteolytic domain, and 2) not within the exosite(s)-containing fragment comprising residues 1133-1547 (identical to SEQ ID NO:2). "PA 1-950" is a fragment of PAPP-A comprising amino acid residues 1-950. "PA 937-1547" is a fragment of PAPP-A comprising amino acid residues 937-1547. "PA 1-599" is a fragment of PAPP-A comprising amino acid residues 1-599.

| Mapping of PAC5 binding to PAPP-A | |
|---|---|
| PA 1-950 | binding |
| PA 937-1547 | no binding |
| PA 1-599 | no binding |

PAC5 is termed SEQ ID NO:7. Amino acid sequences of inhibitor PAC5 is given below. Sequences are full-length sequences of scFv PAC5 and is derived from cDNA. The sequences include His- and c-myc tags (both underlined). This His- and/or c-myc tag can be substituted with any other tag suitable for purification. Alternatively, His- and/or c-myc tag can be omitted from the sequence. The sequence further includes CDR (complementarity determining region) (marked in bold).

PAC5 sequence (SEQ ID NO:7):

EVQLLESGGGLVQPGGSLRLSCAASGFTFSSYAMSWVRQAPGKGLEWVSA

ISPAGVMTQYADSRFTISRDNSKNTLYLQMNSLRAEDTAVYYCAKQQGGF

DYWGQGTLVTVKGVSSGGGGSGGGGSGGGGSTDIQMTQSPSSLSASVGDR

VTITCRASQSISSYLNWYQQKPGKAPKLLIYRASALQSGVPSRFSGSGSG

TDFTLTISSLQPEDFATYYCQQPIARPPTFGQGTKVEIKRAAA<u>HHHHHH</u>G

<u>AAEQKLISEEDLNGAA</u>

Variants of SEQ ID NO:7 are described elsewhere in this document.

In one aspect the present invention provides isolated polypeptides that have a substantially similar sequence identity to the antibodies according to the present invention, such as PAC5, or an ortholog thereof.

The term "substantially similar sequence identity" is used herein to denote polypeptides having at least 70%, such as at least 72%, for example at least 74%, such as at least 76%, for example at least 78%, such as at least 80%, for example at least 82%, such as at least 84%, for example at least 86%, such as at least 88%, for example at least 90%, such as at least 91%, for example at least 92%, such as at least 93%, for example at least 94%, such as at least 95%, for example at least 96%, such as at least 97%, for example at least 98%, such as at least 99%, or greater than 99% sequence identity to SEQ ID NO:7 or an ortholog thereof.

The present invention further relates to the use of PAPP-A specific antibodies for use as a medicament.

The present invention also relates to the use of PAC5 for use as a medicament. The present invention also relates to methods for generation of PAC5. The method for generation of PAC5 can comprise one or more steps of: 1) PCR, 2) cloning, 3) generation of plasmid construct e.g. comprising a tag, 4) expression of protein in e.g. mammalian, bacterial or yeast cells, 5) expression and purification of protein.

The binding site of PAC5 cannot, unlike the binding sites of PAC1 and PAC2, be characterized as substrate binding PAPP-A exosites. However, the PAC5 data demonstrates that inhibition of PAPP-A can be obtained by targeting epitope(s) located in the sequence stretch between the proteolytic domain and CCP1. The mechanism of inhibition is probably steric hindrance.

The present invention also relates to PAC5 binding to PAPP-A that results in general inhibition of substrate proteolysis of known or unknown substrates. In one preferred embodiment, said inhibition is full or partial.

In another preferred embodiment the present invention also relates to PAC5 binding to PAPP-A that cause the general inhibition of one or more physiological substrate(s) of PAPP-A.

In another preferred embodiment PAC5 results in inhibition of IGFBP-4 and IGFBP-5 proteolysis. In yet another preferred embodiment the exosite inhibitor results in stimulation of IGF release.

Kit-of-Parts

In one preferred embodiment the present invention relates to a kit-of-parts comprising one or more exosite interactors.

In another embodiment the present invention relates to a kit-of-parts comprising one or more exosite inhibitors.

In another embodiment the present invention relates to a kit-of-parts comprising one or more exosite stimulators.

In one preferred embodiment the present invention relates to a kit-of-parts comprising one or more PAPP-A exosite(s) interactors.

In one preferred embodiment the present invention relates to a kit-of-parts comprising one or more PAPP-A exosite(s) inhibitors.

In one preferred embodiment the present invention relates to a kit-of-parts comprising one or more PAPP-A exosite(s) stimulators.

In another embodiment the present invention relates to a kit-of-parts comprising PAC1 and/or PAC2.

In yet another embodiment the present invention relates to a kit-of-parts comprising one or more variants of PAC1 and/or PAC2.

The term "Kit of parts" as used in the present invention provides the one or more exosite interactors according to the present invention and a second bioactive agent for administration in combination. The combined active substances may be used for simultaneous, sequential or separate administration. In all cases, it is preferred that any of the herein-mentioned medicaments and bioactive agents are administered in pharmaceutically effective amounts, i.e. an administration involving a total amount of each active component of the medicament or pharmaceutical composition or method that is sufficient to show a meaningful patient benefit. The formulations may conveniently be presented in unit dosage form by methods known to those skilled in the art. It is preferred that the kit may for example contain the active compounds in dosage forms for administration. A dosage form contains a sufficient amount of one or more of the active compound(s) such that a desirable effect can be obtained when administered to a subject. Thus, it is preferred that the medical packaging comprises an amount of dosage units corresponding to the relevant dosage regimen. Accordingly, in one embodiment, the medical packaging comprises a pharmaceutical composition comprising the compounds as defined above or a pharmaceutically acceptable salt thereof and pharmaceutically acceptable carriers, vehicles and/or excipients. The medical packaging may be in any suitable form—for example for enteral (via the digestive tract) or parenteral (routes other than the digestive tract) administration. In another preferred embodiment the packaging is in the form of a cartridge, such as a cartridge for an injection pen, the injection pen being such as an injection pen known from insulin treatment. Preferably, the kit-of-parts contains instructions indicating the use of the dosage form to achieve a desirable affect and the amount of dosage form to be taken over a specified time period. Accordingly, in one embodiment the medical packaging comprises instructions for administering the pharmaceutical composition. It is envisaged that at least one (such as 2 or 3) additional medicament(s) acting on hemostasis or on treatment on the underlying cause of hemostasis or risk hereof, and at least one (such as 2 or 3) polypeptide according to the present invention may be used for the manufacture of any of the "kit of parts" described herein for administration to an individual in need thereof.

Antibodies

It is one aspect of the present invention to provide antibodies or functional equivalents thereof specifically recognising and binding an epitope in SEQ ID NO:1, SEQ ID NO:2, SEQ ID NO:3OR SEQ ID NO:4 or a functional homologue thereof. The epitope may be any of the epitopes mentioned herein below.

The antibody or functional equivalent thereof may be any antibody known in the art, for example a polyclonal or a monoclonal antibody derived from a mammal or a synthetic antibody, such as a single chain antibody or hybrids comprising antibody fragments. Furthermore, the antibody may be mixtures of monoclonal antibodies or artificial polyclonal antibodies. In addition functional equivalents of antibodies may be antibody fragments, in particular epitope binding fragments. Furthermore, antibodies or functional equivalent thereof may be small molecule mimic, mimicking an antibody.

Naturally occurring antibodies are immunoglobulin molecules consisting of heavy and light chains. In preferred embodiments of the invention, the antibody is a monoclonal antibody.

Monoclonal antibodies (Mab's) are antibodies, wherein every antibody molecule are similar and thus recognises the same epitope. Monoclonal antibodies are in general produced by a hybridoma cell line. Methods of making monoclonal antibodies and antibody-synthesizing hybridoma cells are well known to those skilled in the art. Antibody producing hybridomas may for example be prepared by fusion of an antibody producing B lymphocyte with an immortalized B-lymphocyte cell line. Monoclonal antibodies according to the present invention may for example be prepared as described in Antibodies: A Laboratory Manual, By Ed Harlow and David Lane, *Cold Spring Harbor Laboratory Press*, 1988. Said monoclonal antibodies may be derived from any suitable mammalian species, however frequently the monoclonal antibodies will be rodent antibodies for example murine or rat monoclonal antibodies. It is preferred that the antibodies according to the present invention are monoclonal antibodies or derived from monoclonal antibodies.

Polyclonal antibodies is a mixture of antibody molecules recognising a specific given antigen, hence polyclonal antibodies may recognise different epitopes within said antigen. In general polyclonal antibodies are purified from serum of a mammal, which previously has been immunized with the antigen. Polyclonal antibodies may for example be prepared by any of the methods described in Antibodies: A Laboratory Manual, By Ed Harlow and David Lane, *Cold Spring Harbor Laboratory Press*, 1988. Polyclonal antibodies may be derived from any suitable mammalian species, for example from mice, rats, rabbits, donkeys, goats, sheep, cows or camels. The antibody is preferably not derived from a non-mammalian species, i.e. the antibody is for example preferably not a chicken antibody. The antibody may also for example be an artificial polyclonal antibody as for example described in U.S. Pat. No. 5,789,208 or U.S. Pat. No. 6,335,163, both patent specifications are hereby incorporated by reference into the application in their entirety.

The antibodies according to the present invention may also be recombinant antibodies. Recombinant antibodies are antibodies or fragments thereof or functional equivalents thereof produced using recombinant technology. For example recombinant antibodies may be produced using a synthetic library or by phage display. Recombinant antibodies may be produced according to any conventional method for example the methods outlined in "Recombinant Antibodies", Frank Breitling, Stefan Dübel, Jossey-Bass, September 1999.

The antibodies according to the present invention may also be bispecific antibodies, i.e. antibodies specifically recognising two different epitopes. Bispecific antibodies may in general be prepared starting from monoclonal antibodies, or from recombinant antibodies, for example by fusing two hybridomas in order to combine their specificity, by chemical crosslinking or using recombinant technologies. Antibodies according to the present invention may also be tri-specific antibodies.

Functional equivalents of antibodies may in one preferred embodiment be a fragment of an antibody, preferably an antigen binding fragment or a variable region. Examples of antibody fragments useful with the present invention include Fab, Fab', F(ab')$_2$ and Fv fragments. Papain digestion of antibodies produces two identical antigen binding fragments, called the Fab fragment, each with a single antigen binding site, and a residual "Fc" fragment, so-called for its ability to crystallize readily. Pepsin treatment yields an F(ab')$_2$ fragment that has two antigen binding fragments which are capable of cross-linking antigen, and a residual other fragment (which is termed pFc'). Additional fragments can include diabodies, linear antibodies, single-chain antibody molecules, and multispecific antibodies formed from antibody fragments. As used herein, "functional fragment" with respect to antibodies, refers to Fv, F(ab) and F(ab')$_{2i}$ fragments.

Preferred antibody fragments retain some or essential all the ability of an antibody to selectively bind with its antigen or receptor. Some preferred fragments are defined as follows:

(1) Fab is the fragment that contains a monovalent antigen-binding fragment of an antibody molecule. A Fab fragment can be produced by digestion of whole antibody with the enzyme papain to yield an intact light chain and a portion of one heavy chain.

(2) Fab' is the fragment of an antibody molecule and can be obtained by treating whole antibody with pepsin, followed by reduction, to yield an intact light chain and a portion of the heavy chain. Two Fab' fragments are obtained per antibody molecule. Fab' fragments differ from Fab fragments by the addition of a few residues at the carboxyl terminus of the heavy chain CH1 domain including one or more cysteines from the antibody hinge region.

(3) (Fab')$_2$ is the fragment of an antibody that can be obtained by treating whole antibody with the enzyme pepsin without subsequent reduction. F(ab')$_2$ is a dimer of two Fab' fragments held together by two disulfide bonds.

(4) Fv is the minimum antibody fragment that contains a complete antigen recognition and binding site. This region consists of a dimer of one heavy and one light chain variable domain in a tight, non-covalent association ($V_H$-$V_L$ dimer). It is in this configuration that the three CDRs of each variable domain interact to define an antigen binding site on the surface of the $V_H$-$V_L$ dimer. Collectively, the six CDRs confer antigen binding specificity to the antibody. However, even a single variable domain (or half of an Fv comprising only three CDRs specific for an antigen) has the ability to recognize and bind antigen, although at a lower affinity than the entire binding site.

In one embodiment of the present invention the antibody is a single chain antibody ("SCA"), defined as a genetically engineered molecule containing the variable region of the light chain, the variable region of the heavy chain, linked by a suitable polypeptide linker as a genetically fused single chain molecule. Such single chain antibodies are also referred to as "single-chain Fv" or "scFv" antibody fragments. Generally, the Fv polypeptide further comprises a polypeptide linker between the VH and VL domains that enables the scFv to form the desired structure for antigen binding.

The antibody may also be selected for useful properties, for example it may be desirable to control serum half life of the antibody. In general, complete antibody molecules have a very long serum persistence, whereas fragments (<60-80 kDa) are filtered very rapidly through the kidney. Glycosylation on complete antibodies in general, prolongs serum persistence. If long term action of the PAPP-A antibody is desirable, the PAPP-A antibody is preferably a complete antibody.

In another embodiment of the present invention the functional equivalent of an antibody is a small molecule mimic, mimicking an antibody.

Human Antibodies

Human monoclonal antibodies of the invention can be produced by a variety of techniques, including conventional monoclonal antibody methodology, e.g., the standard somatic cell hybridization technique of Kohler and Milstein, Nature 256:495 (1975). Although somatic cell hybridization procedures are preferred, in principle, other techniques for producing monoclonal antibody can be employed, e.g., viral or oncogenic transformation of B-lymphocytes or phage display techniques using libraries of human antibody genes.

In a preferred embodiment, human monoclonal antibodies directed against PAPP-A can be generated using transgenic or transchromosomal mice carrying parts of the human immune system rather than the mouse system. These transgenic and transchromosomic mice include mice referred to herein as HuMAb mice and KM mice, respectively, and are collectively referred to herein as "transgenic mice."

The HuMAb mouse contains a human immunoglobulin gene mini-loci that encodes un-rearranged human heavy (μ and γ) and κ light chain immunoglobulin sequences, together with targeted mutations that inactivate the endogenous p and K chain loci (Lonberg, N. et al. (1994) Nature 368 (6474): 856-859). Accordingly, the mice exhibit reduced expression of mouse IgM or K and in response to immunization, the introduced human heavy and light chain transgenes, undergo class switching and somatic mutation to generate high affinity human IgG,κ monoclonal antibodies (Lonberg, N. et al. (1994), supra; reviewed in Lonberg, N. (1994) Handbook of Experimental Pharmacology 113:49-101; Lonberg, N. and Huszar, D. (1995) Intern. Rev. Immunol. Vol. 13:65-93, and Harding, F. and Lonberg, N. (1995) Ann. N.Y. Acad. Sci. 764:536-546). The preparation of HuMAb mice is described in detail in Taylor, L. et al. (1992) Nucleic Acids Research 20:6287-6295; Chen, J. et al. (1993) International Immunology 5:647-656; Tuaillon et al. (1994) J. Immunol. 152:2912-2920; Lonberg et al., (1994) Nature 368(6474):856-859; Lonberg, N. (1994) Handbook of Experimental Pharmacology 113:49-101; Taylor, L. et al. (1994) International Immunology 6:579-591; Lonberg, N. and Huszar, D. (1995) Intern. Rev. Immunol. Vol. 13:65-93; Harding, F. and Lonberg, N. (1995) Ann. N.Y. Acad. Sci. 764:536-546; Fishwild, D. et al. (1996) Nature Biotechnology 14:845-851. See further, U.S. Pat. Nos. 5,545,806; 5,569,825; 5,625,126; 5,633,425; 5,789, 650; 5,877,397; 5,661,016; 5,814,318; 5,874,299; and 5,770, 429; all to Lonberg and Kay, as well as U.S. Pat. No. 5,545, 807 to Surani et al.; WO 98/24884, WO 94/25585, WO 93/1227, WO 92/22645, WO 92/03918 and WO 01/09187.

The KM mouse contains a human heavy chain transchromosome and a human kappa light chain transgene. The endogenous mouse heavy and light chain genes also have been disrupted in the KM mice such that immunization of the mice leads to production of human immunoglobulins rather than mouse immunoglobulins. Construction of KM mice and their use to raise human immunoglobulins is described in detail in WO 02/43478.

Immunizations

To generate fully human monoclonal antibodies to PAPP-A, transgenic or transchromosomal mice containing human immunoglobulin genes (e.g., HCo12, HCo7 or KM mice) can be immunized with an enriched preparation of PAPP-A antigen and/or cells expressing PAPP-A, as described, for example, by Lonberg et al. (1994), supra; Fishwild et al. (1996), supra, and WO 98/24884. Alternatively, mice can be immunized with DNA encoding human PAPP-A. Preferably, the mice will be 6-16 weeks of age upon the first infusion. For example, an enriched preparation (5-50 µg) of the PAPP-A antigen can be used to immunize the HuMAb mice intraperitoneally. In the event that immunizations using a purified or enriched preparation of the PAPP-A antigen do not result in antibodies, mice can also be immunized with cells expressing PAPP-A, e.g., a cell line, to promote immune responses.

Cumulative experience with various antigens has shown that the HuMAb transgenic mice respond best when initially immunized intraperitoneally (i.p.) or subcutaneously (s.c.) with PAPP-A expressing cells in complete Freund's adjuvant, followed by every other week i.p. immunizations (up to a total of 10) with PAPP-A-expressing cells in PBS. The immune response can be monitored over the course of the immunization protocol with plasma samples being obtained by retro-orbital bleeds. The plasma can be screened by FACS analysis, and mice with sufficient titers of anti-PAPP-A human immunoglobulin can be used for fusions. Mice can be boosted intravenously with PAPP-A expressing cells for example 4 and 3 days before sacrifice and removal of the spleen.

Generation of Hybridomas Producing Human Monoclonal Antibodies to PAPP-A

To generate hybridomas producing human monoclonal antibodies to human PAPP-A, splenocytes and lymph node cells from immunized mice can be isolated and fused to an appropriate immortalized cell line, such as a mouse myeloma cell line. The resulting hybridomas can then be screened for the production of antigen-specific antibodies. For example, single cell suspensions of splenic lymphocytes from immunized mice can be fused to SP2/0 non-secreting mouse myeloma cells (ATCC, CRL 1581) with 50% PEG (w/v). Cells can be plated at approximately $1 \times 10^5$ per well in flat bottom microtiter plate, followed by a two week incubation in selective medium containing besides usual reagents 10% fetal Clone Serum, 5-10% origen hybridoma cloning factor (IGEN) and 1×HAT (Sigma). After approximately two weeks, cells can be cultured in medium in which the HAT is replaced with HT. Individual wells can then be screened by ELISA for human kappa-light chain containing antibodies and by FACS analysis using PAPP-A-expressing cells for PAPP-A specificity. Once extensive hybridoma growth occurs, medium can be observed usually after 10-14 days. The antibody secreting hybridomas can be re-plated, screened again, and if still positive for human IgG, anti-PAPP-A monoclonal antibodies can be subcloned at least twice by limiting dilution. The stable subclones can then be cultured in vitro to generate antibody in tissue culture medium for characterization.

Generation of Transfectomas Producing Human Monoclonal Antibodies to PAPP-A

Human antibodies of the invention also can be produced in a host cell transfectoma using, for example, a combination of recombinant DNA techniques and gene transfection methods as is well known in the art, see e.g. Morrison, S. (1985) Science 229:1202. For example, to express the antibodies, or antibody fragments thereof, DNAs encoding partial or full-length light and heavy chains, can be obtained by standard molecular biology techniques (e.g., PCR amplification, site directed mutagenesis) and can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vectors or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_L$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel; Gene Expression Technology. Methods in Enzymology 185, Academic Press, San Diego, Calif. (1990). It will be appreciated by those skilled in the art that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP)) and polyoma. Alternatively, nonviral regulatory sequences may be used, such as the ubiquitin promoter.

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. No. 4,399,216, U.S. Pat. No. 4,634,665 and U.S. Pat. No. 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., elektroporation, calcium-phosphate precipitation, DEAE-dextran transfection, lipofectin transfection and the like.

In one embodiment the antibodies are expressed in eukaryotic cells, such as mammalian host cells. Preferred mammalian host cells for expressing the recombinant antibodies of the invention include CHO cells (including dhfr-CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *Mol. Biol.* 159:601-621), NS/0 myeloma cells, COS cells, HEK293 cells and SP2.0 cells. In particular for use with NS/0 myeloma cells, another preferred expression system is the GS (glutamine synthetase) gene expression system disclosed in WO 87/04462, WO 89/01036 and EP 338 841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Further Recombinant Means for Producing Human Monoclonal Antibodies to PAPP-A

Alternatively the cloned antibody genes can be expressed in other expression systems, including prokaryotic cells, such as microorganisms, e.g. *E. coli* for the production of scFv antibodies, algae, as well as insect cells. Furthermore, the antibodies can be produced in transgenic non-human animals, such as in milk from sheep and rabbits or eggs from hens, or in transgenic plants. See e.g. Verma, R., et al. (1998) "Antibody engineering: Comparison of bacterial, yeast, insect and mammalian expression systems", *J. Immunol. Meth.* 216:165-181; Pollock, et al. (1999) "Transgenic milk as a method for the production of recombinant antibodies", *J. Immunol. Meth.* 231:147-157; and Fischer, R., et al. (1999) "Molecular farming of recombinant antibodies in plants", *Biol. Chem.* 380:825-839.

Use of Partial Antibody Sequences to Express Intact Antibodies

Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al. (1998) *Nature* 332:323-327; Jones, P. et al. (1986) *Nature* 321:522-525; and Queen, C. et al. (1989) *Proc. Natl. Acad. Sci. USA* 86:10029-10033). Such framework sequences can be obtained from public DNA databases that include germline antibody gene sequences. These germline sequences will differ from mature antibody gene sequences because they will not include completely assembled variable genes, which are formed by V(D)J joining during B cell maturation. Germline gene sequences will also differ from the sequences of a high affinity secondary repertoire antibody which contains mutations throughout the variable gene but typically clustered in the CDRs. For example, somatic mutations are relatively infrequent in the amino terminal portion of framework region 1 and in the carboxy-terminal portion of framework region 4. For this reason, it is not necessary to obtain the entire DNA sequence of a particular antibody in order to recreate an intact recombinant antibody having binding properties similar to those of the original antibody (see WO 99/45962). Partial heavy and light chain sequence spanning the CDR regions is typically sufficient for this purpose. The partial sequence is used to determine which germline variable and joining gene segments contributed to the recombined antibody variable genes. The germline sequence is then used to fill in missing portions of the variable regions. Heavy and light chain leader sequences are cleaved during protein maturation and do not contribute to the properties of the final antibody. To add missing sequences, cloned cDNA sequences can be combined with synthetic oligonucleotides by ligation or PCR amplification. Alternatively, the entire variable region can be synthesized as a set of short, overlapping, oligonucleotides and combined by PCR amplification to create an entirely synthetic variable region clone. This process has certain advantages such as elimination or inclusion or particular restriction sites, or optimization of particular codons.

The nucleotide sequences of heavy and light chain transcripts from hybridomas are used to design an overlapping set of synthetic oligonucleotides to create synthetic V sequences with identical amino acid coding capacities as the natural sequences. The synthetic heavy and kappa chain sequences can differ from the natural sequences in three ways: strings of repeated nucleotide bases are interrupted to facilitate oligonucleotide synthesis and PCR amplification; optimal translation initiation sites are incorporated according to Kozak's rules (Kozak, 1991, J. Biol. Chem. 266:19867-19870); and HindIII sites are engineered upstream of the translation initiation sites.

For both the heavy and light chain variable regions, the optimized coding and corresponding non-coding, strand sequences are broken down into 30-50 nucleotides approximately at the midpoint of the corresponding non-coding oligonucleotide. Thus, for each chain, the oligonucleotides can be assembled into overlapping double stranded sets that span segments of 150-400 nucleotides. The pools are then used as templates to produce PCR amplification products of 150-400 nucleotides. Typically, a single variable region oligonucleotide set will be broken down into two pools which are separately amplified to generate two overlapping PCR products. These overlapping products are then combined by PCR amplification to form the complete variable region. It may also be desirable to include an overlapping fragment of the heavy or light chain constant region (including the BbsI site of the kappa light chain, or the AgeI site of the gamma heavy chain) in the PCR amplification to generate fragments that can easily be cloned into the expression vector constructs.

The reconstructed heavy and light chain variable regions are then combined with cloned promoter, leader, translation initiation, constant region, 3' untranslated, polyadenylation, and transcription termination, sequences to form expression vector constructs. The heavy and light chain expression constructs can be combined into a single vector, co-transfected, serially transfected, or separately transfected into host cells which are then fused to form a host cell expressing both chains.

In another aspect of the invention, the structural features of the human anti-PAPP-A antibodies of the invention are used to create structurally related human anti-PAPP-A antibodies that retain at least one functional property of the antibodies of the invention, such as binding to PAPP-A. More specifically, one or more CDR regions of 2C6 can be combined recombinantly with known human framework regions and CDRs to create additional, recombinantly-engineered, human anti-PAPP-A antibodies of the invention.

Monovalent Antibodies

The monospecific binding member may be monovalent, i.e. having only one binding domain.

For a monovalent antibody, the immunoglobulin constant domain amino acid residue sequences comprise the structural portions of an antibody molecule known in the art as CH1, CH2, CH3 and CH4. Preferred are those binding members which are known in the art as $C_L$. Preferred $C_L$ polypeptides are selected from the group consisting of $C_{kappa}$ and $C_{lambda}$.

Furthermore, insofar as the constant domain can be either a heavy or light chain constant domain ($C_H$ or $C_L$, respectively), a variety of monovalent binding member compositions are contemplated by the present invention. For example, light chain constant domains are capable of disulfide bridging to either another light chain constant domain, or to a heavy chain constant domain. In contrast, a heavy chain constant domain can form two independent disulfide bridges, allowing for the possibility of bridging to both another heavy chain and to a light chain, or to form polymers of heavy chains.

Thus, in another embodiment, the invention contemplates a composition comprising a monovalent polypeptide wherein the constant chain domain C has a cysteine residue capable of forming at least one disulfide bridge, and where the composition comprises at least two monovalent polypeptides covalently linked by said disulfide bridge.

In preferred embodiments, the constant chain domain C can be either $C_L$ or $C_H$. Where C is $C_L$, the $C_L$ polypeptide is preferably selected from the group consisting of $C_{kappa}$ and $C_{lambda}$.

In another embodiment, the invention contemplates a binding member composition comprising a monovalent polypeptide as above except where C is $C_L$ having a cysteine residue capable of forming a disulfide bridge, such that the composition contains two monovalent polypeptides covalently linked by said disulfide bridge.

Antibodies: Multispecificity, Including Bispecificity

In a preferred embodiment the present invention relates to multispecific binding members, which have affinity for and are capable of binding at least two different entities. Multispecific binding members can include bispecific binding members.

In one embodiment the multispecific molecule is a bispecific antibody (BsAb), which carries at least two different binding domains, at least one of which is of antibody origin.

A bispecific molecule of the invention can also be a single chain bispecific molecule, such as a single chain bispecific antibody, a single chain bispecific molecule comprising one single chain antibody and a binding domain, or a single chain bispecific molecule comprising two binding domains. Multispecific molecules can also be single chain molecules or may comprise at least two single chain molecules.

The multispecific, including bispecific, antibodies may be produced by any suitable manner known to the person skilled in the art.

The traditional approach to generate bispecific whole antibodies was to fuse two hybridoma cell lines each producing an antibody having the desired specificity. Because of the random association of immunoglobulin heavy and light chains, these hybrid hybridomas produce a mixture of up to 10 different heavy and light chain combinations, only one of which is the bispecific antibody. Therefore, these bispecific antibodies have to be purified with cumbersome procedures, which considerably decrease the yield of the desired product.

Alternative approaches include in vitro linking of two antigen specificities by chemical cross-linking of cysteine residues either in the hinge or via a genetically introduced C-terminal Cys as described above. An improvement of such in vitro assembly was achieved by using recombinant fusions of Fab's with peptides that promote formation of heterodimers. However, the yield of bispecific product in these methods is far less than 100%.

A more efficient approach to produce bivalent or bispecific antibody fragments, not involving in vitro chemical assembly steps, was described by Holliger et al. (1993). This approach takes advantage of the observation that scFv's secreted from bacteria are often present as both monomers and dimers. This observation suggested that the $V_H$ and $V_L$ of different chains could pair, thus forming dimers and larger complexes. The dimeric antibody fragments, also named "diabodies" by Hollinger et al., are in fact small bivalent antibody fragments that assembled in vivo. By linking the $V_H$ and VL of two different antibodies 1 and 2, to form "cross-over" chains $V_H$1VL 2 and $V_H$ 2-VL 1, the dimerisation process was shown to reassemble both antigen-binding sites. The affinity of the two binding sites was shown to be equal to the starting scFv's, or even to be 10-fold increased when the polypeptide linker covalently linking $V_H$ and VL was removed, thus generating two proteins each consisting of a $V_H$ directly and covalently linked to a VL not pairing with the $V_H$. This strategy of producing bispecific antibody fragments was also described in several patent applications. Patent application WO 94/09131 (SCOTGEN LTD; priority date Oct. 15, 1992) relates to a bispecific binding protein in which the binding domains are derived from both a $V_H$ and a VL region either present at two chains or linked in a scFv, whereas other fused antibody domains, e.g. C-terminal constant domains, are used to stabilise the dimeric constructs. Patent application WO 94/13804 (CAMBRIDGE ANTIBODY TECHNOLOGY/MEDICAL RESEARCH COUNCIL; first priority date Dec. 4, 1992) relates to a polypeptide containing a $V_H$ and a VL which are incapable of associating with each other, whereby the V-domains can be connected with or without a linker.

Mallender and Voss, 1994 (also described in patent application WO 94/13806; DOW CHEMICAL CO; priority date Dec. 11, 1992) reported the in vivo production of a single-chain bispecific antibody fragment in E. coli. The bispecificity of the bivalent protein was based on two previously produced monovalent scFv molecules possessing distinct specificities, being linked together at the genetic level by a flexible polypeptide linker. Traditionally, whenever single-chain antibody fragments are referred to, a single molecule consisting of one heavy chain linked to one (corresponding) light chain in the presence or absence of a polypeptide linker is implicated. When making bivalent or bispecific antibody fragments through the "diabody" approach (Holliger et al., (1993) and patent application WO 94/09131) or by the "double scFv" approach (Mallender and Voss, 1994 and patent application WO 94/13806), again the $V_H$ is linked to a (the corresponding) VL.

The multispecific molecules described above can be made by a number of methods. For example, all specificities can be encoded in the same vector and expressed and assembled in the same host cell. This method is particularly useful where the multispecific molecule is a mAb×mAb, mAb×Fab, Fab×F(ab')$_2$ or ligand×Fab fusion protein. Various other methods for preparing bi- or multivalent antibodies are described for example described in U.S. Pat. Nos. 5,260,203; 5,455,030; 4,881,175; 5,132,405; 5,091,513; 5,476,786; 5,013,653; 5,258,498; and 5,482,858.

By using a bispecific or multispecific binding member according to the invention the invention offers several advantages as compared to monospecific/monovalent binding members.

A bispecific/multispecific binding member has a first binding domain capable of specifically recognising and binding a *Streptococcus* protein, in particular Pneumolysin, whereas the other binding domain(s) may be used for other purposes:

In one embodiment at least one other binding domain is used for binding to a *Streptococcus* protein, such as binding to another epitope on the same *Streptococcus* protein as compared to the first binding domain. Thereby specificity for the *Streptococcus* species may be increased as well as increase of avidity of the binding member.

In another embodiment the at least one other binding domain may be used for specifically binding a mammalian cell, such as a human cell. It is preferred that the at least other binding domain is capable of binding an immunoactive cell, such as a leukocyte, a macrophage, a lymphocyte, a basophilic cell, and/or an eosinophilic cell, in order to increase the effect of the binding member in a therapeutic method. This may be accomplished by establishing that the at least one other binding domain is capable of specifically binding a mammalian protein, such as a human protein, such as a protein selected from any of the cluster differentiation proteins (CD), in particular CD64 and/or CD89. A method for producing bispecific antibodies having CD64 specificity is described in U.S. Pat. No. 6,071,517 to Medarex, Inc.

Accordingly, the present invention includes bispecific and multispecific molecules comprising at least one first-binding specificity for PAPP-A and a second binding specificity for a second target epitope. In a particular embodiment of the invention, the second target epitope is an Fc receptor, e.g., human FcγRI (CD64) or a human Fcα receptor (CD89), or a T cell receptor, e.g., CD3. Therefore, the invention includes bispecific and multispecific molecules capable of binding both to FcγR, FcαR or FcεR expressing effector cells (e.g., monocytes, macrophages or polymorphonuclear cells (PMNs)), and to target cells expressing PAPP-A. These bispecific and multispecific molecules target PAPP-A expressing cells to effector cell and, like the human monoclonal antibodies of the invention, trigger Fc receptor-mediated effector cell activities, such as phagocytosis of PAPP-A expressing cells, antibody dependent cellular cytotoxicity (ADCC), cytokine release, or generation of superoxide anion.

Bispecific and multispecific molecules of the invention can further include a third binding specificity, in addition to an anti-Fc binding specificity and an anti-PAPP-A binding specificity. In one embodiment, the third binding specificity is an anti-enhancement factor (EF) portion, e.g., a molecule which binds to a surface protein involved in cytotoxic activity and thereby increases the immune response against the target cell. The "anti-enhancement factor portion" can be an antibody, functional antibody fragment or a ligand that binds to a given molecule, e.g., an antigen or a receptor, and thereby results in an enhancement of the effect of the binding determinants for the Fc receptor or target cell antigen. The "anti-enhancement factor portion" can bind an Fc receptor or a target cell antigen. Alternatively, the anti-enhancement factor portion can bind to an entity that is different from the entity to which the first and second binding specificities bind. For example, the anti-enhancement factor portion can bind a cytotoxic T cell (e.g., via CD2, CD3, CD8, CD28, CD4, CD40, ICAM-1 or other immune cell that results in an increased immune response against the target cell).

In one embodiment, the bispecific and multispecific molecules of the invention comprise as a binding specificity at least one further antibody, including, e.g., an Fab, Fab', F(ab')$_2$, Fv, or a single chain Fv. The antibody may also be a light chain or heavy chain dimer, or any minimal fragment thereof such as a Fv or a single chain construct as described in Ladner et al. in U.S. Pat. No. 4,946,778. The antibody may also be a binding-domain immunoglobulin fusion protein as disclosed in US 2003/0118592 and US 2003/0133939.

In one embodiment, the binding specificity for an Fc receptor is provided by a human monoclonal antibody, the binding of which is not blocked by human immunoglobulin G (IgG). As used herein, the term "IgG receptor" refers to any of the eight γ-chain genes located on chromosome 1. These genes encode a total of twelve transmembrane or soluble receptor isoforms which are grouped into three Fcγ receptor classes: FcγRI (CD64), FcγRII (CD32), and FcγRII (CD16). In one preferred embodiment, the Fcγ receptor is a human high affinity FcγRI.

The production and characterisation of these preferred monoclonal antibodies are described by Fanger et al. in WO 88/00052 and in U.S. Pat. No. 4,954,617. These antibodies bind to an epitope of FcγRI, FcγRII or FcγRII at a site which is distinct from the Fcγ binding site of the receptor and, thus, their binding is not blocked substantially by physiological levels of IgG. Specific anti-FcγRI antibodies useful in this invention are mAb 22, mAb 32, mAb 44, mAb 62 and mAb 197. In other embodiments, the anti-Fcγ receptor antibody is a humanized form of mAb 22 (H22). The production and characterization of the H22 antibody is described in Graziano, R. F. et al. (1995) *J. Immunol.* 155 (10):4996-5002 and WO 94/10332. The H22 antibody producing cell line was deposited at the American Type Culture Collection on Nov. 4, 1992 under the designation HA022CL1 and has the accession No. CRL 11177.

In still other preferred embodiments, the binding specificity for an Fc receptor is provided by an antibody that binds to a human IgA receptor, e.g., an Fcα receptor (Fcα1 (CD89)), the binding of which is preferably not blocked by human immunoglobulin A (IgA). The term "IgA receptor" is intended to include the gene product of one α-gene (FcαRI) located on chromosome 19. This gene is known to encode several alternatively spliced transmembrane isoforms of 55 to 110 kDa. FcαRI (CD89) is constitutively expressed on monocytes/macrophages, eosinophilic and neutrophilic granulocytes, but not on non-effector cell populations. FcαRI has medium affinity for both IgA1 and IgA2, which is increased upon exposure to cytokines such as G-CSF or GM-CSF (Morton, H. C. et al. (1996) *Critical Reviews in Immunology* 16:423-440). Four FcαRI-specific monoclonal antibodies, identified as A3, A59, A62 and A77, which bind FcαRI outside the IgA ligand binding domain, have been described (Monteiro, R. C. et al. (1992) *J. Immunol.* 148:1764).

While human monoclonal antibodies are preferred, other antibodies which can be employed in the bispecific or multispecific molecules of the invention are murine, chimeric and humanized monoclonal antibodies. Such murine, chimeric and humanized monoclonal antibodies can be prepared by methods known in the art. Bispecific and multispecific molecules of the present invention can be made using chemical techniques (see e.g., D. M. Kranz et al. (1981) *Proc. Natl. Acad. Sci. USA* 78:5807), "polydoma" techniques (see U.S. Pat. No. 4,474,893), or recombinant DNA techniques.

In particular, bispecific and multispecific molecules of the present invention can be prepared by conjugating the constituent binding specificities, e.g., the anti-FcR and anti-PAPP-A binding specificities, using methods known in the art. For example, each binding specificity of the bispecific and multispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-5-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl)cyclohexane-1-carboxylate (sulfo-SMCC) see e.g., Karpovsky et al. (1984) *J. Exp. Med.* 160:1686; Liu, M. A., et al. (1985) *Proc. Natl. Acad. Sci. USA* 82:8648. Other methods include those described by Paulus (Behring Ins. Mitt. (1985) No. 78, 118-132); Brennan et al. (1985) *Science* 229:81-83, and Glennie et al. (1987) *J. Immunol.* 139:2367-2375. Preferred conjugating agents are SATA and sulfo-SMCC, both available from Pierce Chemical Co. (Rockford, Ill.).

When the binding specificities are antibodies, they can be conjugated via sulfhydryl bonding of the C-terminus hinge regions of the two heavy chains. In a particularly preferred embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific and multispecific molecule is a mAb×mAb, mAb×Fab, Fab×F(ab')$_2$ or ligand×Fab fusion protein. A bispecific and multispecific molecule of the invention, e.g., a bispecific molecule can be a single chain molecule, such as a single chain bispecific antibody, a single chain bispecific molecule comprising one single chain antibody and a binding determinant, or a single chain bispecific molecule comprising two binding determinants. Bispecific and multispecific molecules can also be single chain molecules or may comprise at least two single chain molecules. Methods for preparing bi- and multispecific molecules are described for example in U.S. Pat. No. 5,260,203; U.S. Pat. No. 5,455,030; U.S. Pat. No. 4,881,175; U.S. Pat. No. 5,132,405; U.S. Pat. No. 5,091,513; U.S. Pat. No. 5,476,786; U.S. Pat. No. 5,013,653; U.S. Pat. No. 5,258,498; and U.S. Pat. No. 5,482,858.

Binding of the bispecific and multispecific molecules to their specific targets can be confirmed by enzyme-linked immunosorbent assay (ELISA), a radioimmunoassay (RIA), FACS analysis, a bioassay (e.g., growth inhibition), or a Western Blot Assay. Each of these assays generally detects the presence of protein-antibody complexes of particular interest by employing a labelled reagent (e.g., an antibody) specific for the complex of interest. For example, the FcR-antibody complexes can be detected using e.g., an enzyme-linked antibody or antibody fragment which recognizes and specifically binds to the antibody-FcR complexes. Alternatively, the complexes can be detected using any of a variety of other immunoassays. For example, the antibody can be radioactively labelled and used in a radioimmunoassay (RIA) (see, for example, Weintraub, B., Principles of Radioimmunoassays, Seventh Training Course on Radioligand Assay Techniques, The Endocrine Society, March, 1986). The radioactive isotope can be detected by such means as the use of a γ counter or a scintillation counter or by autoradiography.

Humanised Antibody Framework

It is not always desirable to use non-human antibodies for human therapy, since the non-human "foreign" epitopes may elicit immune response in the individual to be treated. To eliminate or minimise the problems associated with non-human antibodies, it is desirable to engineer chimeric antibody derivatives, i.e., "humanized" antibody molecules that combine the non-human Fab variable region binding determinants with a human constant region (Fc). Such antibodies are characterised by equivalent antigen specificity and affinity of the monoclonal and polyclonal antibodies described above, and are less immunogenic when administered to humans, and therefore more likely to be tolerated by the individual to be treated.

Accordingly, in one embodiment the binding member has a binding domain carried on a humanised antibody framework, also called a humanised antibody.

Humanised antibodies are in general chimeric antibodies comprising regions derived from a human antibody and regions derived from a non-human antibody, such as a rodent antibody. Humanisation (also called Reshaping or CDR-grafting) is a well-established technique for reducing the immunogenicity of monoclonal antibodies (mAbs) from xenogeneic sources (commonly rodent), increasing the homology to a human immunoglobulin, and for improving their activation of the human immune system. Thus, humanized antibodies are typically human antibodies in which some CDR residues and possibly some framework residues are substituted by residues from analogous sites in rodent antibodies.

It is further important that humanized antibodies retain high affinity for the antigen and other favourable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of certain residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is maximized, although it is the CDR residues that directly and most substantially influence antigen binding.

One method for humanising MAbs related to production of chimeric antibodies in which an antigen binding site comprising the complete variable domains of one antibody are fused to constant domains derived from a second antibody, preferably a human antibody. Methods for carrying out such chimerisation procedures are for example described in EP-A-0 120 694 (Celltech Limited), EP-A-0 125 023 (Genentech Inc.), EP-A-0 171 496 (Res. Dev. Corp. Japan), EP-A-0173494 (Stanford University) and EP-A-0 194 276 (Celltech Limited). A more complex form of humanisation of an antibody involves the re-design of the variable region domain so that the amino acids constituting the non-human antibody binding site are integrated into the framework of a human antibody variable region (Jones et al., 1986).

The humanized antibody of the present invention may be made by any method capable of replacing at least a portion of a CDR of a human antibody with a CDR derived from a non-human antibody. Winter describes a method which may be used to prepare the humanized antibodies of the present invention (UK Patent Application GB 2188638A, filed on Mar. 26, 1987), the contents of which is expressly incorporated by reference. The human CDRs may be replaced with non-human CDRs using oligonucleotide site-directed mutagenesis as described in the examples below.

As an example the humanized antibody of the present invention may be made as described in the brief explanation below. The humanized antibodies of the present invention may be produced by the following process:
(a) constructing, by conventional techniques, an expression vector containing an operon with a DNA sequence encoding an antibody heavy chain in which the CDRs and such minimal portions of the variable domain framework region that are required to retain antibody binding specificity are derived from a non-human immunoglobulin, and the remaining parts of the antibody chain are derived from a human immunoglobulin, thereby producing the vector of the invention;
(b) constructing, by conventional techniques, an expression vector containing an operon with a DNA sequence encoding a complementary antibody light chain in which the CDRs and such minimal portions of the variable domain framework region that are required to retain donor antibody binding specificity are derived from a non-human immunoglobulin, and the remaining parts of the antibody chain are derived from a human immunoglobulin, thereby producing the vector of the invention;
(c) transfecting the expression vectors into a host cell by conventional techniques to produce the transfected host cell of the invention; and
(d) culturing the transfected cell by conventional techniques to produce the humanised antibody of the invention.

The host cell may be cotransfected with the two vectors of the invention, the first vector containing an operon encoding a light chain derived polypeptide and the second vector containing an operon encoding a heavy chain derived polypeptide. The two vectors contain different selectable markers, but otherwise, apart from the antibody heavy and light chain coding sequences, are preferably identical, to ensure, as far as possible, equal expression of the heavy and light chain polypeptides. Alternatively, a single vector may be used, the vector including the sequences encoding both the light and the heavy chain polypeptides. The coding sequences for the light and heavy chains may comprise cDNA or genomic DNA or both.

The host cell used to express the altered antibody of the invention may be either a bacterial cell such as *Escherichia coli*, or a eukaryotic cell. In particular a mammalian cell of a well defined type for this purpose, such as a myeloma cell or a Chinese hamster ovary cell may be used.

The general methods by which the vectors of the invention may be constructed, transfection methods required to produce the host cell of the invention and culture methods required to produce the antibody of the invention from such host cells are all conventional techniques. Likewise, once produced, the humanized antibodies of the invention may be purified according to standard procedures as described below.

Human Antibody Framework

In a more preferred embodiment the invention relates to a binding member, wherein the binding domain is carried by a human antibody framework, i.e. wherein the antibodies have a greater degree of human peptide sequences than do humanised antibodies.

Human mAb antibodies directed against human proteins can be generated using transgenic mice carrying the complete human immune system rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906, Kucherlapati et al. PCT publication WO 91/10741; Lonberg et al. International Application WO 92/03918; Kay et al. International Application 92/03917; Lonberg, N. et al. 1994 Nature 368:856-859; Green, L. L. et al. 1994 Nature Genet. 7:13-21; Morrison, S. L. et al. 1994 Proc. Natl. Acad. Sci. USA 81:6851-6855; Bruggeman et al. 1993 Year Immunol 7:33-40; Tuaillon et al. 1993 PNAS 90:3720-3724; Bruggeman et al. 1991 Eur J Immunol 21:1323-1326).

Such transgenic mice are available from Abgenix, Inc., Fremont, Calif., and Medarex, Inc., Annandale, N.J. It has been described that the homozygous deletion of the antibody heavy-chain joining region (1H) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., Proc. Natl. Acad. Sci. USA 90:2551 (1993); Jakobovits et al., Nature 362:255-258 (1993); Bruggermann et al., Year in Immunol. 7:33 (1993); and Duchosal et al. Nature 355:258 (1992). Human antibodies can also be derived from phage-display libraries (Hoogenboom et al., J. Mol. Biol. 227: 381 (1991); Marks et al., J. Mol. Biol. 222:581-597 (1991); Vaughan, et al., Nature Biotech 14:309 (1996)).

Alternative "Binding Members"

Natural single domain antibodies. Heavy-chain antibodies (HCAbs) are naturally produced by camelids (camels, dromedaries and llamas). HCAbs are homodimers of heavy chains only, devoid of light chains and the first constant domain (Hamers-Casterman et al., 1993). The possibility to immunise these animals allows for the cloning, selection and production of an antigen binding unit consisting of a single-domain only. Furthermore these minimal-sized antigen binding fragments are well expressed in bacteria, interact with the antigen with high affinity and are very stable.

New or Nurse Shark Antigen Receptor (NAR) protein exists as a dimer of two heavy chains with no associated light chains. Each chain is composed of one variable (V) and five constant domains. The NAR proteins constitute a single immunoglobulin variable-like domain (Greenberg, A. S., Avila, D., Hughes, M., Hughes, A., McKinney, E. C. & Flajnik, M. F. (1995) Nature (London) 374, 168-173.) which is much lighter than an antibody molecule.

Non-immunoglobulin binding members. In one preferred embodiment, the present invention relates to binding members derived from a naturally occurring protein or polypeptide; said protein or polypeptide may for example be designed de novo, or may be selected from a library. The binding member may be a single moiety, e.g., a polypeptide or protein domain, or it may include two or more moieties, e.g., a pair of polypeptides. The binding member may for example, but exclusively, be a lipocalin, a single chain MHC molecule, an Anticalin™ (Pieris), an Affibody™, or a Trinectin™ (Phylos), Nanobodies (Ablynx). The binding member may be selected or designed by recombinant methods known by people well known in the art.

Affibodies are produced recombinantly by methods well known to those skilled in the art of recombinant DNA technology. Phage display techniques may be used to identify affibodies capable of specifically recognising a particular antigen. Affibodies can be produced in any suitable host, as for example, but not exclusively *E. coli* or *S. cerevisiae* (se below) (Hansson M et al., "An in vitro selected binding protein (affibody) shows conformation-dependent recognition of the respiratory syncytial virus (RSV) G protein", Immunotechnology. 1999 March; 4(3-4): 237-52.)

Affibody-antibody chimeras. In another embodiment of the present invention, said binding member is an affibody-antibody chimera (Ronnmark J et al, Construction and characterization of affibody-Fc chimeras produced in *Escherichia coli*. J Immunol Methods. 2002 Mar. 1; 261(1-2): 199-211). According to the invention affibody-antibody chimeras can be constructed by several methods, for example by fusion of nucleotide sequences or fusion of polypeptide sequences. The nucleic acid sequence of an affibody maybe fused to a nucleic acid sequence of an antibody by DNA recombinant technology for the production of the binding member in a suitable host. The affibody nucleotide sequences may for example be fused to an antibody light chain nucleotide sequence or an antibody heavy chain nucleic acid sequence. In an embodiment of the invention the affibody sequence may be fused with a fragment of an antibody sequence. The affibody sequence may for example, but not exclusively, be fused with an Fc fragment of an antibody, thus potentially allowing dimers to form by homo-dimerisation. The affibody antibody chimeras may contain multiple affibody sequences, such as at least two, three, four of at least six affibody sequences. In an embodiment of the invention a fusion of two affibodies may be fused with an Fc fragment resulting in a tetravalent binding member upon dimerisation.

Alternatively the chimeras may be obtained by linking of the two protein/polypeptide molecules together by methods known to people skilled in the art.

Polypeptides

General Methods for the Production of Polypeptides According to the Present Invention A polypeptide with SEQ ID NO:1, SEQ ID NO:2, SEQ ID NO:3, SEQ ID NO:4, SEQ ID NO:5, SEQ ID NO:6 or SEQ ID NO:7 or any variant thereof described elsewhere in this document can be generated by one or more of the methods described below.

The polypeptides of the present invention, including full-length polypeptides, functional fragments, and fusion proteins, can be produced in recombinant host cells following conventional techniques. To express a gene according to the present invention, a nucleic acid molecule encoding the polypeptide must be operably linked to regulatory sequences that control transcriptional expression in an expression vector and then introduced into a host cell. In addition to transcriptional regulatory sequences, such as promoters and enhancers, expression vectors can include translational regulatory sequences and a marker gene, which is suitable for selection of cells that carry the expression vector.

The host cells which may comprise the polypeptide according to the invention can be exemplified by animal cells, mammalian cells, insect cells, fungal cells, yeast cells, bacterial cells and plant cells.

Expression vectors that are suitable for production of a foreign protein in eukaryotic cells typically contain (1) prokaryotic DNA elements coding for a bacterial replication origin and an antibiotic resistance marker to provide for the growth and selection of the expression vector in a bacterial host; (2) eukaryotic DNA elements that control initiation of transcription, such as a promoter; and (3) DNA elements that control the processing of transcripts, such as a transcription termination/polyadenylation sequence. As discussed above, expression vectors can also include nucleotide sequences encoding a secretory sequence that directs the heterologous polypeptide into the secretory pathway of a host cell. For example, an expression vector may comprise a gene according to the present invention and a secretory sequence derived from said gene or another secreted gene.

Examples of vectors commonly used with bacteria include the pET series (Novagen), pGEX series (Ge Healthcare), pBAD-series (Invitrogen). Examples of vectors in yeasts are the pPic series for *Pichia* (Invitrogen), the pKlac system from *Kluyveromyces lactis* (New England biolabs), *S. cereviseae* vectors (Patel, O., Fearnley, R., and Macreadie, I. 3002. *Saccharomyces cerevisiae* expression vectors with thrombin-cleavable N- and C-terminal 6× (His) tags. Biotechnol Lett. 2003 25(4):331-334) and the pYes system for *S. cereviseae* (Invitrogen). Examples of vectors for use in fungi are the pBAR series (described in Pall, M. L. and J. Brunelli. 1993. A series of six compact fungal transformation vectors containing polylinkers with unique restrictions sites. Fungal Genetics Newsletter 40: 59-61). The pIEx plasmid based system (Merck) or the baculovirus based system (Merck) are two examples of systems useful for insect cells. Similar products are available from other companies.

Examples of vectors for use in insect cells include the tetracycline regulated systems pTet and pTre, the adenovirus-based system Adeno-X, the retrovirus-based system Rethro-X (all Clontech) and the pcDNA vectors (Invitrogen). Again, many more examples exist and are on the market.

Polypeptides according to the present invention may be expressed in mammalian cells. Examples of suitable mammalian host cells include African green monkey kidney cells (Vero; ATCC CRL 1587), human embryonic kidney cells (293-HEK; ATCC CRL 1573), baby hamster kidney cells (BHK-21, BHK-570; ATCC CRL 8544, ATCC CRL 10314), canine kidney cells (MDCK; ATCC CCL 34), Chinese hamster ovary cells (CHO-K1; ATCC CCL61; CHO DG44 [Chasin et al., Som. Cell. Molec. Genet. 12:555 1986]), rat pituitary cells (GH1; ATCC CCL82), HeLa S3 cells (ATCC CCL2.2), rat hepatoma cells (H-4-II-E; ATCC CRL 1548) SV40-transformed monkey kidney cells (COS-1; ATCC CRL 1650) and murine embryonic cells (NIH-3T3; ATCC CRL 1658).

Mammalian hosts cells used for expressing the polypeptides according to the present invention is by no means intended as a process for modifying the germ line genetic identity of human beings, as only immortalized or transformed diploid human cells are described in this process.

For a mammalian host, the transcriptional and translational regulatory signals may be derived from viral sources, such as adenovirus, bovine papilloma virus, simian virus, or the like, in which the regulatory signals are associated with a particular gene which has a high level of expression. Suitable transcriptional and translational regulatory sequences also can be obtained from mammalian genes, such as actin, collagen, myosin, and metallothionein genes.

Transcriptional regulatory sequences include a promoter region sufficient to direct the initiation of RNA synthesis. Suitable eukaryotic promoters include the promoter of the mouse metallothionein I gene (Hamer et al., J. Molec. Appl. Genet. 1:273 (1982)), the TK promoter of Herpes virus (McKnight, Cell 31:355 (1982)), the SV40 early promoter (Benoist et al., Nature 290:304 (1981)), the Rous sarcoma virus promoter (Gorman et al., Proc. Nat'l Acad. Sci. USA 79:6777 (1982)), the cytomegalovirus promoter (Foecking et al., Gene 45:101 (1980)), and the mouse mammary tumor virus promoter (see, generally, Etcheverry, "Expression of Engineered Proteins in Mammalian Cell Culture," in Protein Engineering: Principles and Practice, Cleland et al. (eds.), pages 163 181 (John Wiley & Sons, Inc. 1996)).

Alternatively, a prokaryotic promoter, such as the bacteriophage T3 RNA polymerase promoter, can be used to control gene expression in mammalian cells if the prokaryotic promoter is regulated by a eukaryotic promoter (Zhou et al., Mol. Cell. Biol. 10:4529 (1990), and Kaufman et al., Nucl. Acids Res. 19:4485 (1991)).

An expression vector can be introduced into host cells using a variety of standard techniques including calcium phosphate transfection, liposome-mediated transfection, microprojectile-mediated delivery, electroporation, and the like. The transfected cells can be selected and propagated to provide recombinant host cells that comprise the expression vector stably integrated in the host cell genome. Techniques for introducing vectors into eukaryotic cells and techniques for selecting such stable transformants using a dominant selectable marker are described, for example, by Ausubel (1995) and by Murray (ed.), Gene Transfer and Expression Protocols (Humana Press 1991).

For example, one suitable selectable marker is a gene that provides resistance to the antibiotic neomycin. In this case, selection is carried out in the presence of a neomycin-type drug, such as G-418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A suitable amplifiable selectable marker is dihydrofolate reductase, which confers resistance to methotrexate. Other drug resistance genes (e.g., hygromycin resistance, multi-drug resistance, puromycin acetyltransferase) can also be used. Alternatively, markers that introduce an altered phenotype, such as green fluorescent protein, or cell surface proteins such as CD4, CD8, Class I MHC, placental alkaline phosphatase may be used to sort transfected cells from untransfected cells by such means as FACS sorting or magnetic bead separation technology.

Polypeptides according to the present invention can also be produced by cultured mammalian cells using a viral delivery system. Exemplary viruses for this purpose include adenovirus, herpesvirus, vaccinia virus and adeno-associated virus (AAV). Adenovirus, a double-stranded DNA virus, is currently the best studied gene transfer vector for delivery of heterologous nucleic acid (for a review, see Becker et al., Meth. Cell Biol. 43:161 (1994), and Douglas and Curiel, Science & Medicine 4:44 (1997)). Advantages of the adenovirus system include the accommodation of relatively large DNA inserts, the ability to grow to high-titer, the ability to infect a broad range of mammalian cell types, and flexibility that allows use with a large number of available vectors containing different promoters.

By deleting portions of the adenovirus genome, larger inserts (up to 7 kb) of heterologous DNA can be accommodated. These inserts can be incorporated into the viral DNA by direct ligation or by homologous recombination with a co-transfected plasmid. An option is to delete the essential E1 gene from the viral vector, which results in the inability to replicate unless the E1 gene is provided by the host cell. Adenovirus vector-infected human 293 cells (ATCC Nos. CRL-1573, 45504, 45505), for example, can be grown as adherent cells or in suspension culture at relatively high cell density to produce significant amounts of protein (see Garnier et al., Cytotechnol. 15:145 (1994)).

The baculovirus system provides an efficient means to introduce cloned genes according to the present invention into insect cells. Suitable expression vectors are based upon the *Autographa californica* multiple nuclear polyhedrosis virus (AcMNPV), and contain well-known promoters such as *Drosophila* heat shock protein (hsp) 70 promoter, *Autographa californica* nuclear polyhedrosis virus immediate-early gene promoter (ie-1) and the delayed early 39K promoter, baculovirus p10 promoter, and the *Drosophila* metallothionein promoter. A second method of making recombinant baculovirus utilizes a transposon-based system described by Luckow (Luckow, et al., J. Virol. 67:4566 (1993)). This system, which utilizes transfer vectors, is sold in the BAC-to-BAC kit (Life Technologies, Rockville, Md.). This system utilizes a transfer vector, PFASTBAC (Life Technologies) containing a Tn7 transposon to move the DNA encoding the polypeptide according to the present invention into a baculovirus genome maintained in *E. coli* as a large plasmid called a "bacmid." See, Hill-Perkins and Possee, J. Gen. Virol. 71:971 (1990), Bonning, et al., J. Gen. Virol. 75:1551 (1994), and Chazenbalk, and Rapoport, J. Biol. Chem. 270:1543 (1995). In addition, transfer vectors can include an in-frame fusion with DNA encoding an epitope tag at the C- or N-terminus of the expressed polypeptide according to the present invention, for example, a Glu-Glu epitope tag (Grussenmeyer et al., Proc. Nat'l Acad. Sci. 82:7952 (1985)). Using a technique known in the art, a transfer vector containing a gene according to the present invention is transformed into *E. coli*, and screened for bacmids, which contain an interrupted lacZ gene indicative of recombinant baculovirus. The bacmid DNA containing the recombinant baculovirus genome is then isolated using common techniques.

The illustrative PFASTBAC vector can be modified to a considerable degree. For example, the polyhedrin promoter can be removed and substituted with the baculovirus basic protein promoter (also known as Pcor, p6.9 or MP promoter) which is expressed earlier in the baculovirus infection, and has been shown to be advantageous for expressing secreted proteins (see, for example, Hill-Perkins and Possee, J. Gen. Virol. 71:971 (1990), Bonning, et al., J. Gen. Virol. 75:1551 (1994), and Chazenbalk and Rapoport, J. Biol. Chem. 270: 1543 (1995). In such transfer vector constructs, a short or long version of the basic protein promoter can be used. Moreover, transfer vectors can be constructed which replace the native secretory signal sequences of polypeptides according to the present invention with secretory signal sequences derived from insect proteins. For example, a secretory signal sequence from Ecdysteroid Glucosyltransferase (EGT), honey bee Melittin (Invitrogen Corporation; Carlsbad, Calif.), or baculovirus gp67 (PharMingen: San Diego, Calif.) can be used in constructs to replace native secretory signal sequences.

The recombinant virus or bacmid is used to transfect host cells. Suitable insect host cells include cell lines derived from IPLB-Sf-21, a *Spodoptera frugiperda* pupal ovarian cell line, such as Sf9 (ATCC CRL 1711), Sf21AE, and Sf21 (Invitrogen Corporation; San Diego, Calif.), as well as *Drosophila* Schneider-2 cells, and the HIGH FIVEO cell line (Invitrogen) derived from *Trichoplusia ni* (U.S. Pat. No. 5,300,435). Commercially available serum-free media can be used to grow and to maintain the cells. Suitable media are Sf900 II™ (Life Technologies) or ESF921™ (Expression Systems) for Sf9 cells; and Ex-cellO405™ (JRH Biosciences, Lenexa, Kans.) or Express FiveO™ (Life Technologies) for *T. ni* cells. When recombinant virus is used, the cells are typically grown up from an inoculation density of approximately 2 to $5 \times 10^5$ cells to a density of 1 to $2 \times 10^6$ cells at which time a recombinant viral stock is added at a multiplicity of infection (MOI) of 0.1 to 10, more typically near 3.

Established techniques for producing recombinant proteins in baculovirus systems are provided by Bailey et al., "Manipulation of Baculovirus Vectors," in Methods in Molecular Biology, Volume 7: Gene Transfer and Expression Protocols, Murray (ed.), pages 147 168 (The Humana Press, Inc. 1991), by Patel et al., "The baculovirus expression system," in DNA Cloning 2: Expression Systems, 2nd Edition, Glover et al. (eds.), pages 205 244 (Oxford University Press 1995), by Ausubel (1995) at pages 16 37 to 16 57, by Richardson (ed.), Baculovirus Expression Protocols (The Humana Press, Inc. 1995), and by Lucknow, "Insect Cell Expression Technology," in Protein Engineering: Principles and Practice, Cleland et al. (eds.), pages 183 218 (John Wiley & Sons, Inc. 1996).

Fungal cells, including yeast cells, can also be used to express the genes described herein. Yeast species of particular interest in this regard include *Saccharomyces cerevisiae, Pichia pastoris,* and *Pichia methanolica*. Suitable promoters for expression in yeast include promoters from GAL1 (galactose), PGK (phosphoglycerate kinase), ADH (alcohol dehydrogenase), AOX1 (alcohol oxidase), HIS4 (histidinol dehydrogenase), and the like. Many yeast cloning vectors have been designed and are readily available. These vectors include Yip-based vectors, such as YIp5, YRp vectors, such as YRp17, YEp vectors such as YEp13 and YCp vectors, such as YCp19. Methods for transforming *S. cerevisiae* cells with exogenous DNA and producing recombinant polypeptides therefrom are disclosed by, for example, Kawasaki, U.S. Pat. No. 4,599,311, Kawasaki et al., U.S. Pat. No. 4,931,373, Brake, U.S. Pat. No. 4,870,008, Welch et al., U.S. Pat. No. 5,037,743, and Murray et al., U.S. Pat. No. 4,845,075. Transformed cells are selected by phenotype determined by the selectable marker, commonly drug resistance or the ability to grow in the absence of a particular nutrient (e.g., leucine). A suitable vector system for use in *Saccharomyces cerevisiae* is the POT1 vector system disclosed by Kawasaki et al. (U.S. Pat. No. 4,931,373), which allows transformed cells to be selected by growth in glucose-containing media. Additional suitable promoters and terminators for use in yeast include those from glycolytic enzyme genes (see, e.g., Kawasaki, U.S. Pat. No. 4,599,311, Kingsman et al., U.S. Pat. No. 4,615, 974, and Bitter, U.S. Pat. No. 4,977,092) and alcohol dehydrogenase genes. See also U.S. Pat. Nos. 4,990,446, 5,063, 154, 5,139,936, and 4,661,454. Other examples of commonly used and/or commercially available vectors suitable for use in yeast are the pPic series (Invitrogen), the pKlac system from *Kluyveromyces lactis* (New England Biolabs) and *S. cerevisiae* vectors (Patel et al., Biotechnology letters 2003 vol 25(4):331-334) as well as the pYes system for *S. cerevisiae* (Invitrogen). In fungi, the pBAR series is useful (Pall et al., 1993 vol. 40:59-61, Functional Genetics Newsletter).

Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillermondii* and *Candida maltosa* are known in the art. See, for example, Gleeson et al., J. Gen. Microbiol. 132:3459 (1986), and Cregg, U.S. Pat. No. 4,882,279. *Aspergillus* cells may be utilized according to the methods of McKnight et al., U.S. Pat. No. 4,935,349. Methods for transforming *Acremonium chrysogenum* are disclosed by Sumino et al., U.S. Pat. No. 5,162,228.

Methods for transforming *Neurospora* are disclosed by Lambowitz, U.S. Pat. No. 4,486,533.

For example, the use of *Pichia methanolica* as host for the production of recombinant proteins is disclosed by Raymond, U.S. Pat. No. 5,716,808, Raymond, U.S. Pat. No. 5,736,383, Raymond et al., Yeast 14:11 23 (1998), and in international publication Nos. WO 97/17450, WO 97/17451, WO 98/02536, and WO 98/02565. DNA molecules for use in transforming *P. methanolica* will commonly be prepared as double-stranded, circular plasmids, which can be linearized prior to transformation. For polypeptide production in *P. methanolica*, the promoter and terminator in the plasmid can be that of a *P. methanolica* gene, such as a *P. methanolica* alcohol utilization gene (AUG1 or AUG2). Other useful promoters include those of the dihydroxyacetone synthase (DHAS), formate dehydrogenase (FMD), and catalase (CAT) genes. To facilitate integration of the DNA into the host chromosome, it is preferred to have the entire expression segment of the plasmid flanked at both ends by host DNA sequences. A suitable selectable marker for use in *Pichia methanolica* is a *P. methanolica* ADE2 gene, which encodes phosphoribosyl-5-aminoimidazole carboxylase (AIRC; EC 4.1.1.21), and which allows ade2 host cells to grow in the absence of adenine. For large-scale, industrial processes where it is desirable to minimize the use of methanol, it is possible to use host cells in which both methanol utilization genes (AUG1 and AUG2) are deleted. For production of secreted proteins, host cells can be used that are deficient in vacuolar pro tease genes (PEP4 and PRB1). Electroporation is used to facilitate the introduction of a plasmid containing DNA encoding a polypeptide of interest into *P. methanolica* cells. *P. methanolica* cells can be transformed by electroporation using an exponentially decaying, pulsed electric field having a field strength of from 2.5 to 4.5 kV/cm, preferably about 3.75 kV/cm, and a time constant (t) of from 1 to 40 milliseconds, most preferably about 20 milliseconds.

Expression vectors can also be introduced into plant protoplasts, intact plant tissues, or isolated plant cells. Methods for introducing expression vectors into plant tissue include the direct infection or co-cultivation of plant tissue with *Agrobacterium tumefaciens*, microprojectile-mediated delivery, DNA injection, electroporation, and the like. See, for example, Horsch et al., Science 227:1229 (1985), Klein et al., Biotechnology 10:268 (1992), and Miki et al., "Procedures for Introducing Foreign DNA into Plants," in Methods in Plant Molecular Biology and Biotechnology, Glick et al. (eds.), pages 67 88 (CRC Press, 1993).

Alternatively, genes according to the present invention can be expressed in prokaryotic host cells. Suitable promoters that can be used to express polypeptides according to the present invention in a prokaryotic host are well-known to those of skill in the art and include promoters capable of recognizing the T4, T3, Sp6 and T7 polymerases, the $P_R$ and $P_L$ promoters of bacteriophage lambda, the trp, recA, heat shock, lacUV5, tac, Ipp-lacSpr, phoA, and lacZ promoters of *E. coli*, promoters of *B. subtilis*, the promoters of the bacteriophages of *Bacillus, Streptomyces* promoters, the int promoter of bacteriophage lambda, the bla promoter of pBR322, and the CAT promoter of the chloramphenicol acetyl transferase gene. Prokaryotic promoters have been reviewed by Glick, J. Ind. Microbiol. 1:277 (1987), Watson et al., Molecular Biology of the Gene, 4th Ed. (Benjamin Cummins 1987), and by Ausubel et al. (1995).

Suitable prokaryotic hosts include *E. coli* and *Bacillus subtilis*. Suitable strains of *E. coli* include BL21(DE3), BL21 (DE3)pLysS, BL21(DE3)pLysE, DH1, DH41, DH5, DH51, DH51F, DH51MCR, DH10B, DH10B/p3, DH11S, C600, HB101, JM101, JM105, JM109, JM110, K38, RR1, Y1088, Y1089, CSH18, ER1451, and ER1647 (see, for example, Brown (ed.), Molecular Biology Labfax (Academic Press 1991)). Suitable strains of *Bacillus subtilis* include BR151, YB886, MI119, MI120, and B170 (see, for example, Hardy, "*Bacillus* Cloning Methods," in DNA Cloning: A Practical Approach, Glover (ed.) (IRL Press 1985)).

When expressing a polypeptide according to the present invention in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the protein, thereby obviating the need for denaturation and refolding.

Methods for expressing proteins in prokaryotic hosts are well-known to those of skill in the art (see, for example, Williams et al., "Expression of foreign proteins in *E. coli* using plasmid vectors and purification of specific polyclonal antibodies," in DNA Cloning 2: Expression Systems, 2nd Edition, Glover et al. (eds.), page 15 (Oxford University Press 1995), Ward et al., "Genetic Manipulation and Expression of Antibodies," in Monoclonal Antibodies: Principles and Applications, page 137 (Wiley-Liss, Inc. 1995), and Georgiou, "Expression of Proteins in Bacteria," in Protein Engineering: Principles and Practice, Cleland et al. (eds.), page 101 (John Wiley & Sons, Inc. 1996)).

Standard methods for introducing expression vectors into bacterial, yeast, insect, and plant cells are provided, for example, by Ausubel (1995).

General methods for expressing and recovering foreign protein produced by a mammalian cell system are provided by, for example, Etcheverry, "Expression of Engineered Proteins in Mammalian Cell Culture," in Protein Engineering: Principles and Practice, Cleland et al. (eds.), pages 163 (Wiley-Liss, Inc. 1996). Standard techniques for recovering protein produced by a bacterial system is provided by, for example, Grisshammer et al., "Purification of over-produced proteins from *E. coli* cells," in DNA Cloning 2: Expression Systems, 2nd Edition, Glover et al. (eds.), pages 59 92 (Oxford University Press 1995). Established methods for isolating recombinant proteins from a baculovirus system are described by Richardson (ed.), Baculovirus Expression Protocols (The Humana Press, Inc. 1995).

As an alternative, polypeptides of the present invention can be synthesized by exclusive solid phase synthesis, partial solid phase methods, fragment condensation or classical solution synthesis. These synthesis methods are well-known to those of skill in the art (see, for example, Merrifield, J. Am. Chem. Soc. 85:2149 (1963), Stewart et al., "Solid Phase Peptide Synthesis" (2nd Edition), (Pierce Chemical Co. 1984), Bayer and Rapp, Chem. Pept. Prot. 3:3 (1986), Atherton et al., Solid Phase Peptide Synthesis: A Practical Approach (IRL Press 1989), Fields and Colowick, "Solid-Phase Peptide Synthesis," Methods in Enzymology Volume 289 (Academic Press 1997), and Lloyd-Williams et al., Chemical Approaches to the Synthesis of Peptides and Proteins (CRC Press, Inc. 1997)). Variations in total chemical synthesis strategies, such as "native chemical ligation" and "expressed protein ligation" are also standard (see, for example, Dawson et al., Science 266:776 (1994), Hackeng et al., Proc. Nat'l Acad. Sci. USA 94:7845 (1997), Dawson, Methods Enzymol. 287: 34 (1997), Muir et al, Proc. Nat'l Acad. Sci. USA 95:6705 (1998), and Severinov and Muir, J. Biol. Chem. 273:16205 (1998)).

The present invention contemplates compositions comprising a peptide or polypeptide described herein. Such compositions can further comprise a carrier. The carrier can be a conventional organic or inorganic carrier. Examples of carriers include water, buffer solution, alcohol, propylene glycol, macrogol, sesame oil, corn oil, and the like.

Isolation of Polypeptides According to the Present Invention

The polypeptides of the present invention (SEQ ID NO:1, SEQ ID NO:2, SEQ ID NO:3, SEQ ID NO:4, SEQ ID NO:5, SEQ ID NO:6 or SEQ ID NO:7 or any variant thereof described elsewhere in this document) can be purified to at least about 80% purity, to at least about 90% purity, to at least about 95% purity, or even greater than 95% purity with respect to contaminating macromolecules, particularly other proteins and nucleic acids, and free of infectious and pyrogenic agents. The polypeptides of the present invention can also be purified to a pharmaceutically pure state, which is greater than 99.9% pure. In certain preparations, a purified polypeptide is substantially free of other polypeptides, particularly other polypeptides of animal origin.

Fractionation and/or conventional purification methods can be used to obtain preparations of polypeptides according to the present invention purified from natural sources, and recombinant polypeptides according to the present invention and fusion polypeptides according to the present invention purified from recombinant host cells. In general, ammonium sulfate precipitation and acid or chaotrope extraction may be used for fractionation of samples. Exemplary purification steps may include hydroxyapatite, size exclusion, FPLC and reverse-phase high performance liquid chromatography. Suitable chromatographic media include derivatized dextrans, agarose, cellulose, polyacrylamide, specialty silicas, and the like. PEI, DEAE, QAE and Q derivatives are preferred. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties.

Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers. Selection of a particular method for polypeptide isolation and purification is a matter of routine design and is determined in part by the properties of the chosen support. See, for example, Affinity Chromatography: Principles & Methods (Pharmacia LKB Biotechnology 1988), and Doonan, Protein Purification Protocols (The Humana Press 1996).

Additional variations in the isolation and purification of polypeptides according to the present invention can be devised by those of skill in the art. For example, specific antibodies recognizing polypeptides according to the present invention and fragments thereof, obtained as described below, can be used to isolate large quantities of protein by immunoaffinity purification.

The polypeptides of the present invention can also be isolated by exploitation of particular properties. For example, immobilized metal ion adsorption (IMAC) chromatography can be used to purify histidine-rich proteins, including those comprising polyhistidine tags. Briefly, a gel is first charged with divalent metal ions to form a chelate (Sulkowski, Trends in Biochem. 3:1 (1985)). Histidine-rich proteins will be adsorbed to this matrix with differing affinities, depending upon the metal ion used, and will be eluted by competitive elution, lowering the pH, or use of strong chelating agents. Other methods of purification include purification of glycosylated proteins by lectin affinity chromatography and ion exchange chromatography (M. Deutscher, (ed.), Meth. Enzymol. 182:529 (1990)). Within additional embodiments of the invention, a fusion of the polypeptide of interest and an affinity tag (e.g., maltose-binding protein, an immunoglobulin domain) may be constructed to facilitate purification.

Polypeptides and fragments thereof according to the present invention may also be prepared through chemical synthesis, as described above. Polypeptides according to the present invention may be monomers or multimers; glycosylated or non-glycosylated; pegylated or non-pegylated; and may or may not include an initial methionine amino acid residue.

Sequence Homologies

In one aspect the present invention provides naturally occurring or isolated polypeptides that have a substantially similar sequence identity to the polypeptides according to the present invention, such as SEQ ID NO:1, SEQ ID NO:2, SEQ ID NO:3, SEQ ID NO:4, SEQ ID NO:5, SEQ ID NO:6 or SEQ ID NO:7, or an ortholog thereof.

The term "substantially similar sequence identity" is used herein to denote polypeptides having at least 70%, such as at least 72%, for example at least 74%, such as at least 76%, for example at least 78%, such as at least 80%, for example at least 82%, such as at least 84%, for example at least 86%, such as at least 88%, for example at least 90%, such as at least 91%, for example at least 92%, such as at least 93%, for example at least 94%, such as at least 95%, for example at least 96%, such as at least 97%, for example at least 98%, such as at least 99%, or greater than 99% sequence identity to SEQ ID NO:1, SEQ ID NO:2, SEQ ID NO:3, SEQ ID NO:4, SEQ ID NO:5, SEQ ID NO:6 or SEQ ID NO:7 or an ortholog thereof.

In another embodiment, the term "substantially similar sequence identity" is used herein to denote polypeptides having at least 80% sequence identity, such as at least 81% sequence identity, e.g. at least 82% sequence identity, such as at least 83% sequence identity, e.g. at least 84% sequence identity, such as at least 85% sequence identity, e.g. at least 86% sequence identity, such as at least 87% sequence identity, e.g. at least 88% sequence identity, such as at least 89% sequence identity, e.g. at least 90% sequence identity, such as at least 91% sequence identity, e.g. at least 92% sequence identity, such as at least 93% sequence identity, e.g. at least 94% sequence identity, such as at least 95% sequence identity, e.g. at least 96% sequence identity, such as at least 97% sequence identity, e.g. at least 98% sequence identity, such as at least 99% sequence identity, e.g. at least 99.5% sequence identity to SEQ ID NO:1, SEQ ID NO:2, SEQ ID NO:3, SEQ ID NO:4, SEQ ID NO:5, SEQ ID NO:6 or SEQ ID NO:7 or an ortholog thereof.

In yet another embodiment, the term "substantially similar sequence identity" is used herein to denote polypeptide containing less than 99.5%, such as less than 98%, e.g. less than 97%, such as less than 96%, e.g. less than 95%, such as less than 94%, e.g. less than 93%, such as less than 92%, e.g. less than 91%, such as less than 90%, e.g. less than 88%, such as less than 86%, e.g. less than 84%, e.g. less than 82%, such as less than 80%, e.g. less than 75%, such as less than 70%, e.g. less than 65%, such as less than 60%, e.g. less than 55%, such as less than 50%, e.g. less than 45%, such as less than 40%, e.g. less than 35%, such as less than 30%, e.g. less than 25%, such as less than 20%, such as less than 15%, e.g. less than 10% of the amino acid residues of SEQ ID NO:1, SEQ ID NO:2, SEQ ID NO:3, SEQ ID NO:4, SEQ ID NO:5, SEQ ID NO:6 or SEQ ID NO:7 or an ortholog thereof.

In one embodiment, the polypeptide according to SEQ ID NO:1 is a fragment, wherein the fragment contains less than 1547 consecutive amino acid residues, such as less than 1530 consecutive amino acid residues, e.g. less than 1510 consecutive amino acid residues, such as less than 1490 consecutive amino acid residues, e.g. less than 1470 consecutive amino acid residues, such as less than 1450 consecutive amino acid residues, e.g. less than 1430 consecutive amino acid residues, such as less than 1410 consecutive amino acid residues, e.g. less than 1390 consecutive amino acid residues, such as less than 1370 consecutive amino acid residues, e.g. less than 1350 consecutive amino acid residues, such as less than 1330 consecutive amino acid residues, e.g. less than 1310 consecutive amino acid residues, such as less than 1290 consecutive amino acid residues, e.g. less than 1270 consecutive amino acid residues, such as less than 1250 consecutive amino acid residues, e.g. less than 1230 consecutive amino acid residues, such as less than 1210 consecutive amino acid residues, e.g. less than 1190 consecutive amino acid residues, such as less than 1170 consecutive amino acid residues, e.g. less than 1150 consecutive amino acid residues, such as less than 1130 consecutive amino acid residues, e.g. less than 1110 consecutive amino acid residues, such as less than 1090 consecutive amino acid residues, e.g. less than 1070 consecutive amino acid residues, such as less than 1050 consecutive amino acid residues, e.g. less than 1030 consecutive amino acid residues, such as less than 1010 consecutive amino acid residues, e.g. less than 990 consecutive amino acid residues, such as less than 970, e.g. less than 950 consecutive amino acid residues, such as less than 930 consecutive amino acid residues e.g. less than 910 consecutive amino acid residues, such as less than 890 consecutive amino acid residues, e.g. less than 870 consecutive amino acid residues, such as less than 850 consecutive amino acid residues, e.g. less than 830 consecutive amino acid residues, such as less than 810 consecutive amino acid residues, e.g. less than 790 consecutive amino acid residues, such as less than 770 consecutive amino acid residues, e.g. less than 750 consecutive amino acid residues, such as less than 730 consecutive amino acid residues, e.g. less than 710 consecutive amino acid residues, such as less than 690 consecutive amino acid residues, e.g. less than 670 consecutive amino acid residues, such as less than 650 consecutive amino acid residues, e.g. less than 630 consecutive amino acid residues, such as less than 610 consecutive amino acid residues, e.g. less than 590 consecutive amino acid residues, such as less than 570 consecutive amino acid residues, e.g. less than 550 consecutive amino acid residues, such as less than 530 consecutive amino acid residues, e.g. less than 510 consecutive amino acid residues, such as less than 490 consecutive amino acid residues, e.g. less than 470 consecutive amino acid residues, such as less than 450 consecutive amino acid residues, e.g. less than 430 consecutive amino acid residues, such as less than 410 consecutive amino acid residues, e.g. less than 390 consecutive amino acid residues, such as less than 370 consecutive amino acid residues, e.g. less than 350 consecutive amino acid residues, such as less than 330, e.g. less than 310 consecutive amino acid residues, such as less than 290 consecutive amino acid residues e.g. less than 270 consecutive amino acid residues, such as less than 250 consecutive amino acid residues, e.g. less than 230 consecutive amino acid residues, such as less than 210 consecutive amino acid residues, e.g. less than 190 consecutive amino acid residues, such as less than 170 consecutive amino acid residues, e.g. less than 150 consecutive amino acid residues, such as less than 130 consecutive amino acid residues, e.g. less than 110 consecutive amino acid residues, such as less than 90 consecutive amino acid residues, e.g. less than 70 consecutive amino acid residues, such as less than 50 consecutive amino acid residues, e.g. less than 30 consecutive amino acid residues of SEQ ID NO:1.

In another embodiment, the polypeptide according to SEQ ID NO:1 is a fragment, wherein the fragment contains 6 or more consecutive amino acid residues, such as 7 or more consecutive amino acid residues, e.g. 8 or more consecutive amino acid residues, such as 9 or more consecutive amino acid residues, e.g. 10 or more consecutive amino acid residues, such as 12 or more consecutive amino acid residues, e.g. 14 or more consecutive amino acid residues, such as 16 or more consecutive amino acid residues, e.g. 18 or more consecutive amino acid residues, such as 20 or more consecutive amino acid residues, e.g. 22 or more consecutive amino acid residues, such as 24 or more consecutive amino acid residues, e.g. 26 or more consecutive amino acid residues, such as 28 or more consecutive amino acid residues, e.g. 30 or more consecutive amino acid residues of SEQ ID NO:1.

In one embodiment, the polypeptide according to SEQ ID NO:2 is a fragment, wherein the fragment contains less than 415 consecutive amino acid residues, such as less than 410 consecutive amino acid residues, e.g. less than 405 consecutive amino acid residues, such as less than 400 consecutive amino acid residues, e.g. less than 395 consecutive amino acid residues, such as less than 390 consecutive amino acid residues, e.g. less than 385 consecutive amino acid residues, such as less than 380 consecutive amino acid residues, e.g. less than 375 consecutive amino acid residues, such as less than 370 consecutive amino acid residues, e.g. less than 365 consecutive amino acid residues, such as less than 360 consecutive amino acid residues, e.g. less than 355 consecutive amino acid residues, such as less than 350 consecutive amino acid residues, e.g. less than 345 consecutive amino acid residues, such as less than 340 consecutive amino acid residues, e.g. less than 335 consecutive amino acid residues, such as less than 330 consecutive amino acid residues, e.g. less than 325 consecutive amino acid residues, such as less than 320 consecutive amino acid residues, e.g. less than 315 consecutive amino acid residues, such as less than 310 consecutive amino acid residues, e.g. less than 305 consecutive amino acid residues, such as less than 300 consecutive amino acid residues, e.g. less than 295 consecutive amino acid residues, such as less than 290 consecutive amino acid residues, e.g. less than 285 consecutive amino acid residues, such as less than 280 consecutive amino acid residues, e.g. less than 275 consecutive amino acid residues, such as less than 270, e.g. less than 265 consecutive amino acid residues, such as less than 260 consecutive amino acid residues e.g. less than 255 consecutive amino acid residues, such as less than 250 consecutive amino acid residues, e.g. less than 245 consecutive amino acid residues, such as less than 240 consecutive amino acid residues, e.g. less than 235 consecutive amino acid residues, such as less than 230 consecutive amino acid residues, e.g. less than 225 consecutive amino acid residues, such as less than 220 consecutive amino acid residues, e.g. less than 215 consecutive amino acid residues, such as less than 210 consecutive amino acid residues, e.g. less than 205 consecutive amino acid residues, such as less than 200 consecutive amino acid residues, e.g. less than 195 consecutive amino acid residues, such as less than 190 consecutive amino acid residues, e.g. less than 185 consecutive amino acid residues, such as less than 180 consecutive amino acid residues, e.g. less than 175 consecutive amino acid residues, such as less than 170 consecutive amino acid residues, e.g. less than 165 consecutive amino acid residues, such as less than 160 consecutive amino acid residues, e.g. less than 155 consecutive amino acid residues, such as less than 150 consecutive amino acid residues, e.g. less than 145 consecutive amino acid residues, such as less than 140 consecutive amino acid residues, e.g. less than 135 consecutive amino acid residues, such as less than 130 consecutive amino acid residues, e.g. less than 125 consecutive amino acid residues, such as less than 120 consecutive amino acid residues, e.g. less than 115 consecutive amino acid residues, such as less than 110, e.g. less than 105 consecutive amino acid residues, such as less than 100 consecutive amino acid residues e.g. less than 95 consecutive amino acid residues, such as less than 90 consecutive amino acid residues, e.g. less than 85 consecutive amino acid residues, such as less than 80 consecutive amino acid residues, e.g. less than 75 consecutive amino acid residues, such as less than 70 consecutive amino acid residues, e.g. less than 65 consecutive amino acid residues, such as less than 60 consecutive amino acid residues, e.g. less than 55 consecutive amino acid residues, such as less than 50 consecutive amino acid residues, e.g. less than 45 consecutive amino acid residues, such as less than 40 consecutive amino acid residues, e.g. less than 35 consecutive amino acid residues, such as less than 30 consecutive amino acid residues of SEQ ID NO:2.

In another embodiment, the polypeptide according to SEQ ID NO:2 is a fragment, wherein the fragment contains 6 or more consecutive amino acid residues, such as 7 or more consecutive amino acid residues, e.g. 8 or more consecutive amino acid residues, such as 9 or more consecutive amino acid residues, e.g. 10 or more consecutive amino acid residues, such as 12 or more consecutive amino acid residues, e.g. 14 or more consecutive amino acid residues, such as 16 or more consecutive amino acid residues, e.g. 18 or more consecutive amino acid residues, such as 20 or more consecutive amino acid residues, e.g. 22 or more consecutive amino acid residues, such as 24 or more consecutive amino acid residues, e.g. 26 or more consecutive amino acid residues, such as 28 or more consecutive amino acid residues, e.g. 30 or more consecutive amino acid residues of SEQ ID NO:2.

In one embodiment, the polypeptide according to SEQ ID NO:3 is a fragment, wherein the fragment contains less than 70 consecutive amino acid residues of, such as less than 65 consecutive amino acid residues, e.g. less than 60 consecutive amino acid residues, such as less than 55 consecutive amino acid residues, e.g. less than 50 consecutive amino acid residues, such as less than 45 consecutive amino acid residues, e.g. less than 40 consecutive amino acid residues, such as less than 35 consecutive amino acid residues, e.g. less than 30 consecutive amino acid residues, such as less than 25 consecutive amino acid residues, e.g. less than 20 consecutive amino acid residues of SEQ ID NO:3.

In another embodiment, the polypeptide according to SEQ ID NO:3 is a fragment, wherein the fragment contains 6 or more consecutive amino acid residues, such as 7 or more consecutive amino acid residues, e.g. 8 or more consecutive amino acid residues, such as 9 or more consecutive amino acid residues, e.g. 10 or more consecutive amino acid residues, such as 12 or more consecutive amino acid residues, e.g. 14 or more consecutive amino acid residues, such as 16 or more consecutive amino acid residues, e.g. 18 or more consecutive amino acid residues, such as 20 or more consecutive amino acid residues, e.g. 22 or more consecutive amino acid residues, such as 24 or more consecutive amino acid residues, e.g. 26 or more consecutive amino acid residues, such as 28 or more consecutive amino acid residues, e.g. 30 or more consecutive amino acid residues of SEQ ID NO:3.

The present invention also contemplates variant nucleic acid molecules that can be identified using two criteria: a) a determination of the identity or similarity between a polypeptide having the amino acid sequence of SEQ ID NO:1, SEQ ID NO:2, SEQ ID NO:3, SEQ ID NO:4, SEQ ID NO:5, SEQ ID NO:6 or SEQ ID NO:7, and b) a hybridization assay carried out under stringent conditions. For example, certain gene variants comprise polynucleotides that remain hybridized with a polynucleotide encoding a polypeptide according to the present invention, such as SEQ ID NO:1, SEQ ID NO:2, SEQ ID NO:3, SEQ ID NO:4, SEQ ID NO:5, SEQ ID NO:6 or SEQ ID NO:7, or a complement of such a polynucleotide, following washing under stringent washing conditions, in which the wash stringency is equivalent to 0.5× to 2×SSC with 0.1% SDS at 55° C. to 65° C. Alternatively, variant genes can be characterized as nucleic acid molecules that remain hybridized with a polynucleotide encoding a polypeptide according to the present invention, such as SEQ ID NO:1, SEQ ID NO:2, SEQ ID NO:3, SEQ ID NO:4, SEQ ID NO:5, SEQ ID NO:6 or SEQ ID NO:7, or a complement of such a polynucleotide, following washing under stringent washing conditions, in which the wash stringency is equivalent to 0.1× to 0.2×SSC with 0.1% SDS at 55° C. to 65° C.

Percent sequence identity is determined by conventional methods. See, for example, Altschul et al., Bull. Math. Bio. 48:603 (1986), and Henikoff and Henikoff, Proc. Natl. Acad. Sci. USA 89:10915 (1992). Briefly, two amino acid sequences are aligned to optimize the alignment scores using a gap opening penalty of 10, a gap extension penalty of 1, and the "BLOSUM62" scoring matrix of Henikoff and Henikoff (ibid.). The percent identity is then calculated as: ([Total number of identical matches]/[length of the longer sequence plus the number of gaps introduced into the longer sequence in order to align the two sequences])×(100).

Those skilled in the art appreciate that there are many established algorithms available to align two amino acid sequences. The "FASTA" similarity search algorithm of Pearson and Lipman is a suitable protein alignment method for examining the level of identity shared by an amino acid sequence disclosed herein and the amino acid sequence of a putative or variant. The FASTA algorithm is described by Pearson and Lipman, Proc. Nat'l Acad. Sci. USA 85:2444 (1988), and by Pearson, Meth. Enzymol. 183:63 (1990).

Briefly, FASTA first characterizes sequence similarity by identifying regions shared by the query sequence (e.g., SEQ ID NO:1, SEQ ID NO:2, SEQ ID NO:3, SEQ ID NO:4, SEQ ID NO:5, SEQ ID NO:6 or SEQ ID NO:7) and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, J. Mol. Biol. 48:444 (1970); Sellers, SIAM J. Appl. Math. 26:787 (1974)), which allows for amino acid insertions and deletions. Preferred parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, Meth. Enzymol. 183:63 (1990).

FASTA can also be used to determine the sequence identity of nucleic acid molecules using a ratio as disclosed above. For nucleotide sequence comparisons, the ktup value can range between one to six, preferably from three to six, and most preferably, three. The other parameters can be set as: gap opening penalty=10, and gap extension penalty=1.

Substitution of Amino Acid Residues in Polypeptides According to the Present Invention The present invention is also directed to polypeptides having one or more conservative amino acid substitution(s) and polynucleotides encoding polypeptides having one or more conservative amino acid substitution(s), as compared with the amino acid sequence of SEQ ID NO:1, SEQ ID NO:2, SEQ ID NO:3, SEQ ID NO:4, SEQ ID NO:5, SEQ ID NO:6 or SEQ ID NO:7. That is, variants can be obtained that contain e.g. one or more amino acid substitutions of SEQ ID NO:1, SEQ ID NO:2, SEQ ID NO:3, SEQ ID NO:4, SEQ ID NO:5, SEQ ID NO:6 or SEQ ID NO:7. Variants include sequences wherein an alkyl amino acid is substituted for an alkyl amino acid, wherein an aromatic amino acid is substituted for an aromatic amino acid, wherein a sulfur-containing amino acid is substituted for a sulfur-containing amino acid, wherein a hydroxy-containing amino acid is substituted for a hydroxy-containing amino acid, wherein an acidic amino acid is substituted for an acidic amino acid, wherein a basic amino acid is substituted for a basic amino acid, or wherein a dibasic monocarboxylic amino acid is substituted for a dibasic monocarboxylic amino acid.

Among the common amino acids, for example, a "conservative amino acid substitution" can also be illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine.

The BLOSUM62 table is an amino acid substitution matrix derived from about 2,000 local multiple alignments of protein sequence segments, representing highly conserved regions of more than 500 groups of related proteins (Henikoff and Henikoff, Proc. Nat'l Acad. Sci. USA 89:10915 (1992)). Accordingly, the BLOSUM62 substitution frequencies can be used to define conservative amino acid substitutions that may be introduced into the amino acid sequences of the present invention. Although it is possible to design amino acid substitutions based solely upon chemical properties (as discussed above), the language "conservative amino acid substitution" preferably refers to a substitution represented by a BLOSUM62 value of greater than −1. For example, an amino acid substitution is conservative if the substitution is characterized by a BLOSUM62 value of 0, 1, 2, or 3. According to this system, preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3).

Particular variants of polypeptides are characterized by having at least 70%, at least 80%, at least 85%, at least 90%, at least 95% or greater than 95% sequence identity to a corresponding amino acid sequence disclosed herein (i.e., SEQ ID NO:1, SEQ ID NO:2, SEQ ID NO:3, SEQ ID NO:4, SEQ ID NO:5, SEQ ID NO:6 or SEQ ID NO:7), e.g. when the variation in amino acid sequence is due to one or more conservative amino acid substitutions.

Variants of amino acid sequences, such as "conservative amino acid" variants, can be obtained, for example, by oligonucleotide-directed mutagenesis, linker-scanning mutagenesis, mutagenesis using the polymerase chain reaction, and the like (see Ausubel (1995) at pages 8 10 to 8 22; and McPherson (ed.), Directed Mutagenesis: A Practical Approach (IRL Press 1991)).

The polypeptides according to the present invention can also comprise non-naturally occurring amino acid residues. Non-naturally occurring amino acids include e.g., without limitation, trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, thiazolidine carboxylic acid, dehydroproline, 3- and 4-methylproline, 3,3-dimethylproline, tert-leucine, norvaline, 2-azaphenylalanine, 3-azaphenylalanine, 4-azaphenylalanine, and 4-fluorophenylalanine.

Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is typically carried out in a cell-free system comprising an *E. coli* S30 extract and commercially available enzymes and other reagents. Proteins are purified by chromatography. See, for example, Robertson et al., J. Am. Chem. Soc. 113:2722 (1991), Ellman et al., Methods Enzymol. 202: 301 (1991), Chung et al., Science 259:806 (1993), and Chung et al., Proc. Nat'l Acad. Sci. USA 90:10145 (1993).

Multiple amino acid substitutions can be made and tested using known methods of mutagenesis and screening, such as those disclosed by Reidhaar-Olson and Sauer (Science 241: 53 (1988)) or Bowie and Sauer (Proc. Nat'l Acad. Sci. USA 86:2152 (1989)). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., Biochem. 30:10832 (1991), Ladner et al., U.S. Pat. No. 5,223,409, Huse, international publication No. WO 92/06204, and region-directed mutagenesis (Derbyshire et al., Gene 46:145 (1986), and Ner et al., DNA 7:127, (1988)).

Variants of the disclosed nucleotide and polypeptide sequences according to the present invention can also be generated through DNA shuffling as disclosed by Stemmer, Nature 370:389 (1994), Stemmer, Proc. Nat'l Acad. Sci. USA 91:10747 (1994), and international publication No. WO 97/20078. Briefly, variant DNA molecules are generated by in vitro homologous recombination by random fragmentation of a parent DNA followed by reassembly using PCR, resulting in randomly introduced point mutations. This technique can be modified by using a family of parent DNA molecules, such as allelic variants or DNA molecules from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

Mutagenesis methods as disclosed herein can be combined with high-throughput, automated screening methods to detect activity of cloned, mutagenized polypeptides in host cells. Mutagenized DNA molecules that encode biologically active polypeptides, or polypeptides that bind specific antibodies, can be recovered from the host cells and rapidly sequenced using modern equipment. These methods allow the rapid determination of the importance of individual amino acid residues in a polypeptide of interest, and can be applied to polypeptides of unknown structure.

Fragments of Polypeptides According to the Present Invention

The present invention also includes "functional fragments" of polypeptides and nucleic acid molecules according to the present invention encoding such functional fragments. Routine deletion analyses of nucleic acid molecules can be performed to obtain functional fragments of a nucleic acid molecule that encodes a polypeptide according to the present invention. As an illustration, DNA molecules encoding SEQ ID NO:1, SEQ ID NO:2, SEQ ID NO:3, SEQ ID NO:4, SEQ ID NO:5, SEQ ID NO:6 or SEQ ID NO:7 can be digested with Bal31 nuclease to obtain a series of nested deletions. The fragments are then inserted into expression vectors in proper reading frame, and the expressed polypeptides are isolated and tested for the ability to bind specifically to anti-antibodies. One alternative to exonuclease digestion is to use oligonucleotide-directed mutagenesis to introduce deletions or stop codons to specify production of a desired fragment. Alternatively, particular fragments of a gene according to the present invention can be synthesized using the polymerase chain reaction.

Methods for identifying functional domains are well-known to those of skill in the art. For example, studies on the truncation at either or both termini of interferons have been summarized by Horisberger and Di Marco, Pharmac. Ther. 66:507 (1995). Moreover, standard techniques for functional analysis of proteins are described by, for example, Treuter et al., Molec. Gen. Genet. 240:113 (1993), Content et al., "Expression and preliminary deletion analysis of the 42 kDa 2 5A synthetase induced by human interferon," in Biological Interferon Systems, Proceedings of ISIR-TNO Meeting on Interferon Systems, Cantell (ed.), pages 65 72 (Nijhoff 1987), Herschman, "The EGF Receptor," in Control of Animal Cell Proliferation, Vol. 1, Boynton et al., (eds.) pages 169 199 (Academic Press 1985), Coumailleau et al., J. Biol. Chem. 270:29270 (1995); Fukunaga et al., J. Biol. Chem. 270:25291 (1995); Yamaguchi et al., Biochem. Pharmacol. 50:1295 (1995), and Meisel et al., Plant Molec. Biol. 30:1 (1996).

The present invention also contemplates functional fragments of a polypeptide according to the present invention that has one or more amino acid substitutions, compared with the amino acid sequence of e.g. SEQ ID NO:1, SEQ ID NO:2, SEQ ID NO:3, SEQ ID NO:4, SEQ ID NO:5, SEQ ID NO:6 or SEQ ID NO:7. A variant polypeptide can be identified on the basis of structure by determining the level of identity with a particular amino acid sequence disclosed herein. An alternative approach to identifying a variant polypeptide on the basis of structure is to determine whether a nucleic acid molecule encoding a potential variant polypeptide can hybridize to a nucleic acid molecule encoding e.g. SEQ ID NO:1, SEQ ID NO:2, SEQ ID NO:3, SEQ ID NO:4, SEQ ID NO:5, SEQ ID NO:6 or SEQ ID NO:7, as discussed above.

The present invention also provides polypeptide fragments or peptides comprising an epitope-bearing portion of a polypeptide according to the present invention as described herein. Such fragments or peptides may comprise an "immunogenic epitope," which is a part of a protein that elicits an antibody response when the entire protein is used as an immunogen. Immunogenic epitope-bearing peptides can be identified using standard methods (see, for example, Geysen et al., Proc. Nat'l Acad. Sci. USA 81:3998 (1983)).

In contrast, polypeptide fragments or peptides may comprise an "antigenic epitope," which is a region of a protein molecule to which an antibody can specifically bind. Certain epitopes consist of a linear or contiguous stretch of amino acids, and the antigenicity of such an epitope is not disrupted by denaturing agents. It is known in the art that relatively short synthetic peptides that can mimic epitopes of a protein can be used to stimulate the production of antibodies against the protein (see, for example, Sutcliffe et al., Science 219:660 (1983)). Accordingly, antigenic epitope-bearing peptides and polypeptides of the present invention are useful to raise antibodies that bind with the polypeptides described herein.

Antigenic epitope-bearing peptides and polypeptides can contain at least 4 to 10 amino acids, for example at least 5 to 10 amino acids, such as at least 6 to 10 amino acids, for example at least 7 to 10 amino acids, such as at least 10 to 15 amino acids, for example about 15 to about 30 amino acids of e.g. SEQ ID NO:1, SEQ ID NO:2, SEQ ID NO:3, SEQ ID NO:4, SEQ ID NO:5, SEQ ID NO:6 or SEQ ID NO:7.

Such epitope-bearing peptides and polypeptides can be produced by fragmenting a polypeptide according to the present invention, or by chemical peptide synthesis, as described herein. Moreover, epitopes can be selected by phage display of random peptide libraries (see, for example, Lane and Stephen, Curr. Opin. Immunol. 5:268 (1993), and Cortese et al., Curr. Opin. Biotechnol. 7:616 (1996)). Standard methods for identifying epitopes and producing antibodies from small peptides that comprise an epitope are described, for example, by Mole, "Epitope Mapping," in Methods in Molecular Biology, Vol. 10, Manson (ed.), pages 105 116 (The Humana Press, Inc. 1992), Price, "Production and Characterization of Synthetic Peptide-Derived Antibodies," in Monoclonal Antibodies: Production, Engineering, and Clinical Application, Ritter and Ladyman (eds.), pages 60 84 (Cambridge University Press 1995), and Coligan et al. (eds.), Current Protocols in Immunology, pages 9.3.1 9.3.5 and pages 9.4.1 9.4.11 (John Wiley & Sons 1997).

Regardless of the particular nucleotide sequence of a variant gene according to the present invention, the gene encodes a polypeptide that may be characterized by its ability to bind specifically to an antibody capable of specifically binding e.g. to SEQ ID NO:1, SEQ ID NO:2, SEQ ID NO:3, SEQ ID NO:4, SEQ ID NO:5, SEQ ID NO:6 or SEQ ID NO:7.

Fusion Polypeptides

Fusion proteins comprising polypeptides according to the present invention can be used to express a polypeptide according to the present invention in a recombinant host, and to isolate expressed polypeptides. One type of fusion protein comprises a peptide that guides a polypeptide according to the present invention from a recombinant host cell. To direct a polypeptide according to the present invention into the secretory pathway of a eukaryotic host cell, a secretory signal sequence (also known as a signal peptide, a leader sequence, prepro-sequence or pre sequence) is provided in a suitable expression vector. While the secretory signal sequence may be derived from a polypeptide according to the present invention, a suitable signal sequence may also be derived from another secreted protein or synthesized de novo. The secretory signal sequence is operably linked to a gene encoding sequence according to the present invention such that the two sequences are joined in the correct reading frame and positioned to direct the newly synthesized polypeptide into the secretory pathway of the host cell. Secretory signal sequences are commonly positioned 5' to the nucleotide sequence encoding the polypeptide of interest, although certain secretory signal sequences may be positioned elsewhere in the nucleotide sequence of interest (see, e.g., Welch et al., U.S. Pat. No. 5,037,743; Holland et al., U.S. Pat. No. 5,143,830).

Although the secretory signal sequence of a gene according to the present invention, or another protein produced by mammalian cells (e.g., tissue-type plasminogen activator signal sequence, as described, for example, in U.S. Pat. No. 5,641,655) is useful for expression of a gene according to the present invention in recombinant mammalian hosts, a yeast signal sequence is preferred for expression in yeast cells. Examples of suitable yeast signal sequences are those derived from yeast mating pheromone alpha-factor (encoded by the MF-alpha1 gene), invertase (encoded by the SUC2 gene), or acid phosphatase (encoded by the PHO5 gene). See, for example, Romanos et al., "Expression of Cloned Genes in Yeast," in DNA Cloning 2: A Practical Approach, 2.sup.nd Edition, Glover and Hames (eds.), pages 123 167 (Oxford University Press 1995).

In bacterial cells, it is often desirable to express a heterologous protein as a fusion protein to decrease toxicity, increase stability, and to enhance recovery of the expressed protein. For example, a gene according to the present invention can be expressed as a fusion protein comprising a glutathione S-transferase polypeptide. Glutathione S-transferease fusion proteins are typically soluble, and easily purifiable from E. coli lysates on immobilized glutathione columns. In similar approaches, a fusion protein according to the present invention comprising a maltose binding protein polypeptide can be isolated with an amylose resin column, while a fusion protein comprising the C-terminal end of a truncated Protein A gene can be purified using IgG-Sepharose. Established techniques for expressing a heterologous polypeptide as a fusion protein in a bacterial cell are described, for example, by Williams et al., "Expression of Foreign Proteins in E. coli Using Plasmid Vectors and Purification of Specific Polyclonal Antibodies," in DNA Cloning 2: A Practical Approach, 2.sup.nd Edition, Glover and Hames (Eds.), pages 15 58 (Oxford University Press 1995). In addition, commercially available expression systems are available. For example, the PINPOINT Xa protein purification system (Promega Corporation; Madison, Wis.) provides a method for isolating a fusion protein comprising a polypeptide that becomes biotinylated during expression with a resin that comprises avidin.

Peptide tags that are useful for isolating heterologous polypeptides expressed by either prokaryotic or eukaryotic cells include polyHistidine tags (which have an affinity for nickel-chelating resin), c-myc tags, calmodulin binding protein (isolated with calmodulin affinity chromatography), substance P, the RYIRS tag (which binds with anti-RYIRS antibodies), the Glu-Glu tag, and the FLAG tag (which binds with anti-FLAG antibodies). See, for example, Luo et al., Arch. Biochem. Biophys. 329:215 (1996), Morganti et al., Biotechnol. Appl. Biochem. 23:67 (1996), and Zheng et al., Gene 186:55 (1997). Nucleic acid molecules encoding such peptide tags are available, for example, from Sigma-Aldrich Corporation (St. Louis, Mo.).

Another form of fusion protein comprises a polypeptide according to the present invention and an immunoglobulin heavy chain constant region, typically an $F_c$ fragment, which contains two constant region domains and a hinge region but lacks the variable region. As an illustration, Chang et al., U.S. Pat. No. 5,723,125, describe a fusion protein comprising a human interferon and a human immunoglobulin Fc fragment. The C-terminal of the interferon is linked to the N-terminal of the Fc fragment by a peptide linker moiety. An example of a peptide linker is a peptide comprising primarily a T cell inert sequence, which is immunologically inert. An exemplary peptide linker has the amino acid sequence: GGSGG SGGGG SGGGG S. In this fusion protein, a preferred $F_c$ moiety is a human gamma4 chain, which is stable in solution and has little or no complement activating activity. Accordingly, the present invention contemplates a fusion protein that comprises a polypeptide according to the present invention, or a fragment thereof, and a human $F_c$ fragment, wherein the C-terminus of the polypeptide according to the present invention, or a fragment thereof, is attached to the N-terminus of the $F_c$ fragment via a peptide linker.

In another variation, a fusion protein comprising a polypeptide according to the present invention further comprises an IgG sequence. The polypeptide moiety according to the present invention is covalently joined to the amino terminal end of the IgG sequence, and a signal peptide that is covalently joined to the amino terminal of the polypeptide moiety according to the present invention, wherein the IgG sequence comprises or consists of the following elements in the following order: a hinge region, a $CH_2$ domain, and a $CH_3$ domain. Accordingly, the IgG sequence lacks a $CH_1$ domain. The polypeptide moiety according to the present invention displays a protease inhibiting activity. The above, general approaches for producing fusion proteins that comprise both antibody and non-antibody portions have been described by LaRochelle et al., EP 742830 (WO 95/21258).

Fusion proteins can be prepared by methods known to those skilled in the art by preparing each component of the fusion protein and chemically conjugating them. Alternatively, a polynucleotide encoding both components of the fusion protein in the proper reading frame can be generated using known techniques and expressed by the methods described herein. General methods for enzymatic and chemical cleavage of fusion proteins are described, for example, by Ausubel (1995) at pages 16 19 to 16 25.

Pharmaceutical Composition

In another aspect, the invention relates to a pharmaceutical composition that includes a pharmaceutically acceptable carrier and an exosite interactor such as a PAPP-A exosite(s) interactor, as well as methods for identifying such agents. The pharmaceutical composition is administered to an individual in need there of in a pharmacologically effective amount to obtain a therapeutic effect, an ameliorating effect or prophylactic effect.

Identification of PAPP-A as the IGFBP-4 protease provides methods for affecting growth and differentiation in vivo by using PAPP-A as a therapeutic target. Inhibitors of PAPP-A will decrease the amount of bioavailable IGF-I and IGF-II. For example, inhibition of PAPP-A activity can be useful in disorders such as restenosis, atherosclerosis, and fibrosis. Activators, or agents that increase the activity of PAPP-A, will increase the amount of bioavailable IGF-I and IGF-II.

Agents that alter PAPP-A activity or that alter adherence of PAPP-A to cell surfaces can be incorporated into pharmaceutical compositions. For example, a PAPP-A antibody such as PAC1 and/or PAC2 can be formulated into a pharmaceutical composition by admixture with pharmaceutically acceptable non-toxic excipients or carriers.

Formulations for parenteral administration may contain as common excipients (i.e., pharmaceutically acceptable carriers) sterile water or saline, polyalkylene glycols such as polyethylene glycol, oils of vegetable origin, hydrogenated naphthalenes, and the like. In particular, biocompatible, biodegradable lactide polymer, lactide/glycolide copolymer, or polyoxethylene-polyoxypropylene copolymers are examples of excipients for controlling the release of a compound of the invention in vivo. Other suitable parenteral delivery systems include ethylene-vinyl acetate copolymer particles, osmotic pumps, implantable infusion systems, and liposomes. Formulations for inhalation administration may contain excipients such as lactose, if desired. Inhalation formulations may be aqueous solutions containing, for example, polyoxyethylene-9-lauryl ether, glycocholate and deoxycholate, or they may be oily solutions for administration in the form of nasal drops. If desired, the compounds can be formulated as gels to be applied intranasally. Formulations for parenteral administration may also include glycocholate for buccal administration Treatment of Disease Targeting IGF signalling is thought to be highly relevant in human disease, notably in cancer and cardiovascular disease. Specific inhibition of growth promoting proteolytic activity may be a valuable alternative to the direct inhibition of IGF signalling, in particular because such inhibition of IGF receptor stimulation is unlikely to interfere with e.g. insulin signalling.

In one embodiment the present invention relates to use of one or more protease inhibitors targeting the exosite(s) in PAPP-A such as PAC1 and/or PAC2 or any variant of PAC1 and/or PAC2 described in this documents for treatment of one or more diseases.

The invention also relates to modulation of PAPP-A activity and/or production and/or IGF release and/or IGFBP-4 cleavage by one or more exosite(s) interactors in an individual in need there of. This individual can e.g. be a mammal such as a human being.

The present invention further relates to modulation of one or more growth-promoting state(s) such as restenosis, atherosclerosis, ovulation, follicular development, wound healing, fibrosis, or cancer by use of one or more of the exosite(s) interactors described in the present invention such as PAPP-A exosite(s) interactors like PAC1 or PAC2.

The present invention further relates to modulation of one or more growth-inhibiting state(s) such as for example osteoporosis, bone remodelling or cancer by use of one or more of the exosite(s) interactors described in the present invention such as PAPP-A exosite(s) interactors like PAC1 or PAC2.

For example, enhanced PAPP-A activity can be useful for wound healing, fractures, osteoporosis, or ovulation. Osteoporosis or other conditions of bone loss may benefit from increased bone formation and decreased bone resorption.

A medical device such as for example, bone plates or bone screws that are used to stabilize bones, or a stent, which typically is used within the body to restore or maintain the patency of a body lumen can be coated with one or more PAPP-A exosite(s) interactors.

Treatment of One or More Types of Cancer(s)

In one embodiment the present invention relates to use of one or more protease inhibitors targeting the exosite(s) in PAPP-A such as PAC1 and/or PAC2 or any variant of PAC1 and/or PAC2 described in this document for treatment of one or more types of cancer.

In one embodiment the present invention relates to use of one or more protease inhibitors targeting the exosite(s) in PAPP-A such as PAC1 and/or PAC2 or any variant of PAC1 and/or PAC2 described in this documents for treatment of one or more types of cancer selected from the group consisting of Acute Lymphoblastic Leukaemia, Acute Myeloid Leukaemia, Adrenocortical Carcinoma, AIDS-Related Cancers, AIDS-Related Lymphoma, Anal Cancer, Astrocytoma (e.g. Childhood Cerebellar or Childhood Cerebral), Basal Cell Carcinoma, Extrahepatic Bile Duct Cancer, Bladder Cancer, Bone Cancer, Osteosarcoma/Malignant Fibrous Histiocytoma, Brain Stem Glioma, Brain Tumor, Breast Cancer, Male Breast Cancer, Bronchial Adenomas/Carcinoids, Burkitt's Lymphoma, Carcinoid Tumor, Carcinoma of Unknown Primary, Primary Central Nervous System Lymphoma, Cerebral Astrocytoma/Malignant Glioma, Cervical Cancer, Childhood Cancers, Chronic Lymphocytic Leukemia, Chronic Myelogenous Leukaemia, Chronic Myeloproliferative Disorders, Colon Cancer, Cutaneous T-Cell Lymphoma, Endometrial Cancer, Ependymoma (such as Childhood Ependymoma), Oesophageal Cancer, Ewing's Family of Tumors, Extracranial Germ Cell Tumor (such as Childhood Extracranial Germ Cell Tumor), Extragonadal Germ Cell Tumor, Eye Cancer (Intraocular Melanoma or Retinoblastoma), Gallbladder Cancer, Gastric (Stomach) Cancer, Gastrointestinal Carcinoid Tumor, Gestational Trophoblastic Tumor, Glioma, Hairy Cell Leukaemia, Head and Neck Cancer, Hepatocellular (Liver) Cancer, Hodgkin's Lymphoma, Hypopharyngeal Cancer, Hypothalamic and Visual Pathway Glioma (such as Childhood Hypothalamic and Visual Pathway Glioma), Intraocular Melanoma, Islet Cell Carcinoma (Endocrine Pancreas), Kaposi's Sarcoma, Kidney (Renal Cell) Cancer, Laryngeal Cancer, Lip and Oral Cavity Cancer, Lung Cancer (Non-Small Cell or Small Cell), Lymphoma (such as AIDS-Related Lymphoma, Burkitt's Lymphoma, Cutaneous T-Cell Lymphoma, Non-Hodgkin's Lymphoma), Macroglobulinemia (such as Waldenström's Macroglobulinemia), Malignant Fibrous Histiocytoma of Bone/Osteosarcoma, Medulloblastoma (such as Childhood Medulloblastoma), Melanoma, Merkel Cell Carcinoma, Mesothelioma (such as Adult Malignant Mesothelioma or childhood Mesothelioma), Metastatic Squamous Neck Cancer with Occult Primary, Multiple Endocrine Neoplasia Syndrome (such as occurring in childhood), Multiple Myeloma/Plasma Cell Neoplasm, Mycosis Fungoides, Myelodysplastic Syndromes, Myelodysplastic/Myeloproliferative Diseases, Myeloma (such as Multiple Myeloma), Chronic myeloproliferative disorders, Nasal Cavity and Paranasal Sinus Cancer, Nasopharyngeal Cancer, Nasopharyngeal Cancer (such as Childhood Nasopharyngeal Cancer), Neuroblastoma, Oropharyngeal Cancer, Osteosarcoma/Malignant Fibrous Histiocytoma of Bone, Ovarian Cancer (such as Childhood Ovarian Cancer), Ovarian Epithelial Cancer, Ovarian Germ Cell Tumor, Ovarian Low Malignant Potential Tumor, Pancreatic Cancer, Pancreatic Cancer, Paranasal Sinus and Nasal Cavity Cancer, Parathyroid Cancer, Penile Cancer, Pheochromocytoma, Pineoblastoma and Supratentorial Primitive Neuroectodermal Tumors, Pituitary Tumor, Pleuropulmonary Blastoma, Prostate Cancer, Renal Pelvis and Ureter Transitional Cell Cancer, Retinoblastoma, Rhabdomyosarcoma (such as Childhood Rhabdomyosarcoma), Salivary Gland Cancer, Adult-onset soft tissue Sarcoma, Soft Tissue Sarcoma (such as Childhood Soft Tissue Sarcoma), uterine Sarcoma, Sezary Syndrome, Skin Cancer (such as non-Melanoma skin cancer), Merkel Cell Skin Carcinoma, Small Intestine Cancer, Supratentorial Primitive Neuroectodermal Tumors (such as occurring in Childhood), Cutaneous T-Cell Lymphoma, Testicular Cancer, Thymoma and Thymic Carcinoma, Thyroid Cancer, Transitional Cell Cancer of the Renal Pelvis and Ureter, Trophoblastic Tumor (such as Gestational Trophoblastic Tumor), Urethral Cancer, Endometrial uterine cancer, Uterine Sarcoma, Vaginal Cancer, Visual Pathway and Hypothalamic Glioma (such as Childhood Visual Pathway and Hypothalamic Glioma), Waldenström's Macroglobulinemia or Wilms' Tumour.

Treatment of One or More Cardiovascular Disease(s)

In one embodiment the present invention relates to use of one or more protease inhibitors targeting the exosite(s) in PAPP-A such as PAC1 and/or PAC2 or any variant of PAC1 and/or PAC2 described in this document for treatment of one or more types of cardiovascular disease(s).

For example, coating or impregnating the medical device with a PAPP-A inhibitor can help prevent the development of restenosis following balloon angioplasty, or can prevent a further increase in size of an atherosclerotic plaque. Coronary angioplasty with stent placement is currently the leading therapeutic approach for coronary atherosclerosis. An important goal of angioplasty of coronary artery disease is to prevent both acute and chronic complications. Modern procedures are quite successful in eliminating immediate problems. Unfortunately, restenosis still occurs in 20-30% of stented patients. No known pharmacological intervention is available to prevent the restenosis. Without being bound by a particular mechanism, it is thought that an increase in IGFBP-4 protease expression by coronary smooth muscle cells precedes neointimal formation in response to angioplasty in humans.

In one embodiment the present invention relates to use of one or more protease inhibitors targeting the exosite(s) in PAPP-A such as PAC1 and/or PAC2 or any variant of PAC1 and/or PAC2 described in this documents for treatment of one or more types of cardiovascular disease(s) selected from the group consisting of Aneurysms, Angina, Arrhythmia, Atherosclerosis, Cardiomyopathy, Cerebrovascular Accident (Stroke), Cerebrovascular Disease, Congenital Heart Disease, Congestive Heart Failure, Cardiac failure, Myocarditis, Valve Disease, Coronary Artery Disease, Dilated cardiomyopathy, Diastolic Dysfunction, Endocarditis, High Blood Pressure (Hypertension), Hypertrophic Cardiomyopathy, Mitral valve prolapse, Myocardial Infarction (Heart Attack), and Venous Thromboembolism.

In one embodiment the present invention relates to use of one or more protease inhibitors targeting the exosite(s) in PAPP-A such as PAC1 and/or PAC2 or any variant of PAC1 and/or PAC2 described in this documents for treatment of one or more types of cardiovascular disease(s)/conditions selected from the group consisting of Acute coronary syndrome, e.g., myocardial ischemia and myocardial infarction, Cerebrovascular accident/stroke, Atrial fibrillation, cardiac arrhythmia, Angina pectoris, Stable angina, Deep-vein thrombosis and pulmonary embolism, thrombus (blood clot), Peripheral arterial occlusion, Primary or recurrent arterial thrombosis or embolism, Thrombophilia (tendency to develop thrombosis), Cardiopulmonary bypass for heart surgery and haemodialysis in kidney failure, conventional antithrombotic therapy, coagulation factor disorder, hemophilias, hemophilia A (factor VIII deficiency), hemophilia B (factor IX deficiency or "Christmas disease") and hemophilia C (factor XI deficiency, mild bleeding tendency), von Willebrand disease, bleeding, hemophilia, platelet disorder (inborn or acquired), Glanzmann's thrombasthenia, Bernard-Soulier syndrome (abnormal glycoprotein Ib-IX-V complex), gray platelet syndrome (deficient alpha granules), delta storage pool deficiency (deficient dense granules), hemorrhage, Decreased platelet numbers, myelodysplastic syndrome, bone marrow disorders, destruction by the immune system, immune thrombocytopenic purpura/ITP, thrombotic thrombocytopenic purpura/TTP, hemolytic-uremic syndrome/HUS, paroxysmal nocturnal hemoglobinuria/PNH, disseminated intravascular coagulation/DIC, heparin-induced thrombocytopenia/HIT), thrombosis, Artificial/prosthetic heart valves, Heart valve disease, bacterial endocarditis, rheumatic mitral valve disease, mitral stenosis, mitral valve prolapse, mitral annular calcification, isolated aortic valve disease, Thrombophilia (the propensity to develop thrombosis), thrombophilia, Factor V Leiden, hypercoagulability disorder, Mutation of the gene encoding factor V, deep vein thrombosis (DVT), pulmonary embolism, stroke, heart attack, transient ischemic attack, Prothrombin mutation, Factor II mutation, High homocysteine levels due to MTHFR mutation or vitamin deficiency (vitamins B6, B12 and folic acid), Antiphospholipid syndrome (or antiphospholipid antibody syndrome) (APS), thrombosis in both arteries and veins, plasminogen and fibrinolysis disorders, paroxysmal nocturnal hemoglobinuria, protein C deficiency, protein S deficiency, and anti-thrombin III deficiency.

Treatment of One or More Types of Osteoporosis

Osteoporosis is a disease of bone leading to an increased risk of fracture. In osteoporosis the bone mineral density (BMD) is reduced, bone microarchitecture is disrupted, and the amount and variety of non-collagenous proteins in bone is altered. The term "established osteoporosis" includes the presence of a fragility fracture. Osteoporosis is most common in women after the menopause, when it is called postmenopausal osteoporosis, but may develop in men and premenopausal women in the presence of particular hormonal disorders and other chronic diseases or as a result of smoking and medications, specifically glucocorticoids, when the disease is called steroid- or glucocorticoid-induced osteoporosis (SIOP or GIOP).

Risk factors for osteoporotic fracture can be split between non-modifiable and (potentially) modifiable. In addition, there are specific diseases and disorders in which osteoporosis is a recognized complication. Medication use is theoretically modifiable, although in many cases the use of medication that increases osteoporosis risk is unavoidable.

Non-modifiable risk-factors: The most important risk factors for osteoporosis are advanced age (in both men and women) and female sex; estrogen deficiency following menopause is correlated with a rapid reduction in BMD, while in men a decrease in testosterone levels has a comparable (but less pronounced) effect. While osteoporosis occurs in people from all ethnic groups, European or Asian ancestry predisposes for osteoporosis. Those with a family history of fracture or osteoporosis are at an increased risk; the heritability of the fracture as well as low bone mineral density are relatively high, ranging from 25 to 80 percent. There are at least 30 genes associated with the development of osteoporosis. Those who have already had a fracture are at least twice as likely to have another fracture compared to someone of the same age and sex.

Potentially modifiable: Tobacco smoking—tobacco smoking inhibits the activity of osteoblasts, and is an independent risk factor for osteoporosis. Low body mass index—being overweight protects against osteoporosis, either by increasing load or through the hormone leptin. Malnutrition. Alcoholism. Insufficient physical activity—bone performs remodeling in response to physical stress. People who remain physically active throughout life have a lower risk of osteoporosis. The kind of physical activity that has most effects on bone is weight bearing exercises. The bony prominences and attachments in runners are different in shape and size than those in weightlifters.

Physical activity has its greatest impact during adolescence, affecting peak bone mass most. In adults, physical activity helps maintain bone mass, and can increase it by 1 or 2%. Physical fitness in later life is associated more with a decreased risk of falling than with an increased bone mineral density. Conversely, people who are bedridden are at a significantly increased risk. Excess physical activity—excessive exercise can lead to constant damages to the bones which can cause exhaustion of the structures as described above. There are numerous examples of marathon runners who developed severe osteoporosis later in life. In females, heavy exercise leads to amenorrhea (suppression of the menstrual cycle), which is associated with decreased estrogen levels. Heavy metals—a strong association between cadmium, lead and bone disease has been established. Low level exposure to cadmium is associated with an increased loss of bone mineral density readily in both genders, leading to pain and increased risk of fractures, especially in elderly and in females. Higher cadmium exposure results in osteomalacia (softening of the bone). Soft drinks—some studies indicate that soft drinks (many of which contain phosphoric acid) may increase risk of osteoporosis; others suggest soft drinks may displace calcium-containing drinks from the diet rather than directly causing osteoporosis.

Medication—for medication potentially causing osteoporosis, the positive effects of them needs to be compared with the degenerative effects on bone. Steroid-induced osteoporosis (SIOP) arises due to use of glucocorticoids—analogous to Cushing's syndrome and involving mainly the axial skeleton. The synthetic glucocorticoid prescription drug prednisolone is a main candidate after prolonged intake. Some professional guidelines recommend prophylaxis in patients who take the equivalent of more than 30 mg hydrocortisone (7.5 mg of prednisolone), especially when this is in excess of three months. Barbiturates and some other enzyme-inducing antiepileptics—these probably accelerate the metabolism of vitamin D. Proton pump inhibitors—these drugs inhibit the production of stomach acid; it is thought that this interferes with calcium absorption. Anticoagulants—long-term use of heparin is associated with a decrease in bone density, and warfarin (and related coumarins) have been linked with an increased risk in osteoporotic fracture in long-term use. Thiazolidinediones (used for diabetes)—rosiglitazone and possibly pioglitazone, inhibitors of PPARγ, have been linked with an increased risk of osteoporosis and fracture.

In one embodiment the present invention relates to use of one or more protease inhibitors targeting the exosite(s) in PAPP-A such as PAC1 and/or PAC2 or any variant of PAC1 and/or PAC2 described in this documents for treatment of osteoporotic disease caused by any risk factor selected form the group consisting of menopause, ageing, hormonal disorders, estrogen deficiency, decreased testosterone, chronic diseases, tobacco smoking, a genetic predisposition, Low body mass index, Malnutrition. Alcoholism, Insufficient physical activity, Heavy metals exposure (e.g. cadmium and lead), excess Soft drink consumption and use of medications such as steroids/glucocorticoids or Barbiturates or other enzyme-inducing antiepileptics or Proton pump inhibitors or Anticoagulants or Thiazolidinediones (used for diabetes).

Administration and Dosage Regime

Any suitable route of administration may be employed for providing a mammal, especially a human, with an effective dose of a compound of the present invention. For example, oral, rectal, vaginal, topical, parenteral, ocular, pulmonary, nasal, and the like may be employed. Other examples of administration include sublingually, intravenously, intramuscularly, intrathecally, subcutaneously, cutaneously and transdermally administration. In one preferred embodiment the administration comprises inhalation, injection or implantation. The administration of the compound according to the present invention can result in a local (topical) effect or a bodywide (systemic) effect.

Dosage forms include tablets, troches, dispersions, suspensions, solutions, capsules, creams, ointments, aerosols, and the like. Preferably compounds of the invention are administered orally or intravenously.

The effective dosage of active ingredient employed may vary depending on the particular compound employed, the mode of administration, the condition being treated and the severity of the condition being treated. Such dosage may be ascertained readily by a person skilled in the art.

In one embodiment the compounds of the present invention is administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams, preferably from about 1 milligram to about 50 milligrams. In the case of a 70 kg adult human, the total daily dose will generally be from about 1 milligram to about 350 milligrams. For a particularly potent compound, the dosage for an adult human may be as low as 0.1 mg. The dosage regimen may be adjusted within this range or even outside of this range to provide the optimal therapeutic response.

Oral administration will usually be carried out using tablets. Examples of doses in tablets are 0.5 mg, 1 mg, 2 mg, 5 mg, 10 mg, 25 mg, 50 mg, 100 mg, and 250 mg. Other oral forms can also have the same dosages (e.g. capsules).

The compound according to the present invention is given in an effective amount to an individual in need there of. The amount of compound according to the present invention in one preferred embodiment is in the range of from about 0.01 milligram per kg body weight per dose to about 20 milligram per kg body weight per dose, such as from about 0.02 milligram per kg body weight per dose to about 18 milligram per kg body weight per dose, for example from about 0.04 milligram per kg body weight per dose to about 16 milligram per kg body weight per dose, such as from about 0.06 milligram per kg body weight per dose to about 14 milligram per kg body weight per dose, for example from about 0.08 milligram per kg body weight per dose to about 12 milligram per kg body weight per dose, such as from about 0.1 milligram per kg body weight per dose to about 10 milligram per kg body weight per dose, such as from about 0.2 milligram per kg body weight per dose to about 10 milligram per kg body weight per dose, for example from about 0.3 milligram per kg body weight per dose to about 10 milligram per kg body weight per dose, such as from about 0.4 milligram per kg body weight per dose to about 10 milligram per kg body weight per dose, for example from about 0.5 milligram per kg body weight per dose to about 10 milligram per kg body weight per dose, such as from about 0.6 milligram per kg body weight per dose to about 10 milligram per kg body weight per dose, for example from about 0.7 milligram per kg body weight per dose to about 10 milligram per kg body weight per dose, such as from about 0.8 milligram per kg body weight per dose to about 10 milligram per kg body weight per dose, for example from about 0.9 milligram per kg body weight per dose to about 10 milligram per kg body weight per dose, such as from about 1.0 milligram per kg body weight per dose to about 10 milligram per kg body weight per dose, for example from about 1.2 milligram per kg body weight per dose to about 10 milligram per kg body weight per dose, such as from about 1.4 milligram per kg body weight per dose to about 10 milligram per kg body weight per dose, for example from about 1.6 milligram per kg body weight per dose to about 10 milligram per kg body weight per dose, such as from about 1.8 milligram per kg body weight per dose to about 10 milligram per kg body weight per dose, for example from about 2.0 milligram per kg body weight per dose to about 10 milligram per kg body weight per dose, such as from about 2.2 milligram per kg body weight per dose to about 10 milligram per kg body weight per dose, for example from about 2.4 milligram per kg body weight per dose to about 10 milligram per kg body weight per dose, such as from about 2.6 milligram per kg body weight per dose to about 10 milligram per kg body weight per dose, for example from about 2.8 milligram per kg body weight per dose to about 10 milligram per kg body weight per dose, such as from about 3.0 milligram per kg body weight per dose to about 10 milligram per kg body weight per dose, for example from about 3.2 milligram per kg body weight per dose to about 10 milligram per kg body weight per dose, such as from about 3.4 milligram per kg body weight per dose to about 10 milligram per kg body weight per dose, for example from about 3.6 milligram per kg body weight per dose to about 10 milligram per kg body weight per dose, such as from about 3.8 milligram per kg body weight per dose to about 10 milligram per kg body weight per dose, for example from about 4.0 milligram per kg body weight per dose to about 10 milligram per kg body weight per dose, such as from about 4.2 milligram per kg body weight per dose to about 10 milligram per kg body weight per dose, for example from about 4.4 milligram per kg body weight per dose to about 10 milligram per kg body weight per dose, such as from about 4.6 milligram per kg body weight per dose to about 10 milligram per kg body weight per dose, for example from about 4.8 milligram per kg body weight per dose to about 10 milligram per kg body weight per dose, such as from about 5.0 milligram per kg body weight per dose to about 10 milligram per kg body weight per dose, for example from about 5.2 milligram per kg body weight per dose to about 10 milligram per kg body weight per dose, such as from about 5.4 milligram per kg body weight per dose to about 10 milligram per kg body weight per dose, for example from about 5.6 milligram per kg body weight per dose to about 10 milligram per kg body weight per dose, such as from about 5.8 milligram per kg body weight per dose to about 10 milligram per kg body weight per dose, for example from about 6.0 milligram per kg body weight per dose to about 10 milligram per kg body weight per dose, such as from about 6.2 milligram per kg body weight per dose to about 10 milligram per kg body weight per dose, for example from about 6.4 milligram per kg body weight per dose to about 10 milligram per kg body weight per dose, such as from about 6.6 milligram per kg body weight per dose to about 10 milligram per kg body weight per dose, for example from about 6.8 milligram per kg body weight per dose to about 10 milligram per kg body weight per dose, such as from about 7.0 milligram per kg body weight per dose to about 10 milligram per kg body weight per dose, for example from about 7.2 milligram per kg body weight per dose to about 10 milligram per kg body weight per dose, such as from about 7.4 milligram per kg body weight per dose to about 10 milligram per kg body weight per dose, for example from about 7.6 milligram per kg body weight per dose to about 10 milligram per kg body weight per dose, such as from about 7.8 milligram per kg body weight per dose to about 10 milligram per kg body weight per dose, for example from about 8.0 milligram per kg body weight per dose to about 10 milligram per kg body weight per dose, such as from about 0.2 milligram per kg body weight per dose to about 8 milligram per kg body weight per dose, for example from about 0.3 milligram per kg body weight per dose to about 8 milligram per kg body weight per dose, such as from about 0.4 milligram per kg body weight per dose to about 8 milligram per kg body weight per dose, for example from about 0.5 milligram per kg body weight per dose to about 8 milligram per kg body weight per dose, such as from about 0.6 milligram per kg body weight per dose to about 8 milligram per kg body weight per dose, for example from about 0.7 milligram per kg body weight per dose to about 8 milligram per kg body weight per dose, such as from about 0.8 milligram per kg body weight per dose to about 8 milligram per kg body weight per dose, for example from about 0.9 milligram per kg body weight per dose to about 8 milligram per kg body weight per dose, such as from about 1.0 milligram per kg body weight per dose to about 8 milligram per kg body weight per dose, for example from about 1.2 milligram per kg body weight per dose to about 8 milligram per kg body weight per dose, such as from about 1.4 milligram per kg body weight per dose to about 8 milligram per kg body weight per dose, for example from about 1.6 milligram per kg body weight per dose to about 8 milligram per kg body weight per dose, such as from about 1.8 milligram per kg body weight per dose to about 8 milligram per kg body weight per dose, for example from about 2.0 milligram per kg body weight per dose to about 8 milligram per kg body weight per dose, such as from about 2.2 milligram per kg body weight per dose to about 8 milligram per kg body weight per dose, for example from about 2.4 milligram per kg body weight per dose to about 8 milligram per kg body weight per dose, such as from about 2.6 milligram per kg body weight per dose to about 8 milligram per kg body weight per dose, for example from about 2.8 milligram per kg body weight per dose to about 8 milligram per kg body weight per dose, such as from about 3.0 milligram per kg body weight per dose to about 8 milligram per kg body weight per dose, for example from about 3.2 milligram per kg body weight per dose to about 8 milligram per kg body weight per dose, such as from about 3.4 milligram per kg body weight per dose to about 8 milligram per kg body weight per dose, for example from about 3.6 milligram per kg body weight per dose to about 8 milligram per kg body weight per dose, such as from about 3.8 milligram per kg body weight per dose to about 8 milligram per kg body weight per dose, for example from about 4.0 milligram per kg body weight per dose to about 8 milligram per kg body weight per dose, such as from about 4.2 milligram per kg body weight per dose to about 8 milligram per kg body weight per dose, for example from about 4.4 milligram per kg body weight per dose to about 8 milligram per kg body weight per dose, such as from about 4.6 milligram per kg body weight per dose to about 8 milligram per kg body weight per dose, for example from about 4.8 milligram per kg body weight per dose to about 8 milligram per kg body weight per dose, such as from about 5.0 milligram per kg body weight per dose to about 8 milligram per kg body weight per dose, for example from about 5.2 milligram per kg body weight per dose to about 8 milligram per kg body weight per dose, such as from about 5.4 milligram per kg body weight per dose to about 8 milligram per kg body weight per dose, for example from about 5.6 milligram per kg body weight per dose to about 8 milligram per kg body weight per dose, such as from about 5.8 milligram per kg body weight per dose to about 8 milligram per kg body weight per dose, for example from about 6.0 milligram per kg body weight per dose to about 8 milligram per kg body weight per dose, such as from about 0.2 milligram per kg body weight per dose to about 6 milligram per kg body weight per dose, for example from about 0.3 milligram per kg body weight per dose to about 6 milligram per kg body weight per dose, such as from about 0.4 milligram per kg body weight per dose to about 6 milligram per kg body weight per dose, for example from about 0.5 milligram per kg body weight per dose to about 6 milligram per kg body weight per dose, such as from about 0.6 milligram per kg body weight per dose to about 6 milligram per kg body weight per dose, for example from about 0.7 milligram per kg body weight per dose to about 6 milligram per kg body weight per dose, such as from about 0.8 milligram per kg body weight per dose to about 6 milligram per kg body weight per dose, for example from about 0.9 milligram per kg body weight per dose to about 6 milligram per kg body weight per dose, such as from about 1.0 milligram per kg body weight per dose to about 6 milligram per kg body weight per dose, for example from about 1.2 milligram per kg body weight per dose to about 6 milligram per kg body weight per dose, such as from about 1.4 milligram per kg body weight per dose to about 6 milligram per kg body weight per dose, for example from about 1.6 milligram per kg body weight per dose to about 6 milligram per kg body weight per dose, such as from about 1.8 milligram per kg body weight per dose to about 6 milligram per kg body weight per dose, for example from about 2.0 milligram per kg body weight per dose to about 6 milligram per kg body weight per dose, such as from about 2.2 milligram per kg body weight per dose to about 6 milligram per kg body weight per dose, for example from about 2.4 milligram per kg body weight per dose to about 6 milligram per kg body weight per dose, such as from about 2.6 milligram per kg body weight per dose to about 6 milligram per kg body weight per dose, for example from about 2.8 milligram per kg body weight per dose to about 6 milligram per kg body weight per dose, such as from about 3.0 milligram per kg body weight per dose to about 6 milligram per kg body weight per dose, for example from about 3.2 milligram per kg body weight per dose to about 6 milligram per kg body weight per dose, such as from about 3.4 milligram per kg body weight per dose to about 6 milligram per kg body weight per dose, for example from about 3.6 milligram per kg body weight per dose to about 6 milligram per kg body weight per dose, such as from about 3.8 milligram per kg body weight per dose to about 6 milligram per kg body weight per dose, for example from about 4.0 milligram per kg body weight per dose to about 6 milligram per kg body weight per dose, such as from about 4.2 milligram per kg body weight per dose to about 6 milligram per kg body weight per dose, for example from about 4.4 milligram per kg body weight per dose to about 6 milligram per kg body weight per dose, such as from about 4.6 milligram per kg body weight per dose to about 6 milligram per kg body weight per dose, for example from about 4.8 milligram per kg body weight per dose to about 6 milligram per kg body weight per dose, such as from about 5.0 milligram per kg body weight per dose to about 6 milligram per kg body weight per dose.

The invention also features a medical device for placement in a patient (e.g., an implant) that includes an exosite(s) interactor such as a PAPP-A exosite(s) interactor like for example PAC1 and/or PAC2.

Co-Administration

Co-Administration with One or More Anti-Cancer Drugs

In one embodiment the present invention relates to co-administration of one or more protease inhibitors targeting the exosite(s) in PAPP-A such as PAC1 and/or PAC2 or any variant of PAC1 and/or PAC2 described in this document and one or more anti-cancer drug(s).

In one embodiment the present invention relates to co-administration of one or more protease inhibitors targeting the exosite(s) in PAPP-A such as PAC1 and/or PAC2 or any variant of PAC1 and/or PAC2 described in this document and one or more anti-cancer drug(s) selected from the group consisting of:

Aldesleukin/Proleukin (Chiron Corp)
Alemtuzumab/Campath (Millennium and ILEX Partners, LP)
alitretinoin/Panretin (Ligand Pharmaceuticals)
allopurinol/Zyloprim (GlaxoSmithKline)
altretamine/Hexylen (US Bioscience)
amifostine/Ethyol (US Bioscience)
anastrozole/Arimidex (AstraZeneca)
arsenic trioxide/Trisenox (Cell Therapeutic)
Asparaginase/Elspar (Merck & Co, Inc)
BCG Live/TICE BCG (Organon Teknika Corp)
bexarotene capsules/Targretin (Ligand Pharmaceuticals)
bleomycin/Blenoxane (Bristol-Myers Squibb)
busulfan/Busulfex (GlaxoSmithKline)
calusterone/Methosarb (Pharmacia & Upjohn Company)
capecitabine/Xeloda (Roche)
carboplatin/Paraplatin (Bristol-Myers Squibb)
carmustine/BCNU, BiCNU (Bristol-Myers Squibb)
carmustine with Polifeprosan 20 Implant/Gliadel Wafer (Guilford Pharmaceuticals Inc.)
celecoxib/Celebrex (Searle)
chlorambucil/Leukeran (GlaxoSmithKline)
cisplatin/Platinol (Bristol-Myers Squibb)
cladribine/Leustatin, 2-CdA (R.W. Johnson Pharmaceutical Research Institute)
cyclophosphamide Cytoxan/Neosar (Bristol-Myers Squibb)
cytarabine/Cytosar-U (Pharmacia & Upjohn Company)
dacarbazine/DTIC-Dome (Bayer)
dactinomycin/actinomycin D Cosmegen (Merck)
Darbepoetin alfa/Aranesp (Amgen, Inc)
daunorubicin/daunomycin/Daunorubicin (Bedford Labs)
daunorubicin/daunomycin/Cerubidine (Wyeth Ayerst)
Denileukin/diftitox/Ontak (Seragen, Inc)
dexrazoxane/Zinecard (Pharmacia & Upjohn Company)
docetaxel/Taxotere (Aventis Pharmaceutical)
doxorubicin Adriamycin/Rubex (Pharmacia & Upjohn Company)
DROMOSTANOLONE PROPIONATE/MASTERONE INJECTION (SYNTEX)
Elliott's B Solution (Orphan Medical, Inc)
epirubicin/Ellence (Pharmacia & Upjohn Company)
etoposide phosphate (Bristol-Myers Squibb)
etoposide/VP-16/Vepesid (Bristol-Myers Squibb)
exemestane/Aromasin (Pharmacia & Upjohn Company)
Filgrastim/Neupogen (Amgen, Inc)
floxuridine/FUDR (Roche)
fludarabine/Fludara (Berlex Laboratories Inc.)
fluorouracil/5-FU/Adrucil (ICN Puerto Rico)
fulvestrant/Faslodex (IPR)
gemcitabine/Gemzar (Eli Lilly)
gemtuzumab/ozogamicin/Mylotarg (Wyeth Ayerst)
goserelin acetate/Zoladex Implant (AstraZeneca Pharmaceuticals)
hydroxyurea/Hydrea (Bristol-Myers Squibb)
Ibritumomab Tiuxetan/Zevalin (IDEC Pharmaceuticals Corp)
idarubicin/Idamycin (Adria Laboratories)
ifosfamide/IFEX (Bristol-Myers Squibb)
imatinib mesylate/Gleevec (Novartis)
Interferon alfa-2a/Roferon-A (Hoffmann-La Roche Inc)
Interferon alfa-2b/Intron A (Schering Corp)
irinotecan/Camptosar (Pharmacia & Upjohn Company)
letrozole/Femara (Novartis)
leucovorin Wellcovorin/Leucovorin (Immunex Corporation)
levamisole/Ergamisol (Janssen Research Foundation)
lomustine/CCNU/CeeBU (Bristol-Myers Squibb)
mechlorethamine/nitrogen mustard/Mustargen (Merck)
megestrol acetate/Megace (Bristol-Myers Squibb)
melphalan/L-PAM/Alkeran (GlaxoSmithKline)
mercaptopurine/6-MP Purinethol (GlaxoSmithKline)
mesna/Mesnex (Asta Medica)
methotrexate (Lederle Laboratories)
methoxsalen/Uvadex (Therakos)
mitomycin C/Mutamycin (Bristol-Myers Squibb)
mitomycin C/Mitozytrex (Supergen)
mitotane/Lysodren (Bristol-Myers Squibb)
mitoxantrone/Novantrone (Lederle Laboratories)
nandrolone phenpropionate/Durabolin-50 (Organon)
Nofetumomab/Verluma (Boehringer Ingelheim Pharma KG (formerly Dr. Karl Thomae GmbH))
Oprelvekin/Neumega (Genetics Institute)
oxaliplatin/Eloxatin (Sanofi Synthelabo)
paclitaxel/Taxol (Bristol-Myers Squibb)
pamidronate/Aredia (Novartis)
pegademase/Adagen (Pegademase Bovine) (Enzon)
Pegaspargase/Oncaspar (Enzon, Inc)
Pegfilgrastim/Neulasta (Amgen, Inc)
pentostatin/Nipent (Parke-Davis Pharmaceutical Co.)
pipobroman/Vercyte (Abbott Labs)
plicamycin/mithramycin/Mithracin (Pfizer Labs)
porfimer sodium/Photofrin (QLT Phototherapeutics Inc.)
procarbazine/Matulane (Sigma Tau Pharms)
quinacrine/Atabrine (Abbott Labs)
Rasburicase/Elitek (Sanofi-Synthelabo, Inc)
Rituximab/Rituxan (Genentech, Inc)
Sargramostim/Prokine (Immunex Corp)
streptozocin/Zanosar (Pharmacia & Upjohn Company)
talc/Sclerosol (Bryan)
tamoxifen/Nolvadex (AstraZeneca Pharmaceuticals)
temozolomide/Temodar (Schering)
teniposide/VM-26/Vumon (Bristol-Myers Squibb)
testolactone/Teslac (Bristol-Myers Squibb)
thioguanine/6-TG/Thioguanine (GlaxoSmithKline)
thiotepa/Thioplex (Lederle Laboratories)
topotecan/Hycamtin (GlaxoSmithKline)
topotecan/Hycamtin (GlaxoSmithKline)
toremifene/Fareston (Orion Corp)
Tositumomab/Bexxar (Corixa Corporation)
Trastuzumab/Herceptin (Genentech, Inc)
tretinoin/ATRA/Vesanoid (Roche)
Uracil Mustard (Roberts Labs)
valrubicin/Valstar (Medeva)
vinblastine/Velban (Eli Lilly)
vincristine/Oncovin (Eli Lilly)
vinorelbine/Navelbine (GlaxoSmithKline), and
zoledronate/Zometa (Novartis)

Co-Administration with One or More Drug(s) for Treatment of One or More Cardiovascular Disease(s)

In one embodiment the present invention relates to co-administration of one or more protease inhibitors targeting the exosite(s) in PAPP-A such as PAC1 and/or PAC2 or any variant of PAC1 and/or PAC2 described in this document and one or more drugs with anti-platelet activity.

In one embodiment the present invention relates to co-administration of one or more protease inhibitors targeting the exosite(s) in PAPP-A such as PAC1 and/or PAC2 or any variant of PAC1 and/or PAC2 described in this documents and one or more drugs with anti-platelet activity selected from the group consisting of Aspirin, aloxiprin, Ditazole, Carbasalate calcium, cloricromen, indobufen, picotamide, triflusal, clopidogrel, dipyridamole, prasugrel, ticlopidine, beraprost, prostacyclin, iloprost, treprostini, abciximab, eptifibatide and tirofiban.

In one embodiment the present invention relates to co-administration of one or more protease inhibitors targeting the exosite(s) in PAPP-A such as PAC1 and/or PAC2 or any variant of PAC1 and/or PAC2 described in this document and one or more drugs with anti-coagulant activity.

In one embodiment the present invention relates to co-administration of one or more protease inhibitors targeting the exosite(s) in PAPP-A such as PAC1 and/or PAC2 or any variant of PAC1 and/or PAC2 described in this documents and one or more drugs with anti-coagulant activity selected from the group consisting of Heparin, bemiparin, dalteparin, enoxaparin, nadroparin, parnaparin, reviparin, tinzaparin, sulodexide, danaparoid, Warfarin/coumarins, Acenocoumarol, Clorindione, Coumatetralyl, Dicumarol, Diphenadione, Ethyl biscoumacetate, Phenprocoumon, Phenindione, Tioclomarol, dabigatran, idraparinux, lepirudin, bivalirudin, Argatroban, desirudin, hirudin, melagatran, ximelagatran, Antithrombin III, rivaroxaban, Fondaparinux, protein C, protein S, TFPI, Defibrotide and Dermatan sulphate.

In one embodiment the present invention relates to co-administration of one or more protease inhibitors targeting the exosite(s) in PAPP-A such as PAC1 and/or PAC2 or any variant of PAC1 and/or PAC2 described in this document and one or more fibrinolytic drug(s).

In one embodiment the present invention relates to co-administration of one or more protease inhibitors targeting the exosite(s) in PAPP-A such as PAC1 and/or PAC2 or any variant of PAC1 and/or PAC2 described in this document and one or more fibrinolytic drug(s) selected from the group consisting of tenecteplase, anistreplase, ancrod, drotrecogin, fibrinolysin, brinase, tPA, uPA, urokinase and streptokinase.

In one embodiment the present invention relates to co-administration of one or more protease inhibitors targeting the exosite(s) in PAPP-A such as PAC1 and/or PAC2 or any variant of PAC1 and/or PAC2 described in this document and one or more drugs used for the treatment of cardiovascular diseases.

In one embodiment the present invention relates to co-administration of one or more protease inhibitors targeting the exosite(s) in PAPP-A such as PAC1 and/or PAC2 or any variant of PAC1 and/or PAC2 described in this document and one or more drugs used for the treatment of cardiovascular diseases, selected from the group consisting of ACE inhibitors (e.g. Captopril, Zofenopil, Enalapril, Ramipril/Altace, Quinapril, Perindopril, Lisinopril/Zestril, Benazepril, Fosinopril/Monopril, Rescinnamine, casokinins and lactokinins); Angiotensin II receptor antagonist (e.g. Candesartan/Atacand, Eprosartan, Irbesartan/Avapro, Losartan/Cozaar, Olmesartan, Telmisartan/Micardis/Pritor and Valsartan/Diovan); Direct renin-inhibitors (e.g. Aliskiren/Tekturna/Rasilez); Diuretics (e.g. Furosemide, Ethacrynic acid, Torasemide, Bumetanide, Hydrochlorothiazide, Chlorthiazide, Bendroflumethiazide, Amiloride, Spironolactone, Eplerenone, Triamterene, Potassium canrenoate, Canrenone, Indapamide, Chlortalidone, Quinethazone, Mersalyl, Metolazone, Theobromine and Cicletanine); Beta blockers (e.g. Bisoprolol, Carvedilol, Metoprolol, Atenolol, Labetalol, Metoprolol/Lopressor/Toprol XL and Propranolol); Positive inotropes (e.g. Digoxin and dobutamine); Calcium channel blockers (e.g. Nifedipine/Adalat/Procardia, Amlodipine/Norvasc, Felodipine/Plendil, Nicardipine/Cardene, Nimodipine/Nimotop, Nisoldipine/Sular, Nitrendipine/Cardiff/Nitrepin, Lacidipine/Motens, Lercanidipine/Zanidip, Diltiazem/Cardizem, Verapamil/Calan/Isoptin and Gallopamil/D600); Alternative vasodilators (e.g. Isosorbide dinitrate, Hydralazine, Diazoxide, Minoxidil, Nitroprusside, Phentolamine and Theobromine); Sympatholytic agents (e.g. Clonidine, Guanfacine, Methyldopa, Moxonidine, Reserpine, Rilmenidine, Mecamylamine, Trimethaphan, Prazosin, Guanethidine, Indoramin, Doxazosin and Terazosin); and other antihypertensives (e.g. Serotonin antagonists such as Ketanserin, endothelin receptor antagonists such as Bosentan, Ambrisentan and Sitaxsentan).

Co-Administration with One or More Adjuvant(s)

In one embodiment the present invention relates to co-administration of one or more protease inhibitors targeting the exosite(s) in PAPP-A such as PAC1 and/or PAC2 or any variant of PAC1 and/or PAC2 described in this document and one or more adjuvant(s).

Adjuvants are often used to optimise the efficacy of an immunogenic composition. Adjuvants generally consist of agents that are included in the formulation used to provide and/or enhance the ability of the immunogenic composition to induce a desired immune response.

Potent, nontoxic adjuvants that will enhance and/or modulate the immunogenicity of immunogenic determinants including antigenic determinants including haptenic determinants represent one group of preferred adjuvants. In addition, such adjuvants preferably also elicit an earlier, more potent, or more prolonged immune response. Such an adjuvant would also be useful in cases where an antigen supply is limited or is costly to produce.

Adjuvants pertaining to the present invention may be grouped according to their origin, be it mineral, bacterial, plant, synthetic, or host product. The first group under this classification is the mineral adjuvants, such as aluminum compounds. Antigens precipitated with aluminum salts or antigens mixed with or adsorbed to performed aluminum compounds have been used extensively to augment immune responses in animals and humans. Aluminum particles have been demonstrated in regional lymph nodes of rabbits seven days following immunization, and it may be that another significant function is to direct antigen to T cell containing areas in the nodes themselves. Adjuvant potency has been shown to correlate with intimation of the draining lymph nodes. While many studies have confirmed that antigens administered with aluminum salts led to increased humoral immunity, cell mediated immunity appears to be only slightly increased, as measured by delayed-type hypersensitivity. Aluminum hydroxide has also been described as activating the complement pathway. This mechanism may play a role in the local inflammatory response as well as immunoglobulin production and B cell memory. Primarily because of their excellent record of safety, aluminum compounds are presently the only adjuvants used in humans.

While aluminum salts have been a sufficient adjuvant for strong immunogens that require only antibody responses to elicit protection, they may not always be effective when used with weak immunogens such as e.g. synthetic peptides of malaria, or for introducing cell-mediated immune responses or IgG isotype of the type required to fight infections.

Another large group of adjuvants are those of bacterial origin. Adjuvants with bacterial origins can be purified and synthesized (e.g. muramyl dipeptides, lipid A) and host mediators have been cloned (Interleukin 1 and 2). The last decade has brought significant progress in the chemical purification of at least three adjuvants of active components of bacterial origin: *Bordetella pertussis*, lipopolysaccharide and Freund's Complete Adjuvant (FCA). Additionally suitable adjuvants in accordance with the present invention are e.g.

Titermax, ISCOMS, Quil A, ALUN, see U.S. Pat. Nos. 5,8767 and 5,554,372, Lipid A derivatives, choleratoxin derivatives, HSP derivatives, LPS derivatives, synthetic peptide matrixes, GMDP, and other as well as combined with immunostimulants (U.S. Pat. No. 5,876,735).

*B. pertussis* is of interest as an adjuvant in the context of the present invention due to its ability to modulate cell-mediated immunity through action on T-lymphocyte populations. For lipopolysaccharide and Freund's Complete Adjuvant, adjuvant active moieties have been identified and synthesized which permit study of structure-function relationships. These are also considered for inclusion in immunogenic compositions according to the present invention.

Lipopolysaccharide and its various derivatives, including lipid A, have been found to be powerful adjuvants in combination with liposomes or other lipid emulsions. It is not yet certain whether derivatives with sufficiently low toxicity for general use in humans can be produced. Freund's Complete Adjuvant is the standard in most experimental studies.

Many other types of materials can be used as adjuvants in immunogenic compositions according to the present invention. They include plant products such as saponin, animal products such as chitin and numerous synthetic chemicals.

Adjuvants according to the present invention can also been categorized by their proposed mechanisms of action. This type of classification is necessarily somewhat arbitrary because most adjuvants appear to function by more than one mechanism. Adjuvants may act through antigen localization and delivery, or by direct effects on cells making up the immune system, such as macrophages and lymphocytes. Another mechanism by which adjuvants according to the invention enhance the immune response is by creation of an antigen depot. This appears to contribute to the adjuvant activity of aluminum compounds, oil emulsions, liposomes, and synthetic polymers. The adjuvant activity of lipopolysaccharides and muramyl dipeptides appears to be mainly mediated through activation of the macrophage, whereas *B. pertussis* affects both macrophages and lymphocytes. Further examples of adjuvants that may be useful when incorporated into immunogenic compositions according to the present invention are described in U.S. Pat. No. 5,554,372.

Co-Administration with One or More Inhibitors of the Blood Coagulation Cascade

In one embodiment the present invention relates to co-administration of one or more protease inhibitors targeting the exosite(s) in PAPP-A such as PAC1 and/or PAC2 or any variant of PAC1 and/or PAC2 described in this document and one or more inhibitors of the blood coagulation cascade.

The blood coagulation system in held in check by a number of natural occurring inhibitors of the system. Tissue factor pathway inhibitor (TFPI) is a 34-kDa protein associated with plasma lipoproteins and with the vascular endothelium.

Antithrombin is a 58 kDa glycoprotein serine protease inhibitor (serpin) that inactivates the serine proteases; thrombin and fXa, as well as fXIIa, and fIXa. It is constantly active, but its adhesion to these factors is increased by the presence of heparan sulfate proteoglycan (a glycosaminoglycan) or the administration of heparins (different heparinoids increase affinity to fXa, thrombin, or both). Antithrombin does not inactivate clot-bound thrombin or fXa.

Protein C is a major physiological anticoagulant. It is a vitamin K-dependent serine protease enzyme that is activated by thrombin into activated protein C (APC). The activated form (with protein S and phospholipid as a cofactor) degrades Factor Va and Factor VIIIa. The protein C pathway's key enzyme, activated protein C, provides physiologic antithrombotic activity and exhibits both anti-inflammatory and anti-apoptotic activities. Its actions are related to development of thrombosis and ischemic stroke.

Protein S is a vitamin K-dependent plasma glycoprotein synthesized in the liver. In the circulation, Protein S exists in two forms: a free form and a complex form bound to complement protein C4b. The best characterized function of Protein S is its role in the anticoagulation pathway, as it functions as a cofactor to Protein C in the inactivation of Factors Va and VIIIa. Only the free form has cofactor activity. Also, Protein S can bind to negatively charged phospholipids via the carboxylated GLA domain. This property allows Protein S to function in the removal of cells which are undergoing apoptosis, which display negatively charged phospholipids on the cell surface. By binding to the negatively charged phospholipids, Protein S functions as a bridging molecule between the apoptotic cell and the phagocyte.

Under normal conditions, the factors that promote the blood coagulation are in balance with those who inhibit it. Venous or arterial thrombosis occurs when the procoagulant stimuli overwhelm the anticoagulant and fibrinolytic system. Virchow's triad is a group of 3 factors known to affect clot formation: rate of flow, the consistency (thickness) of the blood, and qualities of the vessel wall. Currently, medical intervention for treating thrombosis occur by administering anticoagulants that include parenteral administration of e.g. low-molecular weight heparin (LMWH) followed by oral administration of e.g. warfarin. A newer class of drugs, the direct thrombin inhibitors, is under development; some members are already in clinical use (such as lepirudin). Also under development are other small molecular compounds that interfere directly with the enzymatic action of particular coagulation factors (e.g. rivaroxaban). Anti-platelet agents include aspirin, clopidogrel, dipyridamole and ticlopidine; the parenteral glycoprotein IIb/IIIa inhibitors are used during angioplasty.

Heparin is a naturally occurring highly sulphated glycosaminoglycan produced by basophils and mast cells. Heparin acts as an anticoagulant, preventing the formation of clots and extension of existing clots within the blood. While heparin does not break down clots that have already formed (tissue plasminogen activator will), it allows the body's natural clot lysis mechanisms to work normally to break down clots that have already formed. Heparin binds to the enzyme inhibitor antithrombin III (AT-III) causing a conformational change which results in its active site being exposed. The activated AT-III then inactivates thrombin and other proteases involved in blood clotting, most notably factor Xa. The rate of inactivation of these proteases by AT-III increases 1000-fold due to the binding of heparin. AT-III binds to a specific pentasaccharide sulfation sequence contained within the heparin polymer. The conformational change in AT-III on heparin binding mediates its inhibition of factor Xa. For thrombin inhibition however, thrombin must also bind to the heparin polymer at a site proximal to the pentasaccharide. The highly negative charge density of heparin contributes to its very strong electrostatic interaction with thrombin. The formation of a ternary complex between AT-III, thrombin and heparin results in the inactivation of thrombin. For this reason heparin's activity against thrombin is size dependent, the ternary complex requiring at least 18 saccharide units for efficient formation. In contrast anti factor Xa activity only requires the pentasaccharide binding site. This size difference has led to the development of low molecular weight heparins (LMWHs) and more recently to fondaparinux as pharmaceutical anticoagulants that target anti factor Xa activity rather than anti thrombin (IIa) activity. If long-term anticoagulation is required, heparin is often only used to commence anticoagulation therapy until the oral anticoagulant warfarin takes effect.

Factors II, VII, IX, and X are homologous to each other at their N-terminal ends. After removal of the signal peptide, a carboxylase residing in the endoplasmic reticulum or Golgi binds to the propeptide region of each of these proteins and converts ~10-12 glutamate (Glu) residues to g-carboxy-glutamate (Gla) in the adjacent "Gla domain". The propeptide is removed from the carboxylated polypeptide prior to secretion. The Gla residues bind calcium ions and are necessary for the activity of these coagulation factors. Synthesis of Gla requires vitamin K. During g-carboxylation, vitamin K becomes oxidized and must be reduced subsequently in order for the cycle to continue. The anticoagulant drug warfarin (from the group of coumarins) inhibits reduction of vitamin K and thereby prevents synthesis of active factors II, VII, IX, and X.

Anticoagulant therapy, usually with heparin injections short term and/or oral anticoagulants (usually warfarin) long term, is clearly effective in prevention of serious vascular events when given as prophylaxis to high-risk patients, or as treatment of acute arterial or venous thrombosis. Anticoagulant therapy thus prevents the formation as well as the extension of existing clots. However, full-dose anticoagulation is also a common cause of major internal bleeding, including intracranial, gastrointestinal or retroperitoneal haemorrhage, which can be fatal. It is therefore important to select patients most likely to benefit from anticoagulant therapy (i.e. those in whom the risk of major thromboembolic events exceeds the risk of major bleeding); and to minimise both thromboembolic and hemorrhagic morbidity and mortality during anticoagulant therapy.

Co-Administration with Drugs for Treatment of Osteoporosis

In one embodiment the present invention relates to co-administration of one or more protease inhibitors targeting the exosite(s) in PAPP-A such as PAC1 and/or PAC2 or any variant of PAC1 and/or PAC2 described in this document and one or more drugs used for treatment of osteoporosis.

The one or more drugs used for treatment of osteoporosis can in one embodiment be selected from the examples listed below.

Bisphosphanates

Bisphosphanates e.g. Fosamax (Alendronate sodium), Boniva (ibandronate sodium) or Actonel (risedronate sodium) are a type of medication that helps to regulate calcium and prevent bone breakdown. Bone turnover, or replacement of old bone with new bone, is a normal process within our body. In patients with osteoporosis, the replacement with new bone does not maintain pace with the breakdown of old bone. Bisphosphanates slow the rate of bone breakdown to help maintain bone mass by inhibiting the osteoclast, the cell responsible for bone breakdown.

Strontium Ranelate

Strontium ranelate (Protelos) is a drug which stimulates new bone formation, and is used if you do not tolerate bisphosphonates well. Strontium is one of many trace minerals essential for bone health. Strontium supports healthy osteoblast differentiation and helps to keep osteoclast activity in balance. Additionally, strontium supplement supports healthy collagen formation by osteoblasts, enhancing bone tensile strength.

Calcitonin (Miacalcin)

Calcitonin is a naturally occurring hormone produced by the thyroid gland that can be given as an injection or taken as a nasal spray. Sold under the trade name Miacalcin, calcitonin also inhibits the function of the osteoclasts that break down bone. Calcitonin has long been known to be beneficial in patients with osteoporosis, but the injections were difficult to administer, and had unpleasant side-effects. The nasal spray has greatly improved the use of calcitonin, and it is much more commonly used today. Calcitonin has been shown to slow bone loss, and also decrease pain associated with osteoporosis fractures.

Raloxifene

Raloxifene is a newer medication that has been developed to provide some of the same advantages of estrogen (HRT), without the potential side-effects. Raloxifene is a type of medication called a Selective Estrogen Receptor Modulator, or SERM. The effects of Raloxifene have been shown to be similar to estrogen, including an increase in bone mass and lower cholesterol. However, the SERMs do not have the same effects on the uterine lining, and therefore do not need to be combined with progesterone. Furthermore, there is evidence that Raloxifene may decrease the risk of breast cancer.

Estrogen

Hormonal replacement therapy, or HRT, not only helps maintain, but it can increase bone mass after menopause. Multiple studies have shown the benefits of estrogen therapy, including a lower risk of osteoporosis and fractured bones. In addition, other benefits of estrogen replacement in the postmenopausal patient include lower cholesterol, decreased risk of colon cancer, and fewer postmenopausal symptoms. HRT was shown to increase the risk of uterine cancer, but this risk is eliminated when the estrogen is combined with progesterone. There have been studies showing an increase risk of breast cancer in some study populations. Patients on HRT have also shown a slightly increased risk of developing blood clots and strokes.

Parathyroid Hormone (PTH)

PTH stimulates both resorption and new bone formation. Intermittent administration stimulates formation more than resorption. Clinical trials to date suggest that PTH therapy is effective in both the prevention and treatment of osteoporosis, and a preparation called Forteo, given by daily injection, is now FDA approved for the treatment of severe osteoporosis. Forteo is more effective at building spine bone density than any other treatment. However, because it requires daily injection, and because of its expense, it is usually reserved for patients with very severe spine osteoporosis.

Didronel

Didronel (etidronate disodium) acts primarily on bone. It can inhibit the formation, growth, and dissolution of hydroxyapatite crystals and their amorphous precursors by chemisorption to calcium phosphate surfaces. Inhibition of crystal resorption occurs at lower doses than are required to inhibit crystal growth.

Co-Administration with Anti-Ageing Drugs

In one embodiment the present invention relates to co-administration of one or more protease inhibitors targeting the exosite in PAPP-A such as PAC1 and/or PAC2 or any variant of PAC1 and/or PAC2 described in this document and one or more anti-ageing drug(s) such as the ones described below.

In one embodiment the present invention relates to co-administration of one or more protease inhibitors targeting the exosite in PAPP-A such as PAC1 and/or PAC2 or any variant of PAC1 and/or PAC2 described in this document and one or more anti-ageing drug(s) selected from the group consisting of antioxidants, Butylated hydroxytoluene (BHT), Ethoxyquin (dihydroethoxytrimethylquinolone), DDC (ammonium diethyldithiocarbamate), Vitamin E (alpha-tocopherol), MEA (mercaptoethylamaine), Diaminodiethyl DS (diaminodiethyl disulfide), Pantothenate, Vitamins, vitamin mixtures, minerals, mineral mixtures, Pyrodixonej (Vitamin B6), vitamin C, Vitamin A, Vitamin B12, Procaine, Deanol, Levodopa, Phenformin, Phenyloin, BHT, drugs which protect against radiation, a radioprotective drug such as MEA, drugs known to inhibit free radical reactions, ethoxyquin, NDHGA (nordihydroguaretic acid), proantocyanins, bioflavonoids, lycopenes, antioxidants from vegetables, diethylhydroxylamine (DEHA), EMHP, 2-ethyl-6-methyl-3-hydroxypyridine HCl, Co-enzyme Q10, Lipoic acid, Folic acid, Selenium, Flavonoids carotenes, DHEA, Vitamin B, Carnitin, SAM, Vinpocetine (Cavinton), Deprenyl (Eldepryl), Phyto-medicines, Herbs, HGH, Beta carotene, Folic acid, alpha lipoic acid, acetyl-l-carnitine, creatine, melatonin, fish oil such as 50% EPA/DHA, whey protein concentrate, mitochondrial Antioxidants such as R-Lipoic Acid, NtBHA, Idebenone and Chlorophyllin, SOD Modulators such as Deprenyl, Hydergine and Bacopa, Anti-Glycation Agents such as Pyridoxamine, Benfotiamine, Carnosine, ALT-711, Kinetin, Deprenyl, procaine, Chromium, Molybdenum, Potassium, Choline Bitartrate, Inositol, PABA, Flax Seed Powder, 5-HTP, Lutein, Lycopene, Glucosamine Sulfate, SAMe, Boron, Nickel, Silicon, Tin, Trace Mineral Blend, Vanadium, Bioflavonoid Concentrate, Ginkgo Extract, Green Tea Extract, L-Glutathione Reduced, L-Carnitine, L-Glutamine, DL-Phenylalanine, L-Tyrosine, Amino Acid Mix, GABA, vitamin A, vitamin D, vitamin K, Thiamin, Riboflavin, Niacin, Folate, Biotin, Pantothenic Acid, Calcium, Iodine, Magnesium, Zinc, Copper, Manganese, B3, Proleva, Human growth hormone and growth hormone.

In another embodiment the one or more anti-aging drugs comprises one or more drugs for treatment and/or prevention of specific diseases of aging such as Alzheimer's disease, Dementia, Arthritis, Cancer, Depression, Diabetes, Hyperlipidemia, Hypertension, Immune decline, Infections bacterial, Infections fungal, Memory loss, Menopause, Muscle weakness, Osteoporosis, Parkinson's disease, Prostate hyperplasia, Sexual disorders, Stroke risk, stroke, Weight gain and obesity.

EXAMPLES

The invention will be further described in the following examples, which do not limit the scope of the invention described in the claims.

Example 1

Plasmid Constructs

An expression construct encoding a His-tagged form of the C-terminal portion of murine PAPP-A, starting at module CCP1 (FIG. 1), was made by overlap extension PCR. Briefly, a nucleotide fragment encoding a signal peptide (MVLLTAVLLLLAAYAGPAQS) was derived by PCR from a construct encoding human IGFBP-5 (Gen Bank accession number NP_000590). The primers were 5'-GACGAAGCTTATGGTGTTGCTCACCGCGGT-3' (an introduced HindIII site is shown in bold), and 5'-TTCTGGGCAGTCGGCGCTCTGGGCCGGCCCGCAT-3' (nucleotides encoding residues 1129-1133 of murine PAPP-A are underlined. The numbering of the 1545-residue murine PAPP-A is according to (Soe, R., Overgaard, M. T., Thomsen, A. R., Laursen, L. S., Olsen, I. M., Sottrup-Jensen, L., Haaning, J., Giudice, L. C., Conover, C. A., and Oxvig, C. (2002) *Eur. J. Biochem.* 269(8), 2247-2256) The numbering of the 1547-residue human PAPP-A is according to (Kristensen, P., and Winter, G. (1998) *Fold Des* 3(5), 321-328). A second nucleotide fragment encoding residues 1129-1545 of murine PAPP-A followed by a His-tag, was made using pcDNA3.1-mPA, encoding murine PAPP-A, as a template. The primers were 5'-GGGCCGGCCCAGAGCGCCGACTGCCCAGAACTGGC-3' (murine PAPP-A-encoding nucleotides are underlined) and 5'-CATTTCTAGATCAATGATGATGATGATGATGTCCTGAGCCATGGCTATATCCCCGAAGATCTTTCC-3' (an XbaI site is shown in bold, nucleotides encoding residues Gly-Ser followed by six histidine residues are shown in italic, and murine PAPP-A-encoding nucleotides are underlined). The PCR product resulting from the combination of the two fragments was cloned into the HindIII/XbaI sites of pcDNA3.1(+) (Invitrogen), to obtain pmPA(CCP1-C-His), encoding murine PAPP-A residues 1129-1545 followed by the amino acid sequence GSHHHHHH. A similar construct, encoding residues 1133-1547 of human PAPP-A, has been made. This construct does not include a His-tag. Expression constructs encoding human PAPP-A, murine PAPP-A, human PAPP-A2, human PAPP-A/PAPP-A2 chimeric proteins (PAPP-A (P2-CCP5-C), PAPP-A(P2-CCP4-C), PAPP-A(P2-CCP3-C), PAPP-A(P2-CCP2-C), PAPP-A(P2-CCP1-C), PAPP-A (P2-CCP3-4), and PAPP-A(P2-LNR3), a truncated variants of PAPP-A (PAPP-A(dLNR3-C)), and variants of PAPP-A with single amino acids substituted into alanine, PAPP-A (D1484A), PAPP-A(D1499A), and PAPP-A(D1502A)), were also used for transfection. Finally, we used a construct encoding PAPP-A in which Glu-483 of the active site was replaced with glutamine, PAPP-A(E483Q).

Cell Culture and Expression of Protein in Mammalian Cells

Human embryonic kidney 293T cells (293tsA1609neo) were maintained in high-glucose Dulbecco's modified Eagle's medium supplemented with 10% fetal bovine serum, 2 mM glutamine, nonessential amino acids, and gentamicin (Invitrogen). Cells were plated onto 6-cm tissue culture dishes and were transiently transfected 18 h later by calcium phosphate co-precipitation using 10 µg of plasmid DNA prepared by QIAprep Spin Kit (Qiagen). After 48 h, the culture media were harvested, and cleared by centrifugation. Cells transfected with cDNA encoding murine PAPP-A(1129-1545), human PAPP-A(1133-1547), and human PAPP-A (E483Q), were further cultured in serum-free medium to facilitate purification.

Generation of Chicken Polyclonal Antibodies

Murine PAPP-A(1129-1545) was purified from serum-free medium by nickel affinity chromatography using Chelating Sepharose Fast Flow beads (1 mL) (Amersham Biosciences). The column was washed with 1 M NaCl, 50 mM sodium phosphate, pH 5.5, and bound protein was eluted with PBS containing 20 mM EDTA. Pooled fractions were further purified by heparin affinity chromatography using a 1 mL HiTrap Heparin HP column (Amersham Biosciences) equilibrated in PBS. The column was washed with PBS containing 250 mM NaCl, and bound protein was eluted with PBS containing 1 M NaCl.

Three chickens (Isa Brown) were immunized by intramuscular injections in the breast muscle using 15 µg of purified protein for each round. Complete Freund's adjuvant (Sigma) was used in the first round of injections, and incomplete Freund's adjuvant (Sigma) was used for successive rounds. Eggs were collected daily and kept at 4° C. Titers were evaluated at regular intervals by purification of IgY from yolk followed by a direct ELISA, in which murine PAPP-A(1129-1545) was coated onto plastic. Detection was done using HRP-conjugated anti-chicken-IgY (Sigma), and preparations of IgY with the highest titers were used for further experiments.

Measurement of Proteolytic Activity

Proteolytic activity of PAPP-A against IGFBP-4 and -5 was analyzed as previously described in detail (45). In brief, purified substrates, quantified by amino acid analysis, were labelled with $^{125}$I (Amersham Biosciences). Cleavage reactions were carried out in 50 mM Tris-HCl, 100 mM NaCl, 1 mM CaCl$_2$, pH 7.5 in the absence (IGFBP-5) or presence (IGFBP-4) of a 10 fold molar excess of IGF-II (Diagnostic Systems Laboratories). Following incubation at 37° C., reactions were quenched by the addition of EDTA (10 mM) and stored at −20° C. Cleavage products were separated by 10-20% SDS-PAGE and visualized by autoradiography. The degree of cleavage was determined by quantification of band intensities using a Typhoon imaging system (GE Healthcare), and background levels (mock signals) were subtracted. Proteolytic activity of PAPP-A2 against IGFBP-5 in the absence of IGF was analyzed similarly, as previously detailed (26). Analysis of peptidolytic activity against a 26-residue synthetic peptide derived from IGFBP-4 was carried out as previously described (46). Residues on the N-terminal and C-terminal side of the cleavage site were modified with o-aminobenzoic acid and substituted with 3-nitrotyrosine, respectively. The reaction buffer was 50 mM Tris, pH 8.0, 0.01% Tween-20. Light at 310 nm was used for excitation, and emission was detected at 420 nm. Quantitative analyses were carried out with Prism 5.0 (Graphpad Software) using the equation for competitive inhibition. In the case of partial inhibition sigmoidal dose-response curves were fitted to the data.

Screening of Semi-Synthetic Phage Libraries

Human PAPP-A(1133-1547) was immobilized (1 h at 37° C.) to 3.5 mL Immunotubes (Nunc Maxisorp), which were coated overnight at 4° C. with polyclonal PAPP-A antibodies (5 μg/mL) contained in 100 mM sodium bicarbonate, pH 9.8 and blocked with 3% skimmed milk powder in 20 mM Tris, 150 mM NaCl, pH 7.5 (TBS). We used a combination of two semi-synthetic phage libraries (Tomlinson I+J) (48), and capture of phages ($10^{12}$ from each library) was carried out for 2 h at RT while rotating gently. Following capture, the tubes were rinsed 10 times in TBS containing 1 M NaCl and 0.1% Tween-20 (TBST), further washed at 4° C. with 2 L TBST for five hours using a peristaltic pump, and finally rinsed five times with TBS. Elution of phages was carried out for 10 min at RT using 0.5 mL DPPC-treated trypsin (1 mg/mL) (Sigma) diluted in TBS. Alternatively, the elution of phages can comprise use of EDTA. Furthermore, other libraries known in the art than phage libraries can be used.

E. coli (TG1), infected (30 min at 37° C.) with the eluted phages, were plated on TYE plates supplemented with 1% glucose and ampicillin (100 μg/mL). Colonies were transferred to 96-well culture plates with 2×TY medium containing 1% glucose and ampicillin (100 μg/mL), and incubated (overnight at 37° C.). A replicate of each plate was incubated for 3 h, and KM13 helper phages were added ($10^9$ to each well). Following incubation for 1 h, the medium was changed to 2×TY containing ampicillin (100 μg/mL) and kanamycin (50 μg/mL), the plates were incubated for 20 h at 30° C., and phage-containing supernatants were then analyzed by ELISA for binding to human PAPP-A(E483Q), immobilized in 96-well plates with polyclonal PAPP-A antibodies. The plates were blocked with 2% bovine serum albumin (Sigma), washing was done with TBS containing 0.1% Tween-20, and detection was performed using HRP-conjugated anti-M13 (GE Healthcare). Phagemid DNA (pIT2) from selected clones was prepared and sequenced.

To also obtain phage antibodies which bind the region of PAPP-A N-terminal to CCP1, a similar screening was carried out using full-length human PAPP-A. Clone PAC5 was obtained and used as a control antibody in the scFv format. Clone PAC33, with specificity irrelevant to PAPP-A, was also used as a control antibody.

Expression and Purification of scFv Antibodies and Analysis of Inhibitory Potential E. coli HB2151 (nonsuppressor of amber stop codon) was infected with selected phages for the production of monoclonal scFv antibodies. Cultures of 1 L were induced for 4-16 h with 1 mM IPTG, and expressed proteins were purified by nickel affinity chromatography on Chelating Sepharose Fast Flow beads (5 mL) (GE Healthcare), following sonication. Washing was carried out with 20 mM imidazole, 100 mM NaCl, 50 mM sodium phosphate, pH 8.0. For elution, the concentration of imidazole was increased to 300 mM. Eluted protein was dialyzed into 20 mM Tris, 100 mM NaCl, pH 8. A MonoQ column (GE Healthcare) or a protein L column (Pierce) was used for further purification. The purified protein was dialyzed into the relevant buffers prior to functional analysis. Analysis of binding to PAPP-A, immobilized as described above, was carried out in 96-well plates using a HRP-conjugated anti-His-tag antibody (Sigma) for detection. Preparations of purified antibodies were quantified by amino acid analysis, and the effects of antibodies on PAPP-A activity were analyzed by the addition of controlled amounts to cleavage reactions. PAC33 was used as a negative control.

Surface Plasmon Resonance Analysis

Surface plasmon resonance experiments were carried out on a BIAcore T100 instrument (BIAcore AB, Uppsala, Sweden) using series S CM5 sensor chips and coupling reagents supplied by the manufacturer. Affinity purified PAPP-A (E483Q), 10 μg/mL in 10 mM sodium acetate, pH 5.0, was immobilized (at a level of 500 resonance units (RU)) to the activated chip at 25° C. Remaining activated groups were blocked by 1M ethanolamine. Purified antibodies (0.35-11 nM) diluted in 10 mM HEPES, 150 mM NaCl, 1 mM CaCl$_2$, 0.05% Tween-20, pH 7.4 (HBS), were injected over the sensor chip for 2 min at a flow rate of 30 μL/min at 37° C. Recorded signals were subtracted the background signal, determined by the injection of an irrelevant antibody. For the analysis of calcium ion dependence, some experiments were carried out using 175 nM PAC1 in the absence or presence of 10 mM EDTA. Data were analyzed using the software of the manufacturer (BIAcore T100 evaluation Software version 1.1).

Determination of Antibody Specificity and Mapping of Antibody Binding

Mapping of antibody binding was carried out by ELISA using PAPP-A/PAPP-A2 chimeric proteins, and mutated variants of PAPP-A. The proteins were immobilized with polyclonal PAPP-A antibodies, and binding of phage antibodies were analyzed as detailed above.

Results

Inhibition of Proteolysis by Polyclonal Antibodies Raised Against a C-Terminal Fragment of PAPP-A—

The only known physiological inhibitor of PAPP-A proteolytic activity is the proform of eosinophil major basic protein (proMBP), which inactivates PAPP-A by the formation of a covalent disulfide based 2:2 complex, denoted PAPP-A/proMBP. Although inhibition by proMBP is irreversible, the process of complex formation is relatively slow and sensitive to redox potential. Of synthetic low-molecular weight compounds, such as many inhibitors of the related matrix metalloproteinases (MMPs), none has been found for PAPP-A.

However, PAPP-A activity towards both IGFBP-4 and -5 was effectively inhibited by polyclonal antibodies (FIG. 2A). Because we have previously hypothesized that the LNR3 region of PAPP-A is involved as an exosite in substrate binding, we wanted to test the inhibitory properties of antibodies raised against the C-terminal region of PAPP-A. We made a plasmid construct encoding residues 1129-1545 of murine PAPP-A, including the five CCP modules and LNR3 (FIG. 1), and recombinant protein, expressed in 293T cells, was purified (FIG. 2B) for immunization. Because PAPP-A LNR3 is highly conserved (100% identity between human and murine PAPP-A LNR3) and therefore less likely to elicit an immune response in mammals, chickens were chosen for immunization. The resulting polyclonal IgY antibodies were found to effectively inhibit PAPP-A proteolysis of IGFBP-4, while cleavage of IGFBP-5 was much less affected (FIG. 2C). No effect on proteolysis of the two substrates was observed with preimmune IgY (not shown).

Although many epitopes outside the LNR3 region exist on the approximately 60 kDa C-terminal fragment used for immunization, this experiment supports the hypothesis that LNR3 functions as a substrate binding exosite. Furthermore, the finding that such polyclonal antibodies cannot efficiently inhibit cleavage of IGFBP-5, suggests a differential mode of substrate binding, and that an inhibitor which selectively targets PAPP-A cleavage of IGFBP-4 can be obtained.

Selection by Phage Display of PAPP-A Monoclonal scFv Antibodies Inhibitory of IGFBP-4 Proteolysis—

To obtain a monoclonal antibody with selective inhibitory activity against PAPP-A cleavage of IGFBP-4, a phage antibody library was screened for binding to the 60 kDa C-terminal fragment of human PAPP-A (residues 1133-1547), as detailed in Experimental Procedures. To increase chances of obtaining a phage antibody which binds to the conserved LNR3 region, we used a combination of two semi-synthetic phage libraries, which are built on a framework of commonly used single VH and VL human gene segments. Bound phages were cloned, their binding to full-length PAPP-A was evaluated by ELISA, and scFv antibodies from selected phages were then produced in *E. coli* and assessed for inhibitory activity. Two inhibitory scFv antibodies, PAC1 and PAC2, were obtained. Sequence analysis of the variable regions showed that PAC1 and PAC2 were unique clones (not shown).

For further characterization, PAC1 and PAC2 were expressed at a larger scale, purified, and quantified by amino acid analysis. Both scFv antibodies effectively inhibited PAPP-A cleavage of IGFBP-4, as illustrated with PAC1 (FIG. 3A). Efficient inhibition of murine PAPP-A was also found with PAC1 (FIG. 3B) and PAC2, in agreement with the high degree of sequence conservation between murine and human PAPP-A. For both human and murine PAPP-A, PAC1 was a slightly better inhibitor than PAC2 (not shown).

Inhibition of human PAPP-A was further analyzed by plotting relative initial velocities as a function of antibody concentration (FIG. 3B). Based on this analysis, the inhibitory constant of PAC1 towards human PAPP-A was determined ($K_i$=1.2 nM). Antibody binding to immobilized PAPP-A was further analyzed by surface plasmon resonance, from which we obtained an equilibrium dissociation constant for PAC1 ($K_D$=0.25 nM, FIG. 3C), in agreement with the solution phase experiments.

PAPP-A Activity Against IGFBP-5 is Only Partially Inhibited by Antibody PAC1—

Antibody PAC1 showed much less inhibitory activity against PAPP-A cleavage of IGFBP-5 compared to IGFBP-4, as illustrated by an end-point assay (FIG. 4A), and further analyzed quantitatively (FIG. 4B). At saturating concentrations of PAC1, PAPP-A still showed about 45% activity against IGFBP-5, possibly because PAPP-A activity against IGFBP-5 is reduced only by steric hindrance rather than direct interference with enzyme-substrate binding.

Interestingly, PAPP-A cleavage of a synthetic peptide derived from IGFBP-4 (46) was not inhibited by PAC1 (FIGS. 5A and B). Therefore, binding of PAC1 to PAPP-A does not cause an altered structure of the active site environment. This is in contrast to the inhibitory properties of a PAPP-A monoclonal antibody (mAb), PA-1A (45), which efficiently inhibited cleavage of this peptide (FIGS. 5C and D). However, mAb PA-1A was a poor inhibitor of both intact IGFBP-4 (FIG. 6A) and IGFBP-5 (FIG. 6B). In both cases, about 40% of PAPP-A activity remained at saturating concentrations of mAb PA-1A, in striking contrast to the efficient inhibition against IGFBP-4 cleavage obtained with PAC1 (FIG. 3B). Most likely, mAb PA-1A recognizes an epitope of PAPP-A, which is located at or close to the active site. In agreement with this, mAb PA-1A did not bind to the C-terminal fragment of human PAPP-A (residues 1133-1547) (not shown).

Antibody PAC1 Binds to LNR3 and Depends on Calcium Ions—

Efficient inhibition of murine PAPP-A cleavage of IGFBP-4 was found with PAC1 (FIG. 7A) and PAC2 (not shown), in agreement with the high degree of sequence conservation between murine and human PAPP-A. However, we found that neither PAC1 nor PAC2 had any effect on the activity of the homologue PAPP-A2 towards its two known substrates, IGFBP-3 (not shown) and IGFBP-5 (FIG. 7). Hence, to delineate the binding of PAC1 to PAPP-A, a set of chimeras, in which a variable portion of the C-terminal was exchanged with the sequence of PAPP-A2, were analyzed. Only constructs, in which the sequence of LNR3 was derived from PAPP-A, showed binding of PAC1 (FIG. 8A) and PAC2 (not shown). Also, PAC1 did not show any binding to a mutant of PAPP-A truncated on the N-terminal side of LNR3 (FIG. 8A).

Because the LNR modules of PAPP-A have been suggested to coordinate calcium ions, the possible dependence of calcium ions for PAC1 binding was assessed by surface plasmon resonance. Binding to immobilized PAPP-A was observed in the presence of calcium ions (FIGS. 8B and 3C), but no binding was seen when both the sample and the flow cell was equilibrated with the chelator EDTA (not shown). However, the binding was only disturbed when PAC1 was injected with EDTA onto a chip equilibrated with the calcium ion containing buffer (FIG. 8B). Following EDTA treatment, equilibration of the flow cell using calcium ion containing buffer restored its ability to bind PAC1 (FIG. 8B). Hence, calcium ions are required for PAC1 binding to PAPP-A, and the removal of calcium from LNR3 by EDTA is a reversible process. Similar results were obtained with PAC2 (not shown).

Based on these results, we analyzed antibody binding to mutants of LNR3, in which the three single acid residues predicted to coordinate a calcium ion were individually substituted with alanine. In agreement with the mapping data using PAPP-A/PAPP-A2 chimeras and with the surface plasmon resonance experiment data, PAC1 and PAC2 showed no binding to these mutants (FIG. 8C).

Example 2

Binding of PAC1 and PAC2 to mutants of human PAPP-A, in which single amino acid residues within the C-terminal 70 residues have been substituted into alanine:

|  | PAC1 | PAC2 |
| --- | --- | --- |
| D1484A | no binding | no binding |
| D1499A | no binding | no binding |
| D1502A | no binding | no binding |
| K1509A | binding | binding |
| D1521A | weak binding | weak binding |
| D1525A | binding | binding |
| R1529A | no binding | no binding |
| D1530A | no binding | no binding |
| E1535A | binding | binding |

Example 3

Binding of PAC5 to fragments of human PAPP-A (SEQ ID NO:1).

"PA 1-950" is a fragment of PAPP-A comprising amino acid residues 1-950. "PA 937-1547" is a fragment of PAPP-A comprising amino acid residues 937-1547. "PA 1-599" is a fragment of PAPP-A comprising amino acid residues 1-599.

| Mapping of PAC5 binding to PAPP-A | |
| --- | --- |
| PA 1-950 | binding |
| PA 937-1547 | no binding |
| PA 1-599 | no binding |

The invention claimed is:

1. An isolated polypeptide consisting of SEQ ID NO:2 or SEQ ID NO:3, or a polypeptide consisting of a fragment of SEQ ID NO:3 containing 28 or more consecutive amino acid residues of SEQ ID NO:3, wherein said polypeptide is capable of binding to an antibody or fragment thereof that binds to and inhibits an activity of PAPP-A.

2. An isolated polypeptide variant of SEQ ID NO:2 or SEQ ID NO:3 having at least 90% sequence identity with SEQ ID NO:2 or SEQ ID NO:3, or an isolated polypeptide variant of a fragment of SEQ ID NO:2 or SEQ ID NO:3 having at least 90% sequence identity with a fragment of SEQ ID NO:2 or SEQ ID NO:3, wherein said polypeptide variant comprises one or more conservative substitutions as compared to SEQ ID NO:2, SEQ ID NO:3, or a fragment thereof.

3. The isolated polypeptide variant of claim 2, wherein the polypeptide variant has at least 95% sequence identity to SEQ ID NO:2 or SEQ ID NO:3, or to a fragment of SEQ ID NO:2 or SEQ ID NO:3.

4. The isolated polypeptide of claim 1 or the isolated polypeptide variant of claim 2, wherein one or more amino acid residues of the polypeptide or polypeptide variant are modified by acetylation, carboxylation, glycosylation, or phosphorylation.

5. An acid addition salt of the polypeptide of claim 1 or the polypeptide variant of claim 2, said salt being obtainable by treating the polypeptide with an inorganic acid to provide a water soluble salt of the polypeptide.

6. A composition comprising the isolated polypeptide of claim 1 or the isolated polypeptide variant of claim 2 in combination with a physiologically or pharmaceutically acceptable carrier.

7. The composition of claim 6, further comprising one or more additional bioactive agent(s).

8. The composition of claim 7, wherein the one or more additional bioactive agent(s) are selected from the group consisting of anti-platelet agents, anti-coagulation agents, fibrinolytic agents, drugs for treatment of cardiovascular diseases, drugs for treatment of osteoporosis, and anti-cancer drugs.

9. A kit comprising the polypeptide of claim 1, the polypeptide variant of claim 2, or the composition of claim 6, and at least one additional component.

10. The kit of claim 9, wherein the at least one additional component is a bioactive agent selected from the group consisting of anti-platelet agents, anti-coagulation agents, fibrinolytic agents, drugs for treatment of cardiovascular diseases, drugs for treatment of osteoporosis, and anti-cancer drugs.

11. The kit of claim 10, wherein the at least one or more additional component is an anticancer drug.

12. The kit of claim 10, wherein the at least one additional component is a drug for the treatment of osteoporosis.

13. The kit of claim 10, wherein the at least one additional component is a drug for the treatment of cardiovascular disease.

14. The kit of claim 9, wherein the at least one additional component is an adjuvant, selected from the group consisting of mineral, bacterial, plant, synthetic, or host product adjuvants.

15. A complex comprising an isolated polypeptide consisting of a PAPP-A exosite selected from the group consisting of SEQ ID NO:2, SEQ ID NO:3, and fragments of SEQ ID NO:3, and a binding partner having affinity for said exosite, wherein binding of the binding partner to the exosite within PAPP-A alters the activity of PAPP-A.

* * * * *

SEQUENCE LISTING

```
<160> NUMBER OF SEQ ID NOS: 7

<210> SEQ ID NO 1
<211> LENGTH: 1547
<212> TYPE: PRT
<213> ORGANISM: homo sapiens

<400> SEQUENCE: 1

Glu Ala Arg Gly Ala Thr Glu Glu Pro Ser Pro Pro Ser Arg Ala Leu
1               5                   10                  15

Tyr Phe Ser Gly Arg Gly Glu Gln Leu Arg Val Leu Arg Ala Asp Leu
                20                  25                  30

Glu Leu Pro Arg Asp Ala Phe Thr Leu Gln Val Trp Leu Arg Ala Glu
            35                  40                  45

Gly Gly Gln Arg Ser Pro Ala Val Ile Thr Gly Leu Tyr Asp Lys Cys
    50                  55                  60

Ser Tyr Ile Ser Arg Asp Arg Gly Trp Val Val Gly Ile His Thr Ile
65                  70                  75                  80

Ser Asp Gln Asp Asn Lys Asp Pro Arg Tyr Phe Phe Ser Leu Lys Thr
                85                  90                  95

Asp Arg Ala Arg Gln Val Thr Thr Ile Asn Ala His Arg Ser Tyr Leu
            100                 105                 110

Pro Gly Gln Trp Val Tyr Leu Ala Ala Thr Tyr Asp Gly Gln Phe Met
        115                 120                 125

Lys Leu Tyr Val Asn Gly Ala Gln Val Ala Thr Ser Gly Glu Gln Val
    130                 135                 140

Gly Gly Ile Phe Ser Pro Leu Thr Gln Lys Cys Lys Val Leu Met Leu
145                 150                 155                 160

Gly Gly Ser Ala Leu Asn His Asn Tyr Arg Gly Tyr Ile Glu His Phe
                165                 170                 175

Ser Leu Trp Lys Val Ala Arg Thr Gln Arg Glu Ile Leu Ser Asp Met
            180                 185                 190

Glu Thr His Gly Ala His Thr Ala Leu Pro Gln Leu Leu Leu Gln Glu
```

```
              195                 200                 205
Asn Trp Asp Asn Val Lys His Ala Trp Ser Pro Met Lys Asp Gly Ser
210                 215                 220
Ser Pro Lys Val Glu Phe Ser Asn Ala His Gly Phe Leu Leu Asp Thr
225                 230                 235                 240
Ser Leu Glu Pro Pro Leu Cys Gly Gln Thr Leu Cys Asp Asn Thr Glu
            245                 250                 255
Val Ile Ala Ser Tyr Asn Gln Leu Ser Ser Phe Arg Gln Pro Lys Val
            260                 265                 270
Val Arg Tyr Arg Val Val Asn Leu Tyr Glu Asp Asp His Lys Asn Pro
        275                 280                 285
Thr Val Thr Arg Glu Gln Val Asp Phe Gln His Gln Leu Ala Glu
    290                 295                 300
Ala Phe Lys Gln Tyr Asn Ile Ser Trp Glu Leu Asp Val Leu Glu Val
305                 310                 315                 320
Ser Asn Ser Ser Leu Arg Arg Arg Leu Ile Leu Ala Asn Cys Asp Ile
                325                 330                 335
Ser Lys Ile Gly Asp Glu Asn Cys Asp Pro Glu Cys Asn His Thr Leu
            340                 345                 350
Thr Gly His Asp Gly Gly Asp Cys Arg His Leu Arg His Pro Ala Phe
            355                 360                 365
Val Lys Lys Gln His Asn Gly Val Cys Asp Met Asp Cys Asn Tyr Glu
        370                 375                 380
Arg Phe Asn Phe Asp Gly Gly Glu Cys Cys Asp Pro Glu Ile Thr Asn
385                 390                 395                 400
Val Thr Gln Thr Cys Phe Asp Pro Asp Ser Pro His Arg Ala Tyr Leu
                405                 410                 415
Asp Val Asn Glu Leu Lys Asn Ile Leu Lys Leu Asp Gly Ser Thr His
            420                 425                 430
Leu Asn Ile Phe Phe Ala Lys Ser Ser Glu Glu Leu Ala Gly Val
        435                 440                 445
Ala Thr Trp Pro Trp Asp Lys Glu Ala Leu Met His Leu Gly Gly Ile
    450                 455                 460
Val Leu Asn Pro Ser Phe Tyr Gly Met Pro Gly His Thr His Thr Met
465                 470                 475                 480
Ile His Glu Ile Gly His Ser Leu Gly Leu Tyr His Val Phe Arg Gly
                485                 490                 495
Ile Ser Glu Ile Gln Ser Cys Ser Asp Pro Cys Met Gly Thr Glu Pro
            500                 505                 510
Ser Phe Glu Thr Gly Asp Leu Cys Asn Asp Thr Asn Pro Ala Pro Lys
            515                 520                 525
His Lys Ser Cys Gly Asp Pro Gly Pro Gly Asn Asp Thr Cys Gly Phe
        530                 535                 540
His Ser Phe Phe Asn Thr Pro Tyr Asn Asn Phe Met Ser Tyr Ala Asp
545                 550                 555                 560
Asp Asp Cys Thr Asp Ser Phe Thr Pro Asn Gln Val Ala Arg Met His
                565                 570                 575
Cys Tyr Leu Asp Leu Val Tyr Gln Gly Trp Gln Pro Ser Arg Lys Pro
            580                 585                 590
Ala Pro Val Ala Leu Ala Pro Gln Val Leu Gly His Thr Thr Asp Ser
        595                 600                 605
Val Thr Leu Glu Trp Phe Pro Pro Ile Asp Gly His Phe Phe Glu Arg
    610                 615                 620
```

-continued

Glu Leu Gly Ser Ala Cys His Leu Cys Leu Glu Gly Arg Ile Leu Val
625                 630                 635                 640

Gln Tyr Ala Ser Asn Ala Ser Ser Pro Met Pro Cys Ser Pro Ser Gly
            645                 650                 655

His Trp Ser Pro Arg Glu Ala Glu Gly His Pro Asp Val Glu Gln Pro
            660                 665                 670

Cys Lys Ser Ser Val Arg Thr Trp Ser Pro Asn Ser Ala Val Asn Pro
            675                 680                 685

His Thr Val Pro Pro Ala Cys Pro Glu Pro Gln Gly Cys Tyr Leu Glu
            690                 695                 700

Leu Glu Phe Leu Tyr Pro Leu Val Pro Glu Ser Leu Thr Ile Trp Val
705                 710                 715                 720

Thr Phe Val Ser Thr Asp Trp Asp Ser Ser Gly Ala Val Asn Asp Ile
            725                 730                 735

Lys Leu Leu Ala Val Ser Gly Lys Asn Ile Ser Leu Gly Pro Gln Asn
            740                 745                 750

Val Phe Cys Asp Val Pro Leu Thr Ile Arg Leu Trp Asp Val Gly Glu
            755                 760                 765

Glu Val Tyr Gly Ile Gln Ile Tyr Thr Leu Asp Glu His Leu Glu Ile
            770                 775                 780

Asp Ala Ala Met Leu Thr Ser Thr Ala Asp Thr Pro Leu Cys Leu Gln
785                 790                 795                 800

Cys Lys Pro Leu Lys Tyr Lys Val Val Arg Asp Pro Pro Leu Gln Met
            805                 810                 815

Asp Val Ala Ser Ile Leu His Leu Asn Arg Lys Phe Val Asp Met Asp
            820                 825                 830

Leu Asn Leu Gly Ser Val Tyr Gln Tyr Trp Val Ile Thr Ile Ser Gly
            835                 840                 845

Thr Glu Glu Ser Glu Pro Ser Pro Ala Val Thr Tyr Ile His Gly Arg
850                 855                 860

Gly Tyr Cys Gly Asp Gly Ile Ile Gln Lys Asp Gln Gly Glu Gln Cys
865                 870                 875                 880

Asp Asp Met Asn Lys Ile Asn Gly Asp Gly Cys Ser Leu Phe Cys Arg
            885                 890                 895

Gln Glu Val Ser Phe Asn Cys Ile Asp Glu Pro Ser Arg Cys Tyr Phe
            900                 905                 910

His Asp Gly Asp Gly Val Cys Glu Glu Phe Glu Gln Lys Thr Ser Ile
            915                 920                 925

Lys Asp Cys Gly Val Tyr Thr Pro Gln Gly Phe Leu Asp Gln Trp Ala
            930                 935                 940

Ser Asn Ala Ser Val Ser His Gln Asp Gln Gln Cys Pro Gly Trp Val
945                 950                 955                 960

Ile Ile Gly Gln Pro Ala Ala Ser Gln Val Cys Arg Thr Lys Val Ile
            965                 970                 975

Asp Leu Ser Glu Gly Ile Ser Gln His Ala Trp Tyr Pro Cys Thr Ile
            980                 985                 990

Ser Tyr Pro Tyr Ser Gln Leu Ala Gln Thr Thr Phe Trp Leu Arg Ala
            995                 1000                1005

Tyr Phe Ser Gln Pro Met Val Ala Ala Ala Val Ile Val His Leu
            1010                1015                1020

Val Thr Asp Gly Thr Tyr Tyr Gly Asp Gln Lys Gln Glu Thr Ile
            1025                1030                1035

Ser Val Gln Leu Leu Asp Thr Lys Asp Gln Ser His Asp Leu Gly
            1040                1045                1050

```
Leu His Val Leu Ser Cys Arg Asn Asn Pro Leu Ile Ile Pro Val
1055                1060                1065

Val His Asp Leu Ser Gln Pro Phe Tyr His Ser Gln Ala Val Arg
1070                1075                1080

Val Ser Phe Ser Ser Pro Leu Val Ala Ile Ser Gly Val Ala Leu
1085                1090                1095

Arg Ser Phe Asp Asn Phe Asp Pro Val Thr Leu Ser Ser Cys Gln
1100                1105                1110

Arg Gly Glu Thr Tyr Ser Pro Ala Glu Gln Ser Cys Val His Phe
1115                1120                1125

Ala Cys Glu Lys Thr Asp Cys Pro Glu Leu Ala Val Glu Asn Ala
1130                1135                1140

Ser Leu Asn Cys Ser Ser Ser Asp Arg Tyr His Gly Ala Gln Cys
1145                1150                1155

Thr Val Ser Cys Arg Thr Gly Tyr Val Leu Gln Ile Arg Arg Asp
1160                1165                1170

Asp Glu Leu Ile Lys Ser Gln Thr Gly Pro Ser Val Thr Val Thr
1175                1180                1185

Cys Thr Glu Gly Lys Trp Asn Lys Gln Val Ala Cys Glu Pro Val
1190                1195                1200

Asp Cys Ser Ile Pro Asp His His Gln Val Tyr Ala Ala Ser Phe
1205                1210                1215

Ser Cys Pro Glu Gly Thr Thr Phe Gly Ser Gln Cys Ser Phe Gln
1220                1225                1230

Cys Arg His Pro Ala Gln Leu Lys Gly Asn Asn Ser Leu Leu Thr
1235                1240                1245

Cys Met Glu Asp Gly Leu Trp Ser Phe Pro Glu Ala Leu Cys Glu
1250                1255                1260

Leu Met Cys Leu Ala Pro Pro Pro Val Pro Asn Ala Asp Leu Gln
1265                1270                1275

Thr Ala Arg Cys Arg Glu Asn Lys His Lys Val Gly Ser Phe Cys
1280                1285                1290

Lys Tyr Lys Cys Lys Pro Gly Tyr His Val Pro Gly Ser Ser Arg
1295                1300                1305

Lys Ser Lys Lys Arg Ala Phe Lys Thr Gln Cys Thr Gln Asp Gly
1310                1315                1320

Ser Trp Gln Glu Gly Ala Cys Val Pro Val Thr Cys Asp Pro Pro
1325                1330                1335

Pro Pro Lys Phe His Gly Leu Tyr Gln Cys Thr Asn Gly Phe Gln
1340                1345                1350

Phe Asn Ser Glu Cys Arg Ile Lys Cys Glu Asp Ser Asp Ala Ser
1355                1360                1365

Gln Gly Leu Gly Ser Asn Val Ile His Cys Arg Lys Asp Gly Thr
1370                1375                1380

Trp Asn Gly Ser Phe His Val Cys Gln Glu Met Gln Gly Gln Cys
1385                1390                1395

Ser Val Pro Asn Glu Leu Asn Ser Asn Leu Lys Leu Gln Cys Pro
1400                1405                1410

Asp Gly Tyr Ala Ile Gly Ser Glu Cys Ala Thr Ser Cys Leu Asp
1415                1420                1425

His Asn Ser Glu Ser Ile Ile Leu Pro Met Asn Val Thr Val Arg
1430                1435                1440

Asp Ile Pro His Trp Leu Asn Pro Thr Arg Val Glu Arg Val Val
```

```
                1445                1450                1455

Cys Thr Ala Gly Leu Lys Trp Tyr Pro His Pro Ala Leu Ile His
    1460                1465                1470

Cys Val Lys Gly Cys Glu Pro Phe Met Gly Asp Asn Tyr Cys Asp
    1475                1480                1485

Ala Ile Asn Asn Arg Ala Phe Cys Asn Tyr Asp Gly Gly Asp Cys
    1490                1495                1500

Cys Thr Ser Thr Val Lys Thr Lys Lys Val Thr Pro Phe Pro Met
    1505                1510                1515

Ser Cys Asp Leu Gln Gly Asp Cys Ala Cys Arg Asp Pro Gln Ala
    1520                1525                1530

Gln Glu His Ser Arg Lys Asp Leu Arg Gly Tyr Ser His Gly
    1535                1540                1545

<210> SEQ ID NO 2
<211> LENGTH: 415
<212> TYPE: PRT
<213> ORGANISM: homo sapiens

<400> SEQUENCE: 2

Thr Asp Cys Pro Glu Leu Ala Val Glu Asn Ala Ser Leu Asn Cys Ser
1               5                   10                  15

Ser Ser Asp Arg Tyr His Gly Ala Gln Cys Thr Val Ser Cys Arg Thr
            20                  25                  30

Gly Tyr Val Leu Gln Ile Arg Arg Asp Asp Glu Leu Ile Lys Ser Gln
        35                  40                  45

Thr Gly Pro Ser Val Thr Val Thr Cys Thr Glu Gly Lys Trp Asn Lys
    50                  55                  60

Gln Val Ala Cys Glu Pro Val Asp Cys Ser Ile Pro Asp His His Gln
65                  70                  75                  80

Val Tyr Ala Ala Ser Phe Ser Cys Pro Glu Gly Thr Thr Phe Gly Ser
                85                  90                  95

Gln Cys Ser Phe Gln Cys Arg His Pro Ala Gln Leu Lys Gly Asn Asn
            100                 105                 110

Ser Leu Leu Thr Cys Met Glu Asp Gly Leu Trp Ser Phe Pro Glu Ala
        115                 120                 125

Leu Cys Glu Leu Met Cys Leu Ala Pro Pro Val Pro Asn Ala Asp
    130                 135                 140

Leu Gln Thr Ala Arg Cys Arg Glu Asn Lys His Lys Val Gly Ser Phe
145                 150                 155                 160

Cys Lys Tyr Lys Cys Lys Pro Gly Tyr His Val Pro Gly Ser Ser Arg
                165                 170                 175

Lys Ser Lys Lys Arg Ala Phe Lys Thr Gln Cys Thr Gln Asp Gly Ser
            180                 185                 190

Trp Gln Glu Gly Ala Cys Val Pro Val Thr Cys Asp Pro Pro Pro
        195                 200                 205

Lys Phe His Gly Leu Tyr Gln Cys Thr Asn Gly Phe Gln Phe Asn Ser
    210                 215                 220

Glu Cys Arg Ile Lys Cys Glu Asp Ser Asp Ala Ser Gln Gly Leu Gly
225                 230                 235                 240

Ser Asn Val Ile His Cys Arg Lys Asp Gly Thr Trp Asn Gly Ser Phe
                245                 250                 255

His Val Cys Gln Glu Met Gln Gly Gln Cys Ser Val Pro Asn Glu Leu
            260                 265                 270

Asn Ser Asn Leu Lys Leu Gln Cys Pro Asp Gly Tyr Ala Ile Gly Ser
```

```
                    275                 280                 285
Glu Cys Ala Thr Ser Cys Leu Asp His Asn Ser Glu Ser Ile Ile Leu
290                 295                 300

Pro Met Asn Val Thr Val Arg Asp Ile Pro His Trp Leu Asn Pro Thr
305                 310                 315                 320

Arg Val Glu Arg Val Val Cys Thr Ala Gly Leu Lys Trp Tyr Pro His
                325                 330                 335

Pro Ala Leu Ile His Cys Val Lys Gly Cys Glu Pro Phe Met Gly Asp
                340                 345                 350

Asn Tyr Cys Asp Ala Ile Asn Asn Arg Ala Phe Cys Asn Tyr Asp Gly
            355                 360                 365

Gly Asp Cys Cys Thr Ser Thr Val Lys Thr Lys Val Thr Pro Phe
        370                 375                 380

Pro Met Ser Cys Asp Leu Gln Gly Asp Cys Ala Cys Arg Asp Pro Gln
385                 390                 395                 400

Ala Gln Glu His Ser Arg Lys Asp Leu Arg Gly Tyr Ser His Gly
                405                 410                 415

<210> SEQ ID NO 3
<211> LENGTH: 70
<212> TYPE: PRT
<213> ORGANISM: homo sapiens

<400> SEQUENCE: 3

Cys Glu Pro Phe Met Gly Asp Asn Tyr Cys Asp Ala Ile Asn Asn Arg
1               5                   10                  15

Ala Phe Cys Asn Tyr Asp Gly Gly Asp Cys Cys Thr Ser Thr Val Lys
                20                  25                  30

Thr Lys Val Thr Pro Phe Pro Met Ser Cys Asp Leu Gln Gly Asp
            35                  40                  45

Cys Ala Cys Arg Asp Pro Gln Ala Gln Glu His Ser Arg Lys Asp Leu
    50                  55                  60

Arg Gly Tyr Ser His Gly
65                  70

<210> SEQ ID NO 4
<211> LENGTH: 70
<212> TYPE: PRT
<213> ORGANISM: mus musculus

<400> SEQUENCE: 4

Cys Glu Pro Phe Met Gly Asp Asn Tyr Cys Asp Ala Ile Asn Asn Arg
1               5                   10                  15

Ala Phe Cys Asn Tyr Asp Gly Gly Asp Cys Cys Thr Ser Thr Val Lys
                20                  25                  30

Thr Lys Val Thr Pro Phe Pro Met Ser Cys Asp Leu Gln Asn Asp
            35                  40                  45

Cys Ala Cys Arg Asp Pro Glu Ala Gln Glu His Asn Arg Lys Asp Leu
    50                  55                  60

Arg Gly Tyr Ser His Gly
65                  70

<210> SEQ ID NO 5
<211> LENGTH: 266
<212> TYPE: PRT
<213> ORGANISM: Isa Brown

<400> SEQUENCE: 5
```

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Ile Thr Asp Met Gly Arg Thr Thr Arg Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Leu Arg Gln Phe Asp Tyr Trp Gly Gln Gly Thr Leu Val
            100                 105                 110

Thr Val Ser Ser Gly Gly Gly Ser Gly Gly Gly Ser Gly Gly
        115                 120                 125

Gly Gly Ser Thr Asp Ile Gln Met Thr Gln Ser Pro Ser Ser Leu Ser
        130                 135                 140

Ala Ser Val Gly Asp Arg Val Thr Ile Thr Cys Arg Ala Ser Gln Ser
145                 150                 155                 160

Ile Ser Ser Tyr Leu Asn Trp Tyr Gln Gln Lys Pro Gly Lys Ala Pro
                165                 170                 175

Lys Leu Leu Ile Tyr His Ala Ser Gln Leu Gln Ser Gly Val Pro Ser
            180                 185                 190

Arg Phe Ser Gly Ser Gly Ser Gly Thr Asp Phe Thr Leu Thr Ile Ser
        195                 200                 205

Ser Leu Gln Pro Glu Asp Phe Ala Thr Tyr Tyr Cys Gln Gln Tyr Gly
210                 215                 220

Gly Asn Pro Thr Thr Phe Gly Gln Gly Thr Lys Val Glu Ile Lys Arg
225                 230                 235                 240

Ala Ala Ala His His His His His His Gly Ala Ala Glu Gln Lys Leu
                245                 250                 255

Ile Ser Glu Glu Asp Leu Asn Gly Ala Ala
            260                 265

<210> SEQ ID NO 6
<211> LENGTH: 266
<212> TYPE: PRT
<213> ORGANISM: Isa Brown

<400> SEQUENCE: 6

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Gln Ala Asp Gly Thr Arg Thr Gly Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Arg Gly Ile Phe Asp Tyr Trp Gly Gln Gly Thr Leu Val
            100                 105                 110
```

```
Thr Val Ser Ser Gly Gly Gly Ser Gly Gly Ser Gly Gly
        115                 120                 125
Gly Gly Ser Thr Asp Ile Gln Met Thr Gln Ser Pro Ser Ser Leu Ser
    130                 135                 140
Ala Ser Val Gly Asp Arg Val Thr Ile Thr Cys Arg Ala Ser Gln Ser
145                 150                 155                 160
Ile Ser Ser Tyr Leu Asn Trp Tyr Gln Gln Lys Pro Gly Lys Ala Pro
                165                 170                 175
Lys Leu Leu Ile Tyr Arg Ala Ser Gly Leu Gln Ser Gly Val Pro Ser
            180                 185                 190
Arg Phe Ser Gly Ser Gly Ser Gly Thr Asp Phe Thr Leu Thr Ile Ser
        195                 200                 205
Ser Leu Gln Pro Glu Asp Phe Ala Thr Tyr Tyr Cys Gln Gln Ser His
    210                 215                 220
His Tyr Pro Ser Thr Phe Gly Gln Gly Thr Lys Val Glu Ile Lys Arg
225                 230                 235                 240
Ala Ala Ala His His His His His Gly Ala Ala Glu Gln Lys Leu
                245                 250                 255
Ile Ser Glu Glu Asp Leu Asn Gly Ala Ala
            260                 265

<210> SEQ ID NO 7
<211> LENGTH: 266
<212> TYPE: PRT
<213> ORGANISM: Isa Brown

<400> SEQUENCE: 7

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Ala Met Ser Trp Val Arg Gln Ala Pro Gly Lys Gly Leu Glu Trp Val
        35                  40                  45
Ser Ala Ile Ser Pro Ala Gly Val Met Thr Gln Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Lys Gln Gln Gly Gly Phe Asp Tyr Trp Gly Gln Gly Thr Leu Val
            100                 105                 110
Thr Val Ser Ser Gly Gly Gly Ser Gly Gly Gly Ser Gly Gly
        115                 120                 125
Gly Gly Ser Thr Asp Ile Gln Met Thr Gln Ser Pro Ser Ser Leu Ser
    130                 135                 140
Ala Ser Val Gly Asp Arg Val Thr Ile Thr Cys Arg Ala Ser Gln Ser
145                 150                 155                 160
Ile Ser Ser Tyr Leu Asn Trp Tyr Gln Gln Lys Pro Gly Lys Ala Pro
                165                 170                 175
Lys Leu Leu Ile Tyr Arg Ala Ser Ala Leu Gln Ser Gly Val Pro Ser
            180                 185                 190
Arg Phe Ser Gly Ser Gly Ser Gly Thr Asp Phe Thr Leu Thr Ile Ser
        195                 200                 205
Ser Leu Gln Pro Glu Asp Phe Ala Thr Tyr Tyr Cys Gln Gln Pro Ile
    210                 215                 220
```

```
                                            -continued

Ala Arg Pro Pro Thr Phe Gly Gln Gly Thr Lys Val Glu Ile Lys Arg
225                 230                 235                 240

Ala Ala Ala His His His His His Gly Ala Ala Glu Gln Lys Leu
                245             250                 255

Ile Ser Glu Glu Asp Leu Asn Gly Ala Ala
            260             265
```